US006350609B1

United States Patent
Morozov et al.

(10) Patent No.: US 6,350,609 B1
(45) Date of Patent: *Feb. 26, 2002

(54) ELECTROSPRAYING FOR MASS FABRICATION OF CHIPS AND LIBRARIES

(75) Inventors: Victor Morozov; Tamara Ya. Morozova, both of New York, NY (US)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/446,188

(22) PCT Filed: Jun. 19, 1998

(86) PCT No.: PCT/US98/12768

§ 371 Date: May 8, 2000

§ 102(e) Date: May 8, 2000

(87) PCT Pub. No.: WO98/58745

PCT Pub. Date: Dec. 30, 1998

Related U.S. Application Data

(60) Provisional application No. 60/050,274, filed on Jun. 20, 1997, and provisional application No. 60/055,287, filed on Aug. 13, 1997.

(51) Int. Cl.[7] .................. C12M 1/36; G01N 15/06; C12Q 1/68; C25D 5/54
(52) U.S. Cl. ............... 435/283.1; 435/287.2; 435/6; 422/50; 422/68.1; 205/158; 427/2.13
(58) Field of Search ............... 422/68.1, 50; 435/283.1, 435/6, 287.2; 427/2.13; 205/158; 436/86

(56) References Cited

U.S. PATENT DOCUMENTS

| | | | |
|---|---|---|---|
| 4,072,551 A | 2/1978 | Dabal et al. ............... 156/378 |
| 4,322,449 A | 3/1982 | Voss et al. ............... 427/3 |
| 4,464,468 A | 8/1984 | Avrameas et al. ............ 435/177 |
| 4,748,043 A | 5/1988 | Seaver et al. ............... 427/30 |
| 4,885,076 A | 12/1989 | Smith et al. ............... 204/299 |
| 5,247,842 A | * 9/1993 | Kaufman et al. ........... 73/865.5 |
| 5,279,932 A | 1/1994 | Miyasaka et al. ........... 430/495 |
| 5,326,598 A | 7/1994 | Seaver et al. ............... 427/473 |
| 5,482,867 A | 1/1996 | Barrett et al. ............... 436/510 |
| 5,504,329 A | 4/1996 | Mann et al. ............... 250/288 |
| 5,543,164 A | 8/1996 | Krochta et al. ............. 426/302 |
| 5,481,110 A | 11/1996 | Krishnaswamy et al. ... 250/288 |
| 5,572,023 A | 11/1996 | Caprioli ............... 250/288 |
| 6,033,913 A | * 1/2000 | Morozov et al. ............. 136/86 |

OTHER PUBLICATIONS

Fodor et al., "Light–directed, spatially addressable parallel chemical synthesis", *Science,* 251:767–773 (1991).

Pritchard et al., "Patterning and regeneration of surfaces with antibodies", *Analytical Chemistry,* 67:(19)3605–3607 (1995).

Johnson et al., "Reproducible electrodeposition technique for immobilizing glucose oxidase and a differentially permeable outer–membrane material for use on a miniature implantable glucose sensor", *American Chemical Society,* 84–95 (1994).

Newman et al., "Ink–jet printing for the fabrication of amperometric glucose biosensors", *Analytical Chimica Acta,* 262:13–17 (1992).

Quist et al., "Imaging of single antigens, antibodies, and specific immunocomplex formation by scanning force microscopy", *Scanning Microscopy,* 9:394–401 (1995).

(List continued on next page.)

Primary Examiner—Stephanie W. Zitomer
Assistant Examiner—BJ Forman
(74) *Attorney, Agent, or Firm*—Browdy and Neimark

(57) ABSTRACT

A method of fabricating deposits of non-volatile substances, including biomacromolecules, in the form of spots and filing on a substrate surface by electrospray, where the deposits are used to determine the interaction of the deposited non-volatile substances to other substances. Also included in this method is the mass fabrication on a single chip of an array of single and multicomponent microsamples.

43 Claims, 32 Drawing Sheets

OTHER PUBLICATIONS

Strike et al., "Spatially controlled on–wafer and on–chip enzyme immobilization using photochemical and electrochemical techniques", *American Chemical Society,* 298–307 (1994).

Przybylski et al., "Electrospray mass spectrometry of biomacromolecular complexes with noncovalent interactions–new analytical perspectives for supramolecular chemistry and molecular recognition processes", *Angew. Chem. Int. Ed. Engl.,* 35:806–826 (1996).

Carswell et al., "A new method for the preparation of thin films of radioactive material", *J. Nuclear Energy,* 4:51–55 (1957).

Hoyer et al., "Electrostatic spraying:a novel technique for preparation of polymer coatings on electrodes", *Anal. Chem.,* 68:3840–3844 (1996).

Thundat et al., "Electrostatic spraying of DNA molecules for investigation by scanning tunneling microscopy", *Ultramicroscopy,* 1083–1087 (1992).

Robinson, "The production of radioactive sources by the electrospraying method", *Nuclear Instruments and Methods,* 40:136–140 (1966).

Morozov et al., "New methods for depositing and imaging molecules in scanning tunneling microscopy", *Scanning Microscopy,* 7(3)757–779 (1993).

Bertolini et al., "Improvements of electrospraying technique", *Nuclear Instruments and Methods,* 32:355–356 (1965).

Bruninn et al., "Electro–spraying: A method of making samples for β counting allowing accurate correction for self scattering and self–absorption", *Nuclear Instruments and Methods,* 13:131–140 (1961).

Fodor et al., "Multiplexed biochemical assays with biological chips", *Nature,* 364:555–556 (1993).

Pease et al., "Light–generated oligonucleotide arrays for rapid DNA sequence analysis", *Proc. Natl. Acad. Sci. USA,* 91:5022–5026 (1994).

Chrisey et al., "Fabrication of patterned DNA surfaces", *Nucleic Acids Research,* 24:3040–3047 (1996).

Blanchard et al., "High–density oligonucleotide arrays", *Biosensors & Bioelectronics,* 11:687–690 (1996).

Andersen et al., "Electrospray ionization and matrix assisted laser desorption/ionization mass spectrometry: Powerful analytical tools in recombinant protein chemistry", *Nature Biotechnology,* 14:449–456 (1996).

Eijk et al., "Preparation of thin sources, a review", *Nuclear Instruments and Methods,* 112:343–351 (1973).

Lauer et al., "Preparation by electro–spraying of thin uranium, plutominum and boron samples for neutron cross section measurements in 4Π geometry", *Nuclear Instruments and Methods,* 21:161–166 (1993).

Lemmo et al., "Characterization of an inkjet chemical microdispenser for combinatorial library synthesis", *Anal. Chem.,* 69:543–551 (1997).

Verdingh et al., "Equipment for electrospraying", *Nuclear Instructions and Methods,* 31:355–356 (1994).

* cited by examiner

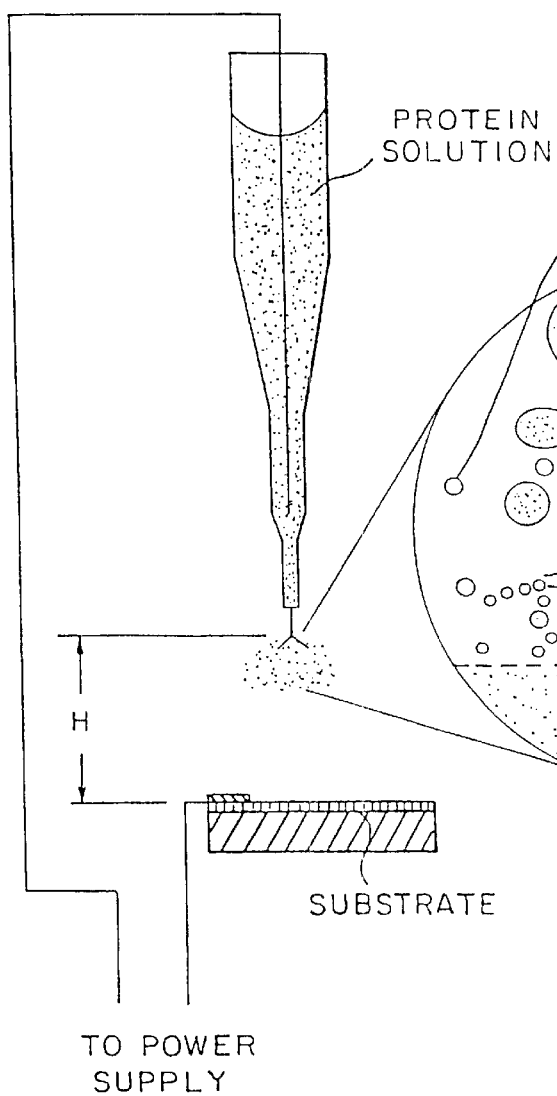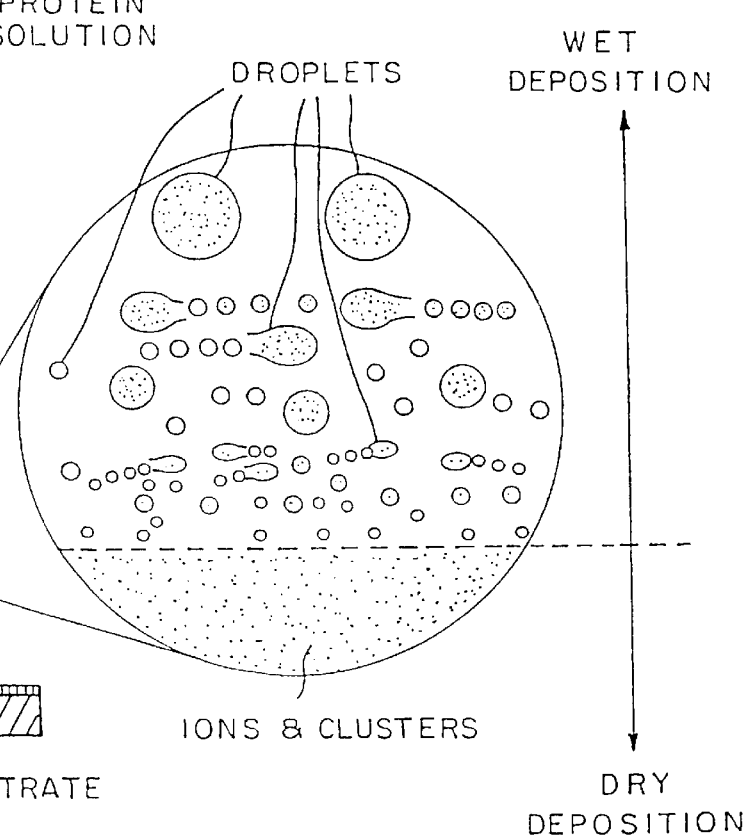
FIG. 1A
FIG. 1B

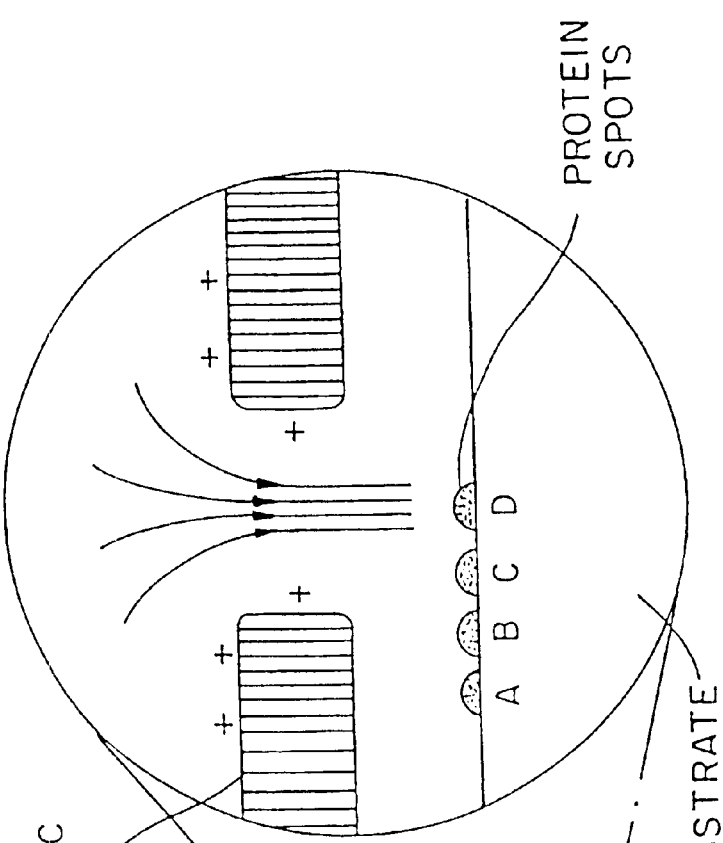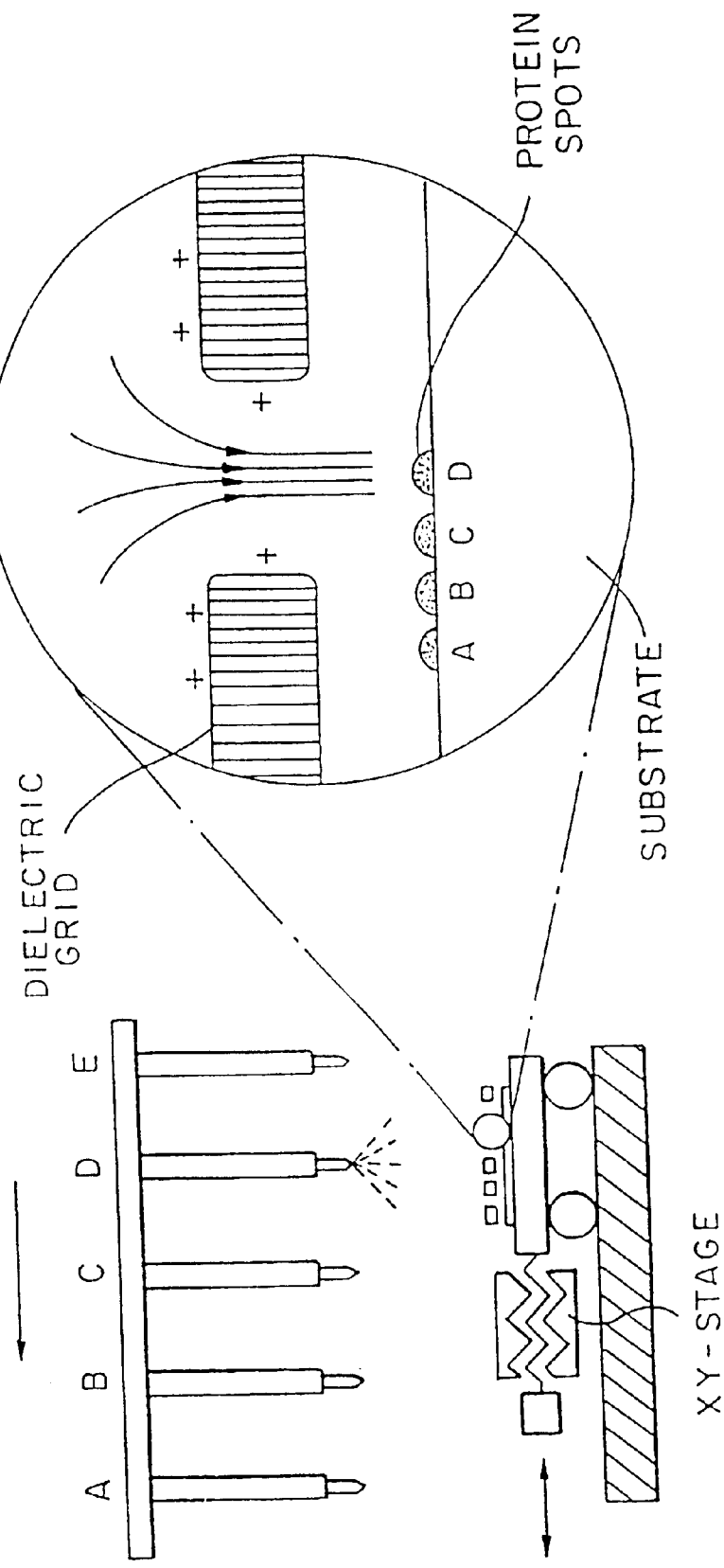

FIG. 26
FIG. 27
FIG. 28
FIG. 29A
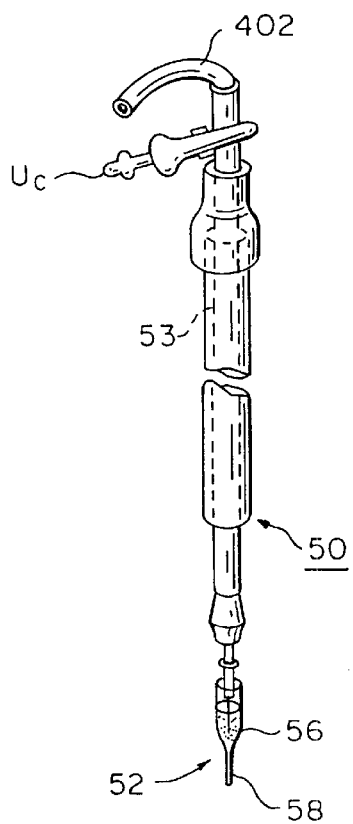
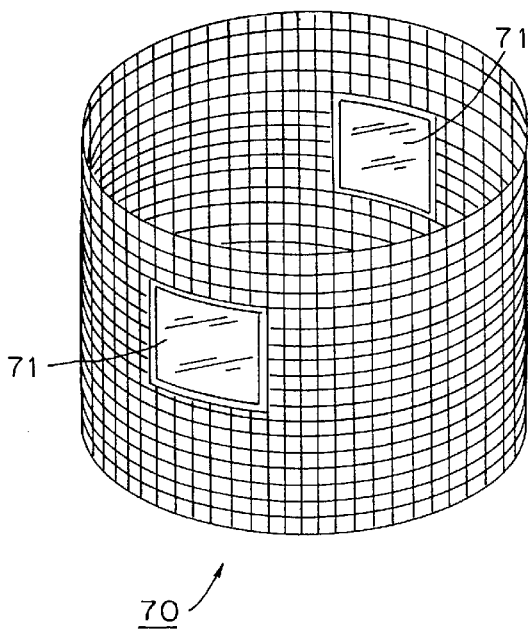
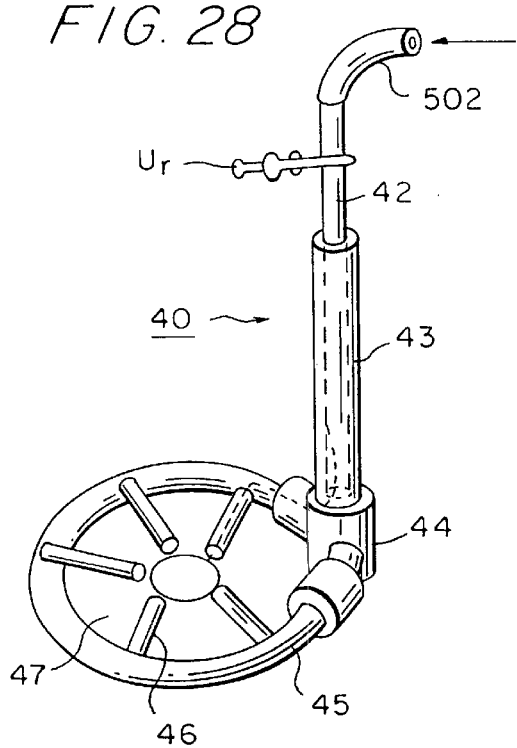
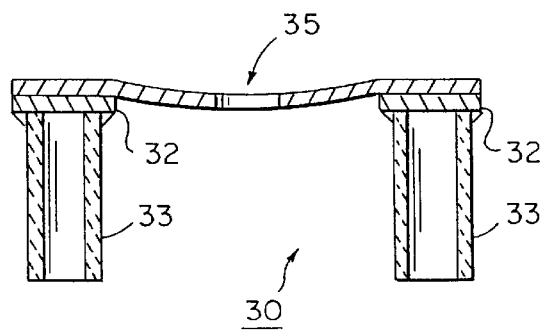

FIG. 31
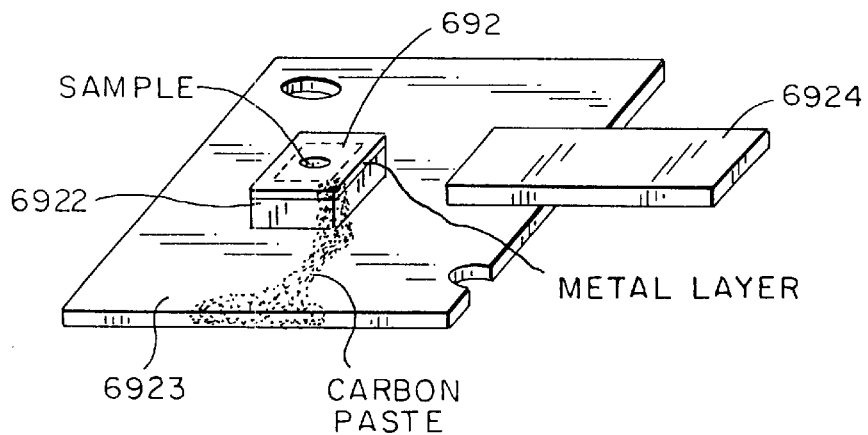
FIG. 32A
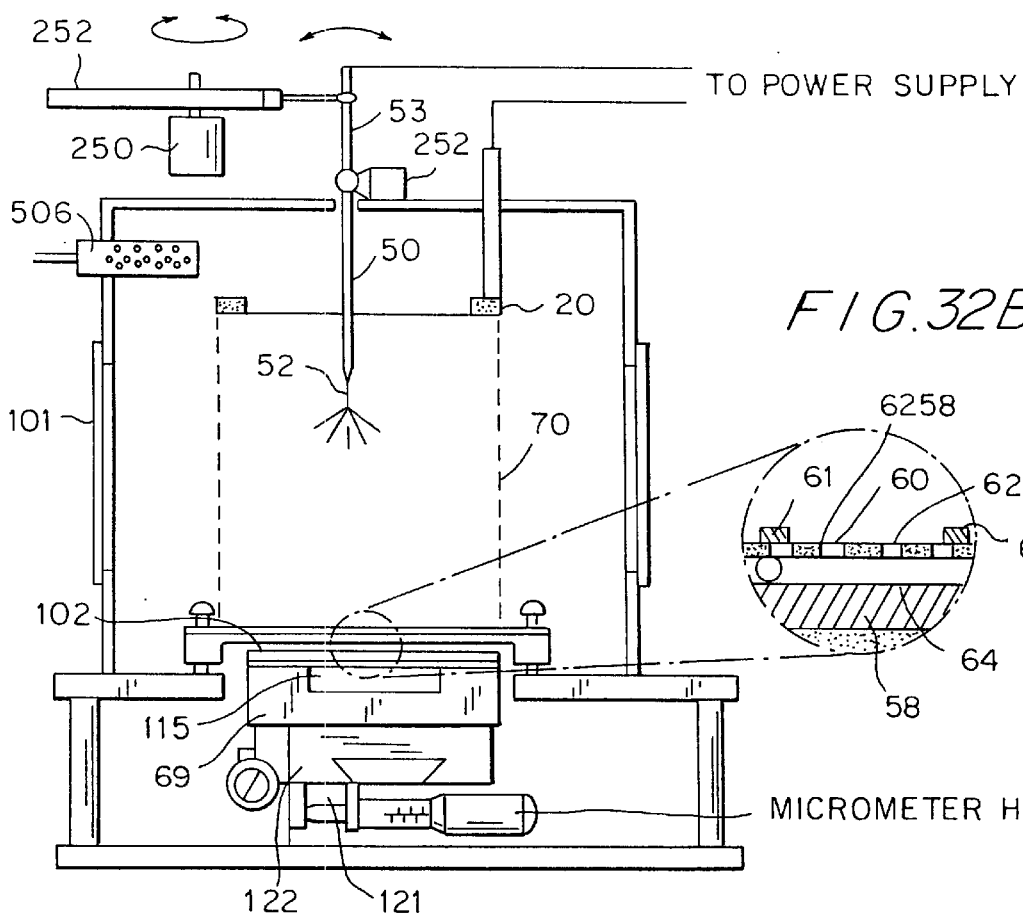
FIG. 32B

ELECTROSPRAYING FOR MASS FABRICATION OF CHIPS AND LIBRARIES

CROSS-REFERENCE TO RELATED APPLICATIONS

The present application is a 371 of PCT/U.S. Ser. No.98/12768 filed Jun. 19, 1998 and claims priority from U.S. provisional applications Ser. No. 60/050,274, filed Jun. 20, 1997, and Ser. No. 60/055,287, filed Aug. 13, 1997, the entire contents of which are hereby incorporated by reference.

BACKGROUND OF THE INVENTION

1. Field of the Invention

The present invention relates to the deposition of samples of substances, including biological molecules, such as proteins and DNA, into a specified shape or pattern over a substrate surface and to rapid drying and microconcentration of small amounts of substances from their solutions.

2. Description of the Background Art

The method of electrospray is the electrostatic atomization of a liquid or a solution to obtain charged microdroplets, charged clusters and ions. The solution or liquid of the substance to be deposited is placed into a capillary (or array of capillaries), and the application of high voltage results in instability of the liquid or solution, which is then dispersed into small charged droplets 0.3–20 microns in diameter, and typically about 0.5–2 microns in diameter. Electrostatic repulsion rapidly moves these charged microdroplets from the capillary tip, and in their travel toward a substrate surface, the microdroplets evaporate if solvent vapor pressure is low enough, and the size of the droplets reach a Raleigh limit of electrostatic stability. Afterwards, the microdroplets undergo a series of decays, reducing their size to about 10–20 nm and increasing the electrostatic field to a level where evaporation of ionized solvated molecules becomes possible. On further travel through a dry gas, solvent is lost from these solvated ionized molecules. Where evaporation proceeds rapidly, all of the solute content of the microdroplets can be concentrated into small nanoclusters (FIG. 1).

Electrospray of solutions in solvents with low vapor pressure, such as water, electrospray in atmosphere containing large amount of solvent vapor or where the electrospray source is at a short distance from the substrate surface for deposition, can allow microdroplets to reach the substrate without complete decay and evaporation of all the solvent. This regime is referred to as wet electrospray. The deposition of charged molecules or clusters occurs in a dry electrospray regime where volatile solvents is used and the conditions of low partial vapor pressure of the solvent in gas or a longer distance between the electrospray source and the substrate surface is used.

Accordingly, this electrospray phenomena permits the deposition of substances in the form of charged microdroplets, solvated or dry ionized molecules, or nanoclusters. Nanoclusters or fibers can be produced by electrospray from linear polymers. The form of deposit can be regulated by changing the travel path of the charged species and their speed, by control of vapor pressure in the atmosphere, and by the proper choice of solvent and solution concentration.

One of the earliest applications of electrospraying was in the production of thin sources for radioactivity measurements. In this application, a collimator for providing electrostatic focusing was introduced (Robinson, 1965; van der Eijk et al., 1973). Bruninx et al. (1961) further disclosed a plexiglass disc with a center hole through which the electrospray passes before it reaches the substrate or collector. To obtain thin radioactive sources with a well-defined area, van der Eijk et al. (1973) disclosed that masks can be used, and further disclosed that masks made of Teflon, as first reported by Blumberg et al. (1962), can give rise to the production of thin radioactive sources with diameters appreciably lower than the diameter of the hole in the mask.

Other applications of electrospraying, such as paint spraying, pesticide spraying, and use as a source of ions for mass spectrometry of biological molecules, are reviewed in Michelson (1990). Thus, the electrospraying of biological molecules was developed for use with mass spectrometry to characterize the molecular weight, structural features and non-covalent interactions of biological molecules. The finding that the structural integrity of protein ions was maintained and that non-covalent interactions were preserved was of primary significance for other electrospray applications of biomolecules. For instance, the electrospray mass spectrometry studies stimulated the use of electrosprayed deposits of DNA and protein molecules for imaging by scanning tunneling microscopy (Thundat et al., 1992; Morozov et al., 1993). Whereas Thundat et al. (1992) electrosprayed a solution of DNA molecules directly onto a gold substrate, Morozov et al. (1993) interposed a protective sheet, containing an ion canal, between the electrospray source and the substrate on which protein ions were deposited. Besides the destruction of both protein ions and the impact surface is well documented after collisions of accelerated protein ions with mica and graphite (Reimann et al., 1994; Sullivan et al., 1996).

Methods for patterning proteins and other biological molecules have been developed by adopting either conventional technologies, such as computer controlled robotics pipetting of microdroplets (Shalon et al., 1996), screen printing (Hart et al., 1994) and ink-jet deposition (Newman et al., 1992), or conventional electronic circuit manufacturing technologies, such as those using photo resists and lift-off techniques (Nakamoto et al., 1988). Methods of electrodeposition of protein from solutions onto prefabricated microelectrode arrays in biosensor technologies have also been developed (Strike et al., 1994; Johnson et al., 1994), but the application of electrodeposition is limited mostly to proteins and requires complex procedures of substrate preparation and microelectrode addressing. Furthermore, protein deposition from solution onto microelectrodes may damage protein molecules at the solution-metal interface due to direct oxidation and/or extreme local pH accompanying electrochemical reaction(s) at the electrode. These electrodeposition methods have only a few parameters for controlling the structure and density of a deposited film, and the electrodeposition from solution does not allow for modification of the electrode surface with water soluble polymer in such a way as to readily permit detachment of the sample from the substrate after cross-linking.

Shadow masking technique has been described recently as a method to pattern silicon surface with electrospray produced polypeptide fibers to increase surface adhesiveness to cells (Buchko et al., 1996). However, the conditions of electrospray, namely, use of formic acid as a solvent, are not compatible with preservation of tertiary structure and functional activity of a majority of biological macromolecules. Besides the use of shadow maskings, on the other hand, results in the loss of a large amount of electrosprayed material onto the mask itself. No reliable data were available concerning the retention of functional properties of electrodeposited protein and DNA molecules.

For the deposition of DNA molecules, Cheng et al. (1996) revealed numerous altered DNA molecules in electrophoretic analysis of plasmid DNA electrodeposited on a dry stainless steel electrode. No such alterations were found in experiments where DNA was electrodeposited into a buffer droplet.

Robinson (1966) discloses two copper annular discs around the electrospray tip, designated as a guard ring and a collimator.

Bertolini et al (1965) disclose a hole having an interior surface shaped as a truncated, inverted cone.

Bruninx, et al (1961; see pp. 132–133) disclose a hole in a plexiglass disc laid over a substrate of -aluminum foil so that the substrate is "covered" by the disc. The substrate rotates and the single hole is centered on the axis of rotation. This arrangement is said to ensure uniform distribution of spray over the uncovered area. From this, two things can be inferred: first, that the spray pattern from the electrospray tip is irregular, because the substrate must be rotated to ensure even distribution; and second, that the plexiglass disc of Bruninx et al acts in the manner of a spray-paint template, merely blocking covered areas of the substrate rather than influencing the paths of the charged particles by electrostatic fields. Bruninx refers to a "well-defined area", i.e., an area with sharp boundary; such an area is not to be expected with electrostatic focusing.

Morozov et al (1993) report on an apparatus including a sheet with double-layered electrodes and having a central ion canal (see FIG. 2, p. 760). The ion channel, said to be made from a plastic tube, is shown as conical. A potential difference is set up across the two electrode layers, which are separated by an insulating center sheet.

Methods of fabricating biochips using photochemical reactions have also recently been developed by a number of different groups (U.S. Pat. No. 4,562,157; Ehatia et al., 1993; Pritchard et al., 1995; Pease et al., 1994; Fodor et al., 1991). These methods use light to direct the combinatorial chemical synthesis of biopolymers on a solid support in a miniaturized pattern or to provide a light-addressable surface onto which proteins and DNA can be immobilized. A photolithographic mask is used to direct light to specific areas of the light-addressable surface to effect localized photodeprotection.

According to the methods of fabricating biochips using photochemical reactions, the deposition of each molecule into a pattern requires a minimum of three steps: (1) photoactivation (photodeprotection) of the substrate surface by irradiation with light at specific locations; (2) bringing the activated substrate into contact with a solution of molecules to be deposited; and (3) washing of unbound molecules (FIG. 2). These three steps are repeated for every new substance to be deposited on the surface. However, there are a number of disadvantages with these prior art technologies. These disadvantages include:

(i) the amount of material deposited in each spot is limited due to the limited number of functionalized groups appearing after irradiation;

(ii) every deposition cycle requires exposure of the entire surface to the solution of molecules to be deposited, which inevitably leads to a fraction of these molecules binding non-specifically to non-irradiated (non-photoactivated) areas, which creates problems in the design of complex patterns of proteins and other molecules;

(iii) another source of contamination is the solution interface which is always enriched with surface active impurities; and (iv) diffraction effects and light scattering result in irradiation beyond the pattern area, decreasing the resolution and causing cross-contaminating of spots.

Citation of any document herein is not intended as an admission that such document is pertinent prior art, or considered material to the patentability of any claim of the present application. Any statement as to content or a date of any document is based on the information available to the applicant at the time of filing and does not constitute an admission as to the correctness of such a statement.

SUMMARY OF THE INVENTION

It is accordingly an object of the present invention to overcome the deficiencies in the art, such as noted above.

The present invention provides a method of fabricating samples of non-volatile substances by electrospray deposition, such as a sample-containing chip, where the samples are to be used to determine the interaction of the deposited non-volatile substances in the sample with other substances. The present invention further provides a method for simultaneous fabrication of many chips, each containing a single or multiple samples of biological or other types of molecules. Such chips have many uses. In particular, monocomponent chips can be used as replaceable sensitive elements of chemo-sensors. Multicomponent chips (libraries) can be used in multianalyte assays, such as microELISA, nucleic acid hybridization analysis, in screening for effective enzyme inhibitors, etc. Both microchips (micron-scale size of each sample on the chip) and macro-chips (millimeter and centimeter scale) can be prepared by the same technology. Such macro-chips can be used for example to prepare diagnostic tests for sensitivity to allergens, for analysis of microbial sensitivity to antibiotics, etc.

The present invention further provides for the efficient fabrication of microsamples of cross-linked protein or DNA films from nanogram quantities of material. Moreover, the proteins and DNA molecules in the microsample films which are electrospray-deposited retain their functional properties.

Still further, the present invention provides an apparatus for fabricating samples of non-volatile substances by electrospray, as well as the sample product formed by the present electrospray method.

BRIEF DESCRIPTION OF THE DRAWINGS

FIG. 1A is a schematic of an electrospray process illustrating the different state of the sprayed substance at different distances from the electrospray capillary tip. FIG. 1B is an enlarged partial of FIG. 1A view showing that microdroplets of solution predominate in the wet zone, and dry clusters and ions predominate in the dry zone.

FIG. 3B) in the electrospray deposition of charged particles through a hole in a dielectric mask.

FIG. 9A schematically shows the mass fabrication of multicomponent matrices by using a means for shifting the position of the mask relative to the substrate after each of a series of substances are electrodeposited onto a substrate through the holes in the mask.

FIG. 9B shows an enlarged partial view of FIG. 9A.

In FIG. 15C, the ordinate represents the square of the distance that dye molecules diffuse from small particles of solid dye applied onto the surface of wet protein films in a humid atmosphere. Empty and filled circles represent data for Bromphenol blue in dried and electrospray deposited films, respectively. Empty and filled squares represent the diffusion of Janus green B dye in dried and electrospray deposited films. The abscissa is the time of diffusion.

In FIG. 16A, the conical screen concentrates charged particles directly on substrate or on hole in mask. The design presented in FIG. 16B allows an even de deposition. The specific activity of the electrospray-deposited samples is relative to the specific activity in the initial solution. The electrospray deposition conditions are +4 kV at the capillary with an internal electrode, current of 10–50 nA and flow rate of 6 $\mu$L/h.

FIG. 26 is a perspective view of the capillary of the electrospray chamber.

FIG. 27 is a perspective view of the grid screen of the electrospray chamber.

FIG. 28 is a perspective view of the collecting ring of the electrospray chamber.

FIG. 29A is a cross-sectional view of the protective screen of the electrospray chamber.

FIG. 31 is a perspective view of a sample holder.

FIG. 32A is a schematic elevational view, similar to FIG. 25, of a second embodiment of the electrospray chamber.

FIG. 32B is a detail view of FIG. 32A.

DETAILED DESCRIPTION OF THE INVENTION

Figure 2:
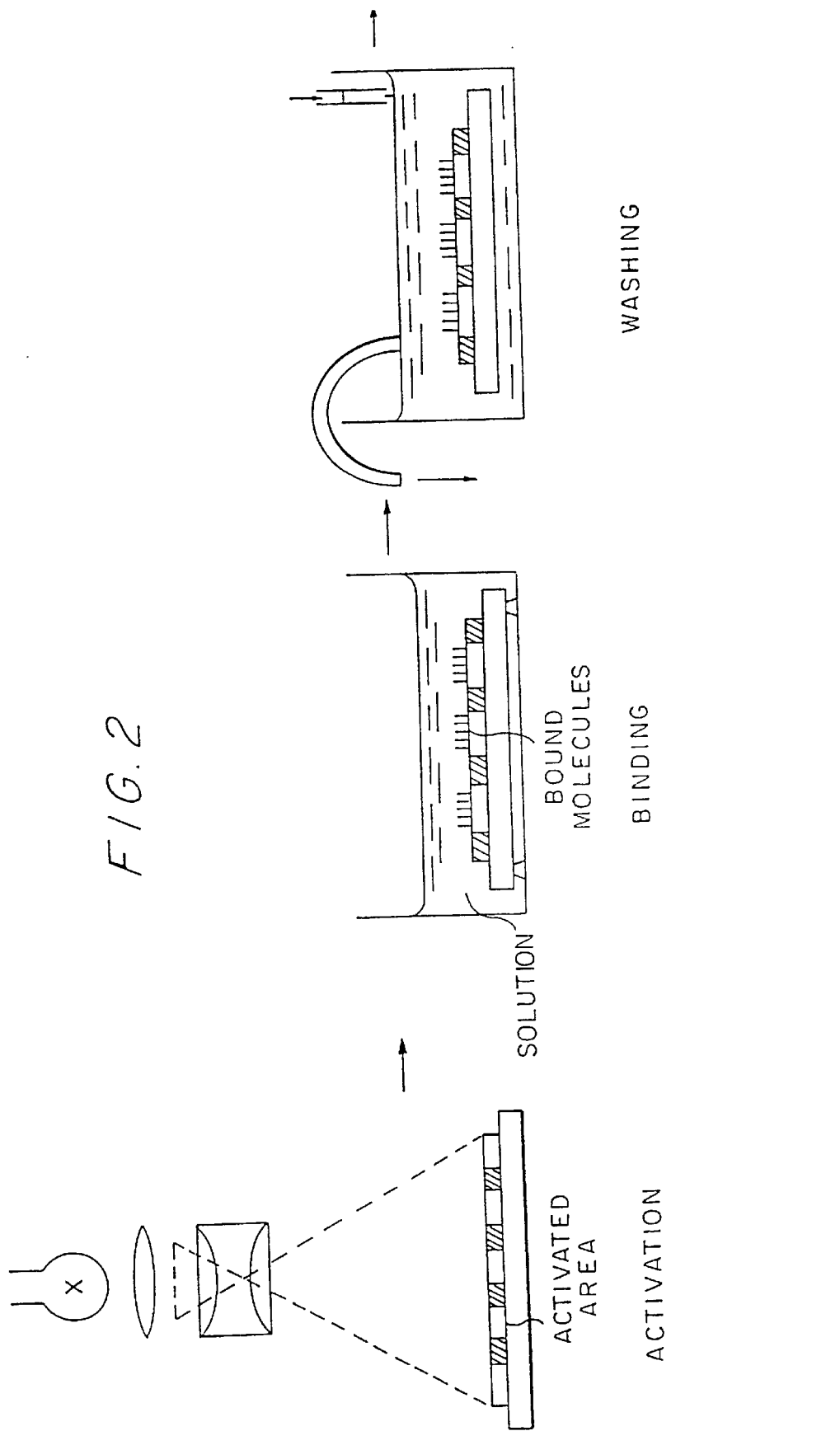
FIG. 2 schematically shows the steps in deposition of molecules into a pattern using light-addressable functionalization of substrate according to the prior art.

The method according to the present invention was developed to provide the fabrication of chips made from sample deposits of non-volatile substances which include biomolecules (e.g., biomacromolecules such as proteins and DNA), organic molecules (such as antibiotics and pharmaceuticals), inorganic substances, salts, inorganic colloids, etc., which are deposited into a particular shape or into an array. The present method has the advantage over conventional methods of patterning biomolecules in that: (1) there is no contact of the whole chip surface with solvent and different spots are not cross-contaminated as in the photolithographic method; (2) in contrast to the ink-jet method, deposition onto many chips occurs simultaneously, thereby accelerating the process; (3) the size of charged clusters and molecules is much smaller than in the ink-jet method, thereby facilitating the fabrication of much smaller spots; (4) the same technology can be used to fabricate both micro- and macro-chips; and (5) deposition can be performed under dielectric liquid, in any gas atmosphere and/or at low temperature.

The present method uses a mask having either a single non-round hole or an array of holes (of any shape) in a pattern, and which mask is interposed between an electrospray source and the substrate surface on which a sample is to be deposited. Thus, the charged microdroplets, clusters or ions can be directed through a hole or an array of holes in a mask and onto a substrate surface. In the case of a mask having an array of holes, the method according to the present invention would provide the virtually simultaneous formation of as many distinct spots on the substrate -surface as the number of holes in a mask positioned over the substrate. Shifting the mask after deposition of each compound will result in the formation of a multi-component chip (library) under each hole.

It is within the scope of the present invention to use other methods of creating local electric fields attracting charged particles. In particular, conductivity of a photoconductive dielectric layer on a target electrode can be locally increased by illumination, as shown schematically in FIG. 4B. The pattern of deposition follows the pattern of illumination, as demonstrated in FIG. 5D. Local heating of a dielectric layer, injection of charge carriers (Reiser et al., 1969), irradiation and other physical factors known to modify conductivity of dielectrics can also be used to control electrospray deposition in the same manner as masks with holes.

When electrospray deposition is performed through a thin conducting mask under the same potential as the substrate and positioned in close vicinity to it, the deposits exactly follow the form of the hole in the mask with sample molecules uniformly distributed over the deposit. However, much of the molecules in the sample are deposited and lost onto the mask itself, thereby making this configuration of the electrostatic field for electrospray quite ineffective and time consuming.

Figure 3A:
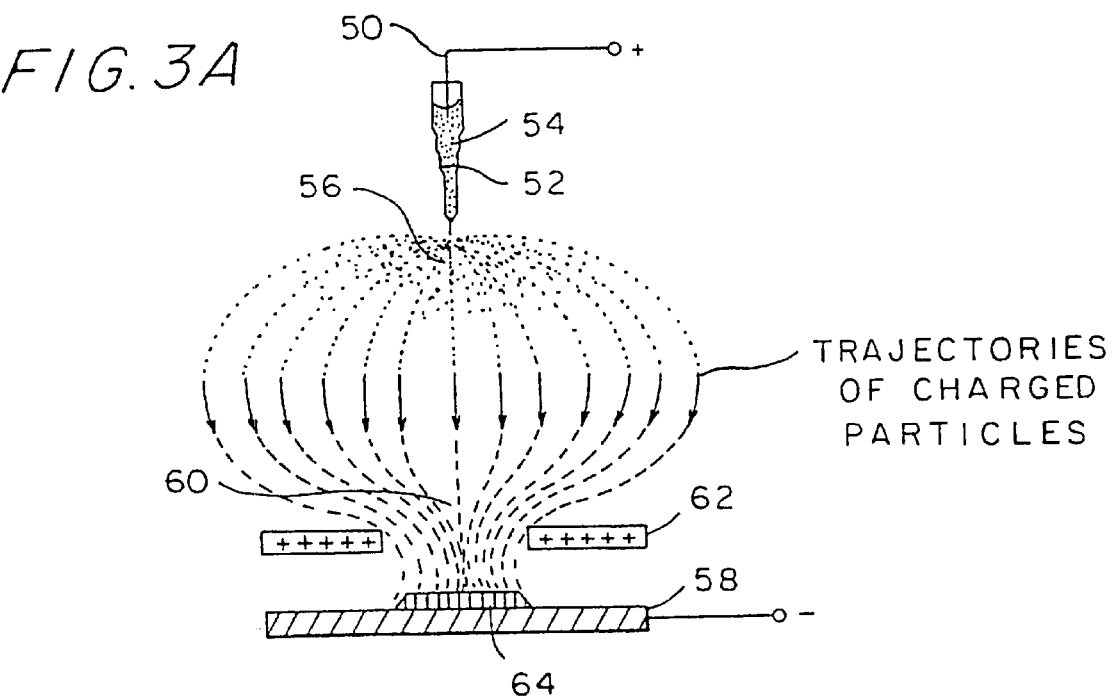
FIGS. 3A and 3B schematically illustrate the electrostatic concentration effect (FIG. 3A) and the electrofocusing (electrostatic lens effect.
Figure 3B:
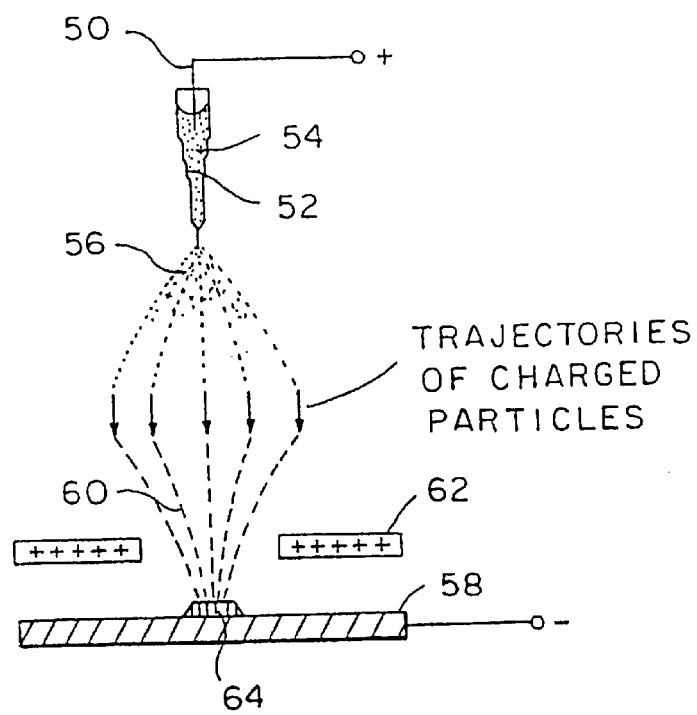
Figure 4A:
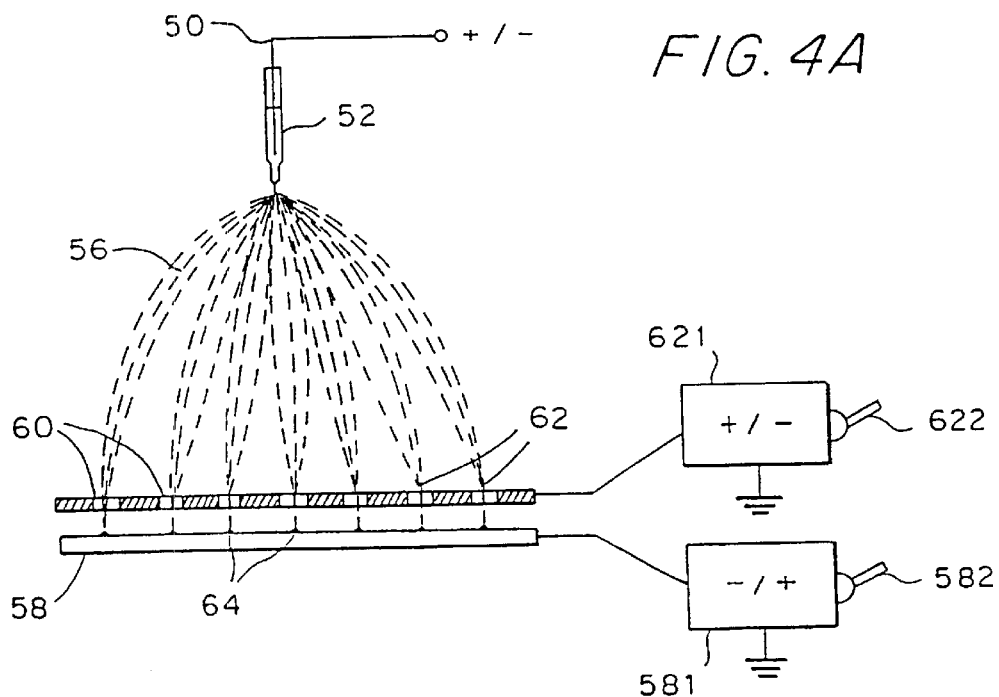
FIG. 4 schematically illustrates the distribution of electrosprayed charged particles into numerous spots through an array of holes in a dielectric mask (FIG. 4A) and deposition onto illuminated conductive areas of a photo-conductive dielectric layer (FIG. 4B).
FIG. 4C is a schematic cross-sectional view of the substrate of FIG. 4B.

However, when the mask is under a potential of the same sign as that of the electrospray source and microdroplets, the preferential deposition of electrosprayed material onto the substrate is very efficient because the charged mask repels the electrosprayed material and changes their trajectory so that they pass through the hole(s) in the mask. The phenomena connected with the repelling effect of a charged dielectric or conductive mask are distinguished here. The first phenomenon is referred to as "electrostatic concentration", which describes the repulsion of charged particles from all mask areas except those in the vicinity of a hole or in the vicinity of an illuminated spot in a photoconductive dielectric where particles are collected by the electrostatic field protruding through the hole, as shown in FIG. 3A. An electrode 50 with a positive charge deposited in a capillary 52 destabilizes a solution of non-volatile material 54 which is electrosprayed from the capillary tip as a torch 56 where the trajectories of the particles (represented by arrows) towards the substrate 58 are deviated and concentrated through a hole 60 in a charged mask 62 used to deposit a film 64 with size and form corresponding to the hole. Such an even deposition is possible only if all possible trajectories are available for charged particles as shown in FIG. 3A. In the second phenomenon, when the spatial angle at which charged particles approach the hole is close to normal, as illustrated in FIG. 3B (electrospray at the lowest possible voltage) and in FIG. 4 (with many closely placed holes), the uneven electrostatic field in the vicinity of a hole or an illuminated spot will deviate their trajectories to the center of the hole. This redistribution of the deposit within the area under the hole is referred to as "electrofocusing" or the "lens" effect. In the latter case, the electrosprayed material is deposited as spots having a size smaller than holes in the mask. All the charges shown in FIGS. 3A and 3B can be opposite in charge without affecting the overall process.

It is noteworthy that the operation of this electrostatic lens is different from that in electronic microscopes because the inertial forces which determine the trajectories in a vacuum electrostatic lens are negligible in air under normal conditions where viscous forces dominate. This electrostatic lens effect has the advantage that the size of the deposits are substantially smaller than the holes in the mask, which considerably reduces the technological problems in the fabrication of masks suitable for deposition of deposits (spots) of micron and submicron sizes since the holes do not need to be as small as the spots themselves.

Figure 5A:
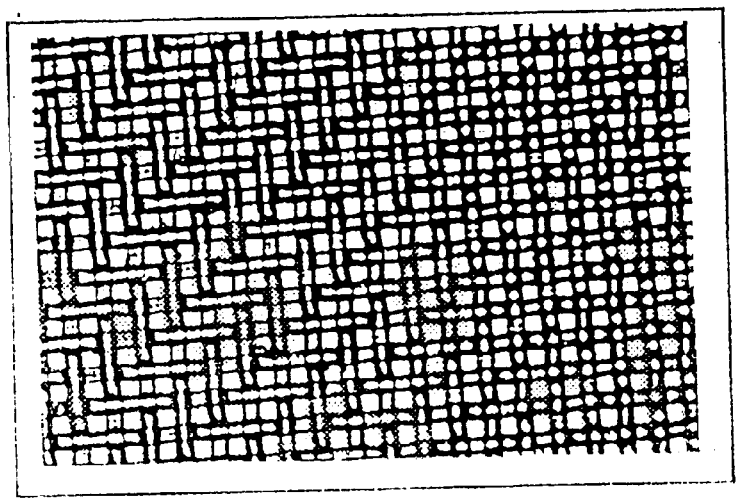
FIGS. 5A–5D show the polypropylene mask (FIG. 5A), myoglobin spots electrospray deposited through holes in the mask onto glass covered with conductive $SnO_2$ layer (FIG. 5B), dye spots (FIG. 5C) deposited through the same mask onto mica in wet atmosphere and dye spots (FIG. 5D) deposited onto a photoconductive dielectric layer illuminated with a diffraction pattern of a laser beam.
Figure 5B:
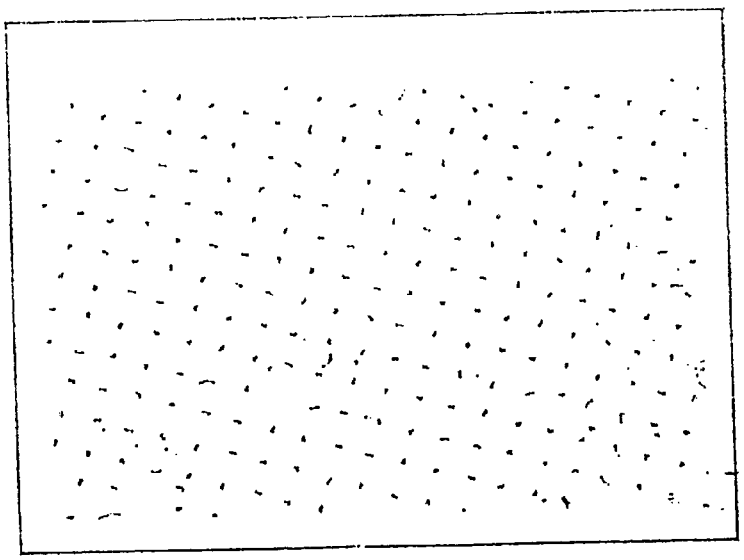
Figure 5C:

The results of the electrostatic lens effect using a polypropylene woven tissue as a mask are shown in FIGS. 5A–5B where the 5–7 micron size of protein spots (FIG. 5B) is considerably smaller than the 23–24 micron holes which are set 47 microns apart in a polypropylene tissue used as a mask (FIG. 5A). An advantage of electrostatic concentration is that the electrosprayed material is deposited with close to 100% efficiency since the mask absorbs only a small fraction of the charged molecules. FIGS. 14A and 14B illustrate that even film deposits can be produced in conditions where the electrofocusing effect is suppressed due to the presence of a single hole in the mask.

The electrostatic lens effect can also be used to produce samples with a high height-to-lateral size aspect, as illustrated in Example 10, where arrays of needle-like samples of RNAse are fabricated with the use of a mask as shown in FIG. 5A. Arrays of such rod-like samples were also fabricated from organic substances, such as light green dye. It can be 5 concluded from these experiments that, even under relatively dry conditions (18% humidity in Example 10), a protein film has enough conductivity to allow the passage of incoming charges through the film thickness of no less than 40 microns. The high electric field and the injection of charge carriers during the electrospray deposition can be responsible for such enhanced conductivity of protein deposits, as well as deposits of organic substances (Reiser et al., 1969).

The mask used in accordance with the present invention has a single hole or an array of holes and is positioned between the electrospray source (capillary) and the target. The mask can be preferably made from a non-conducting material, where the concentrating electrostatic effect is automatically achieved when the first charged molecules of the electrospray are adsorbed onto the mask surface, thereby electrostatically blocking any further adsorption of charged molecules. The non-conducting parts (areas) of the mask with a layer of adsorbed charged molecules then serves to direct all the charged molecules of the electrospray into the hole(s) of the mask for deposition onto a substrate. A similar electro-concentrating effect is also observed when a dielectric photoconductive layer is used as a substrate.

The mask can also be made of a conducting material. However, the potential on the conducting mask used according to the method of the present invention should be adjusted to be intermediate between the potential on the electrode on the capillary and the potential on the substrate in order to direct the charged molecules into the holes and thereby avoid the considerable loss of electrosprayed material.

It was discovered that while electrofocusing as a result of an electrostatic lens effect occurs quite readily with a mask having an array of holes which are spaced close together, electrofocusing is less pronounced or absent with a single hole and with holes separated by a distance much larger than their diameter. In the case of a single hole in a plastic plate directly placed onto a substrate, maximum electrofocusing was achieved when the plate thickness was about 0.5 times the hole diameter. However, if a thin mask with similar a hole was placed over a substrate in such a way as to have its upper surface at the same distance from the substrate as that in a thick plate, then the degree of electrofocusing dropped and shape of the deposit deviates from that of the hole. These features indicate that not only electrostatic but aerodynamic forces induced by ion-wind control the electrofocusing process. It was also found that electrofocusing depends on the voltage applied to the capillary (deposition with a minimum voltage on the capillary results in larger focusing) and on the position of the capillary relative to the hole (a minimum spot is obtained with a capillary placed directly over the hole at close distances).

Thus, in order to obtain even distribution of material within the single hole of any shape, the following conditions are preferably fulfilled: (i) dielectric mask is thin; and (ii) placed close to the substrate; (iii) electrospray source is not positioned directly over the hole; (iv) substrate and mask are rotated around the normal axis through the center in the hole in the mask; and (v) there is a means for effecting turbulence of the air in the vicinity of the hole. The size and the shape of the deposit conforms to the size and shape of the hole under these conditions.

If electrofocusing is required under each hole then a thick mask with conically shaped holes is preferable.

When the mask 62 includes a dielectric, insulating, or semiconducting material, on which a static charge is built up by adsorption onto the mask surface of particles from the electrode, then the mask is preferably electrically isolated (or insulated) but optionally may be connected to ground to more-or-less slowly drain off accumulating excess charge, or it may be coupled to an electrostatic charging device as discussed below.

FIG. 4A is similar to FIGS. 3A and 3B and illustrates a plurality of the mask holes 60. The arrangement is similar to that of FIGS. 3A and 3B with an electrosprayer including a holder 50 and electrode/capillary 52 creating a mist of charged particles 56; however, in FIG. 4A, the mask, here also labeled 62, can be metallic or at least partly conductive (e.g., a sandwich of materials having different conductivities or including a semiconductor) and is preferably dielectric. In a conductor, any charge (e.g., on the mask 62) will migrate to the surfaces and concentrate in edges and points, as is well known from electrostatics. The electric potential gradient around all the holes should be identical if the hole geometry is identical.

The substrate 58 may be a dielectric or conductor or may have various conductivities. Preferably the substrate 58 is coupled to an electrostatic device (i.e., charging or electrostatic potential-inducing device) 581 with optional voltage adjustment 582. These may likewise be provided to the apparatus of FIGS. 3A and 3B (although not shown in FIGS. 3A and 3B). This first electrostatic device holds the upper surface of the substrate 58, adjacent to the deposit areas 64, at a first potential attractive to the charged particles 56.

The mask 62 may be insulated and depend on adsorbed (or induced) charges for its optimal polarity, but is optionally coupled to a second electrostatic device 621, which preferably includes a means for voltage adjustment 622, preferably independent from the substrate 58. The voltages may be optimized for focusing the particles onto target deposit areas 64 without deposit onto the mask 62. For example, the mask 62 is preferably held at a potential repulsive to the charged particles 56. Thus, the mask 62 may act as both a physical shield and an electrostatic field-influencing device.

The electrostatic devices 581 and 621 may include batteries, power supplies, voltaic cells, etc.; the adjustment means 622 may be any manual or automatic device for adjusting the voltage on the mask 62.

FIG. 4B shows another one of the preferred embodiments, employing light to induce a variable pattern of focusing charges.

The mask 62 is not limited to just conductors and dielectrics, but may be made of any material or materials including special materials such as semi-conductors and photoconductive polymers. In FIG. 4B, the mask 62 is embodied as an optical mask 162, and is (preferably) disposed below the substrate, here labeled 158, rather than above the substrate; it throws shadows on the underside of the substrate. In this embodiment the substrate 158 includes a layer of material whose electrical properties are photosensitive (herein termed "electrophotic"), e.g., a semiconductor or photovoltaic structure which creates surface voltage in response to light, a layer of photosensitive polymer, or other material. In the preferred version of this embodiment, the substrate 158 includes a sandwich including a transparent conductive sheet, acting as an electrode, and a photoconductive layer.

The layer 158 is most simply a perforated sheet of opaque material having holes 160 under the deposit areas 64. A lamp, laser, or other light source 170 shines preferably collimated light through the holes 160 to create deposits of the charged particle 56 as described below.

Alternatively, in the present invention the mask 162 may be eliminated and the desired light pattern be formed with a modulated scanning laser beam, triggered photocell or laser arrays, or some equivalent.

Figure 4B:
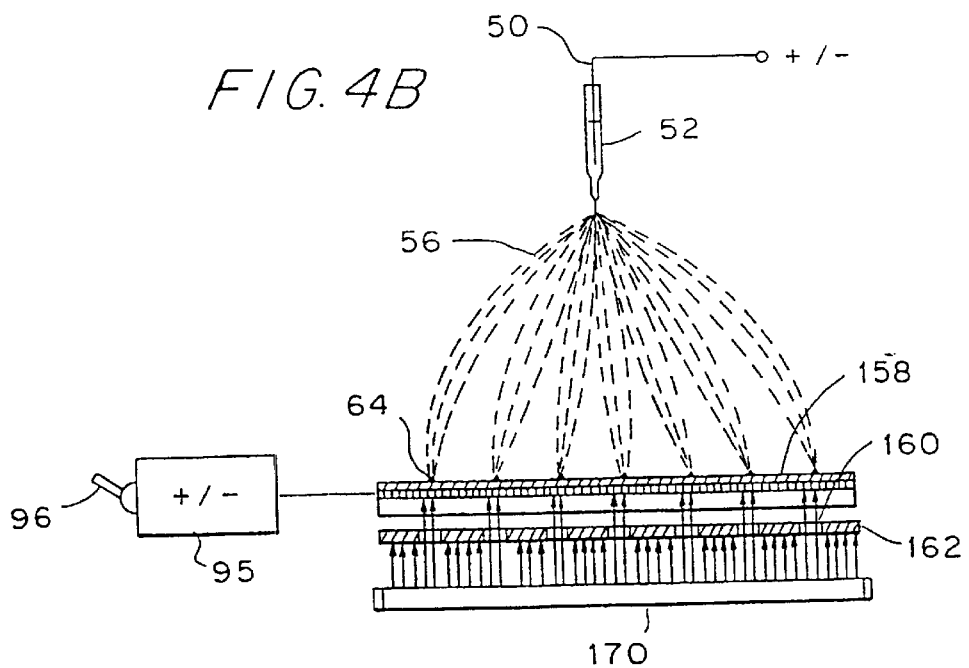
Figure 4C:
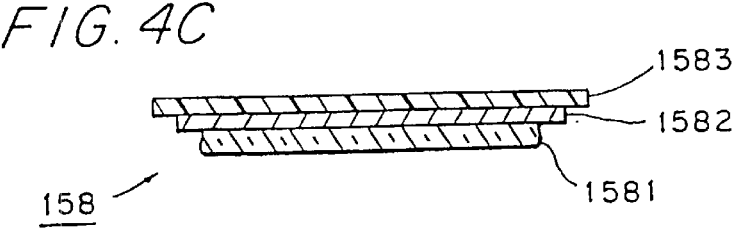

FIG. 4C is an elevational cross-section of the substrate 158 of FIG. 4B. Prom the bottom, substrate 158 preferably includes a transparent mechanical support layer 1581, which may be glass, acrylic sheet, etc.; a transparent conductive layer 1582; and a photosensitive layer 1583, which is preferably a photoconductive polymer. The transparent conductive layer may, for example, include a sheet of transparent conductive material or a partial metallic film on the substrate 1581.

A typical photoconductive polymer film is conductive in light and insulating in dark. Therefore, the portions of layer 1583 which are illuminated from below through the mask 160 will be at the same potential as the conductive sheet, because any excess static charge will drain away through the conductive layer 1582, which is preferably coupled to an electrostatic device 95 with optional voltage adjustment 96. It may also simply be grounded.

Meanwhile, the portions of layer 1583 which are not illuminated can reach a different potential through adsorption, or maintain a previous potential simply through non-conductance. If this different potential is repulsive to the mist particles 56 while the potential at the illuminated portions is attractive, the particles will only settle on the deposit areas 64 above the holes 160 of the optical mask 162.

Figure 5D:
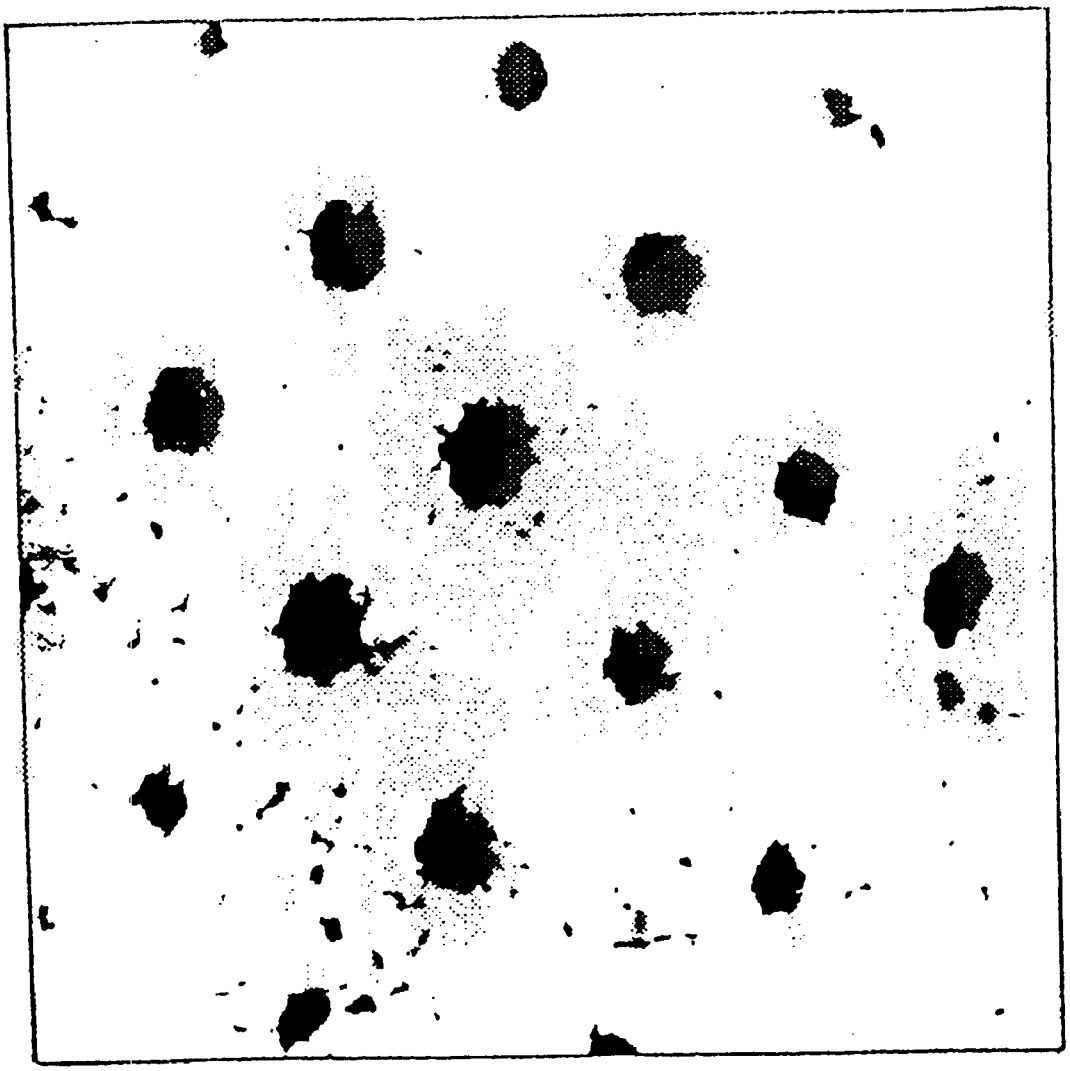

FIG. 5D shows results achieved by the electrophotic method of the present invention.

The illumination pattern may be a photographic negative, and the polarity from device 95 may be reversed at the same time to achieve the same effect (not shown). Any other electrophotic means for creating the potentials to achieve the deposits 64 is within the scope of the present invention.

In order for biomolecules, such as proteins and DNA, to retain their structural and functional properties when electrosprayed, the strength of the electric field at the capillary tip of the electrospray source is to be sufficient for effecting electrospray but not so high as to result in corona discharge, which destroys the functional properties of the biomolecules. The strength of the electric field at the capillary tip can be controlled by maintaining a constant current through the capillary and/or a constant voltage. The minimum voltage or current is empirically determined. It was discovered that the minimum voltage that enables an effective electrospray is dependent on the radius of the capillary, solution conductivity, flow rate, and the distance between the capillary and the substrate. With a capillary diameter of about 20–30 microns, and the capillary to substrate distance of about 15–40 mm, a protein solution is electrosprayed very effectively at a current of about 10–50 nA reached at a voltage of about 3–5 kV with a flow rate up to 1 microliter/min. Above 6 kV and a current exceeding 100 nA, the properties of the biological molecules are likely to be destroyed in the electrospray process. Replacement of air with freon, carbon dioxide or other corona-suppressing gas can be used to help prevent corona discharge. Corona discharge effects can also be inhibited if the electrospray is assisted by gas-jet atomization, from which micron-sized droplets can be obtained at considerably lower voltages than needed for electrospray alone. Jet-assisted electrospray drastically accelerates the deposition of material since stable dispersion can be obtained at much higher flow rates than with electrospray alone. Air-jet-assisted as well as ultrasound-assisted (such as with the Ultraspray apparatus produced by Analytica Company in Bradford) electrospray are especially effective in deposition of large samples or large number of samples, since they can easily disperse up to 1 mL/min of solution.

For the simultaneous electrospray deposition of multiple spots from a single capillary through a mask with an array of holes, the capillary preferably oscillates above the mask while the mask and the substrate/support for the electrospray deposits are being rotated to provide the uniform deposition of electrosprayed particles throughout each spot. Any other relative motion of the capillary and the substrate compatible with the condition of spending equal time over each area of deposition on the substrate would also provide uniform deposition and can be determined by those of skill in the art. Another way to uniformly deposit electrosprayed material consists in placing the capillary into a perforated shield/screen as described below. When a single sample of complex shape and uniform thickness is to be deposited (for example, rectangular protein strip), the capillary is preferably stationary and not positioned directly above a non-round hole in a mask while the mask and the substrate/support are being rotated. In this way, the rotating mask and substrate/support bypass the electrostatic focusing effect of the hole by allowing charged particles to approach the hole evenly from each side. As a rule, a guard ring having a potential of the same sign as the charged microdroplets leaving the capillary tip is positioned approximately at the level of the capillary tip to surround the zone of electrospray discharge with a charge that repels the charged microdroplets and prevents any scatter during electrospray. It was discovered that the guard ring can be effectively replaced by plastic screens such as the non-limiting examples of the two types represented schematically on FIGS. 16A and 16B. These plastic screens could be of a conical or cylindrical body. Deposition of a part of the electrosprayed material on the walls of such a body charges them and prevents further scattering. It was also discovered that the walls of such plastic screens can be made of woven plastic tissue permeable to air. This latter design has three advantages: (i) it allows solvent to be easily dried from the electrosprayed material; (ii) it allows confinement of the charged particles in the volume surrounded by the screen, and together with the mutual repulsion of charges, result in even deposition within the area limited by such a screen, as illustrated in FIG. 16C; (iii) a conical grid similar to that shown in FIG. 16A facilitates concentration of particle flow, which is especially important in deposition of microsamples.

The efficiency of deposition with the above described means depends on the quality of screen and mask material as a dielectric (low bulk and surface conductivity are required), tip-substrate distance and the overall area of the holes. With multiple holes, such as those presented in FIG. 5A, or a single round hole with a diameter of 1.5–2 mm, an efficiency of 70–80% is readily obtainable.

Reduction of the hole to 0.2×0.7 mm² results in a decrease of the efficiency to 4–10%. It was found that the introduction of an additional collecting ring of 2–5 mm in diameter coaxially positioned in the plane of the plastic mask allows a considerable increase in the efficiency upon proper adjustment of the potential at the collecting ring. To adjust the potential, the total current passing through the capillary, as well as the current passing through the sample, are measured simultaneously. The procedure is further described assuming that a positive potential is applied to the capillary and the sample holder is grounded on increasing the potential on the collecting ring (from zero, grounded), an increase in sample current is observed, and the current goes through a maximum upon further increase in ring potential and then drops until a complete inhibition of the electrospray occurs. A decrease in the total current through the capillary upon an increase in the ring potential is accompanied by a fading of the intensity of the electrospray torch. It was found that electrospray deposition, under the conditions where the current passing through the sample holder reaches 50–90% of the total current, results in 20–40% efficiency of protein deposition through a single submillimeter-sized hole in the mask. Simultaneous deposition of numerous microsamples is far more effective and does not usually require a collecting ring. However, a dielectric mask with multiple holes can also be covered with a multi-ring collecting net in such a way as to have each hole at the center of the ring, with all the rings connected to a power supply with voltage adjusted, as was described above for a single hole collector.

Another potential problem with deposition through a small hole in a dielectric mask is that the deposition of the sprayed material directly onto the dielectric mask in the vicinity of the hole greatly reduces the overall efficiency. The extent of such deposition onto the mask surface varies depending on both the type of polymer used and on other conditions, such as voltage, charge of the sprayed particles, presence and diameter of the collecting ring. In particular, the laboratory of the present inventors found that the use of mica as a mask material results in less deposition onto the mask surface, presumably due to the lower mobility of injected charges or fewer holes in mica as compared to plastics, where such mobility can be high (Reiser et al., 1969).

The substrates or supports onto which the charged particles are deposited preferably have a high conductivity. However, other materials with low bulk conductivity (semiconductors) or those having small surface conductivity can also be used as substrates. Examples of such materials include paper, hydrophilic plastics and membrane filters (e.g., IMMOBILON-P filters prepared from PVDF, nitrocellulose filters), mica and glass. Mica and glass are nonconducting when dry but have surface conductivity when wet or in a humid atmosphere. Filters are also conductive enough in an atmosphere of high (>70%) and moderate (30–50%) humidity to enable their use as substrates.

Figure 34:
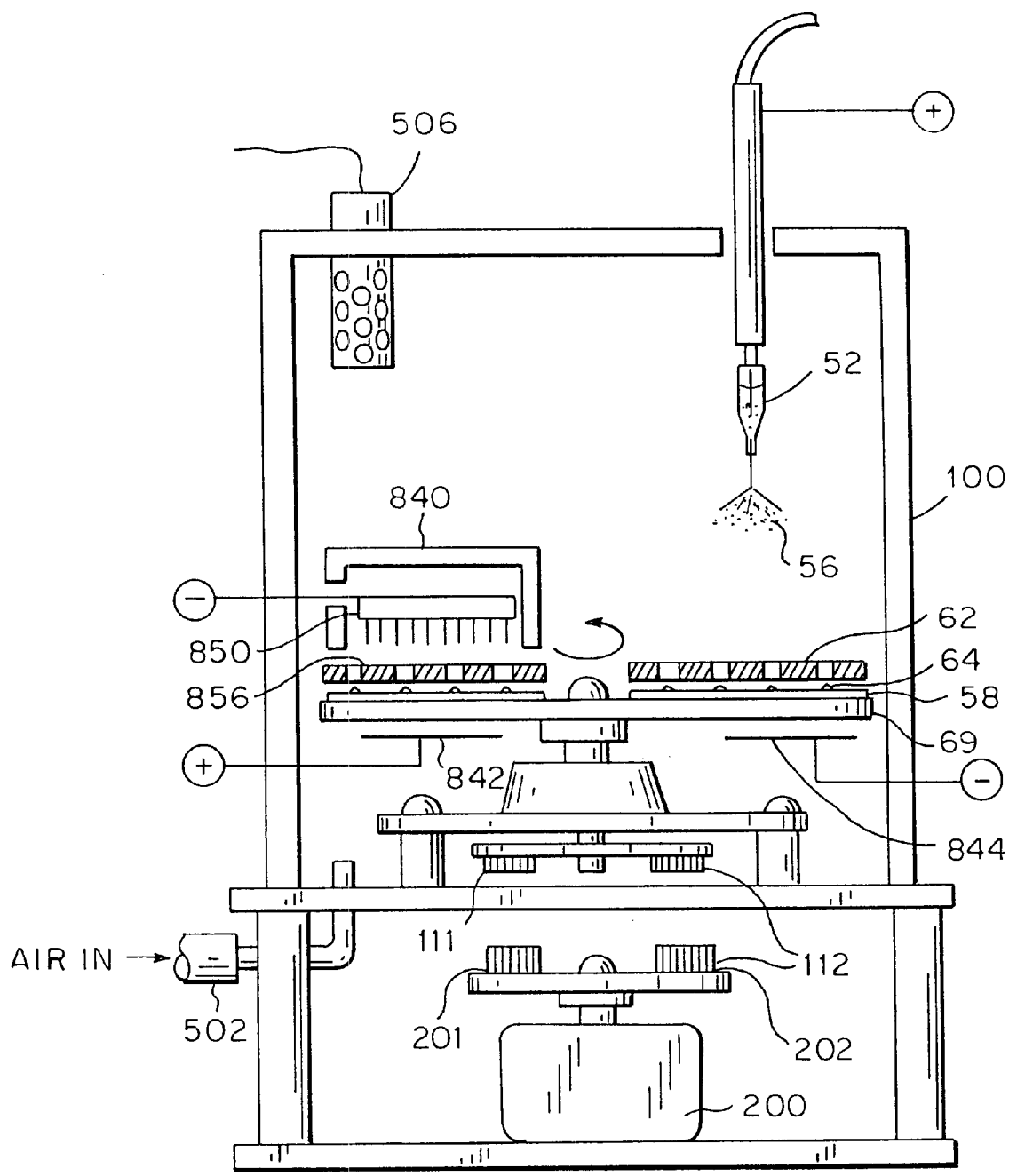
FIG. 34 is a schematic elevational view, similar to FIG. 25, of a third embodiment of the electrospray chamber.

In one embodiment of the method of the present invention, electrospray deposition onto a nonconducting surface in the absence of surface conductivity, such as dry mica and glass, dry plastics, is performed by periodic recharging of the nonconducting surface with a stream of counter-ions from a corona discharge as shown schematically in FIG. 34. The stream of counter-ions is generated with an array of microelectrodes in a shielded chamber. Such recharging provides the advantage that successive layers of charged molecules can be deposited onto the substrate by repeated cycles of spray and recharging; otherwise, a buildup of charged molecules on the substrate would prevent further deposition. In the example of a mica surface, a mica sheet is placed on a rotating plastic disk and periodically recharged during its period of rotation that passes underneath an array of microelectrodes. Either positive or negative voltage can be applied to the capillary with respect to the mica. To reduce the surface conductivity of the mica in this embodiment, the mica surface can be kept dry during deposition by heating with an infrared source or with a stream of dry warm air. Deposition can be performed for example in open air or in a chamber with a controlled atmosphere.

Figure 6:
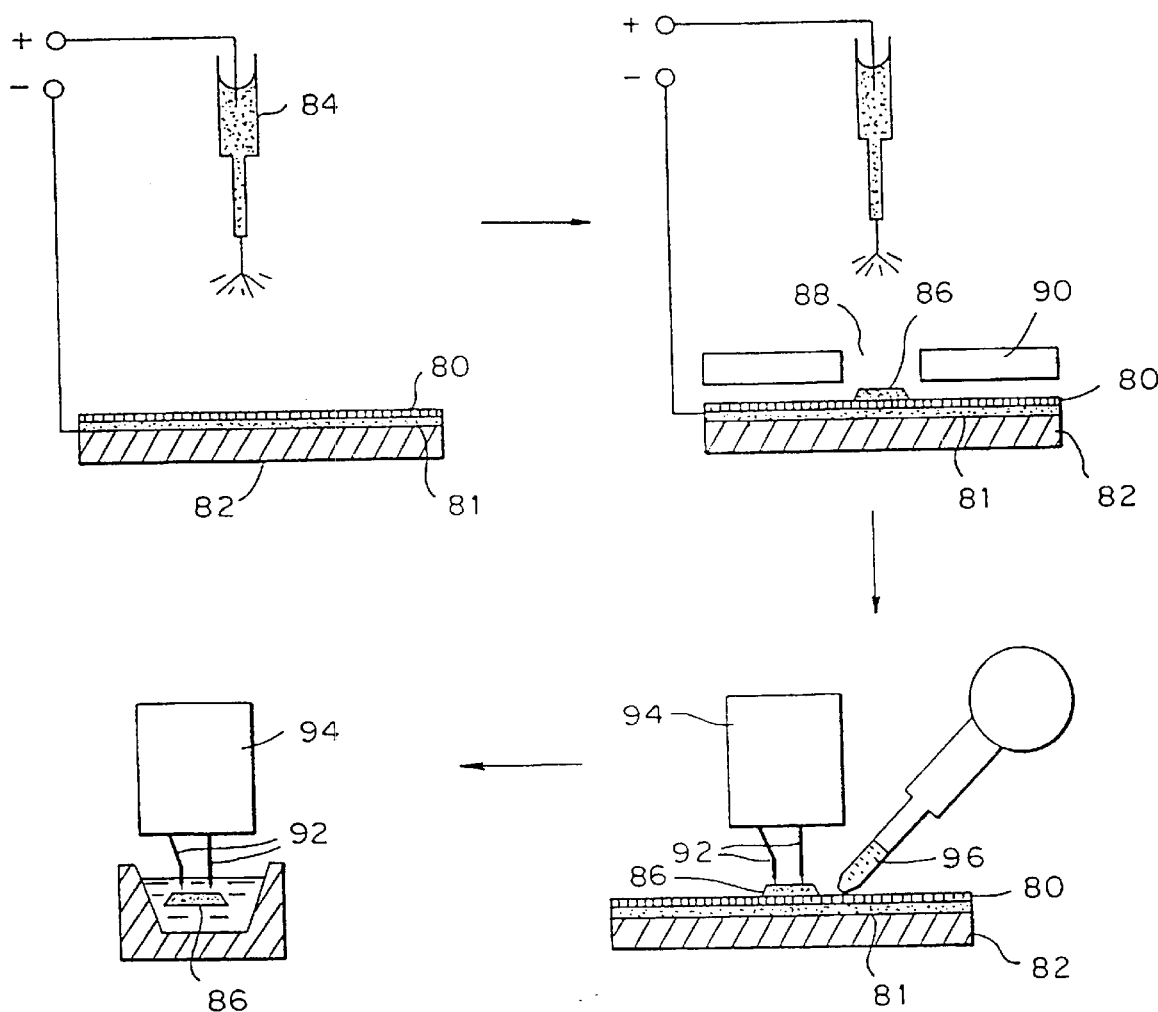
FIG. 6 is a schematic of a process for the fabrication and detachment of a sample film.
Figure 7:
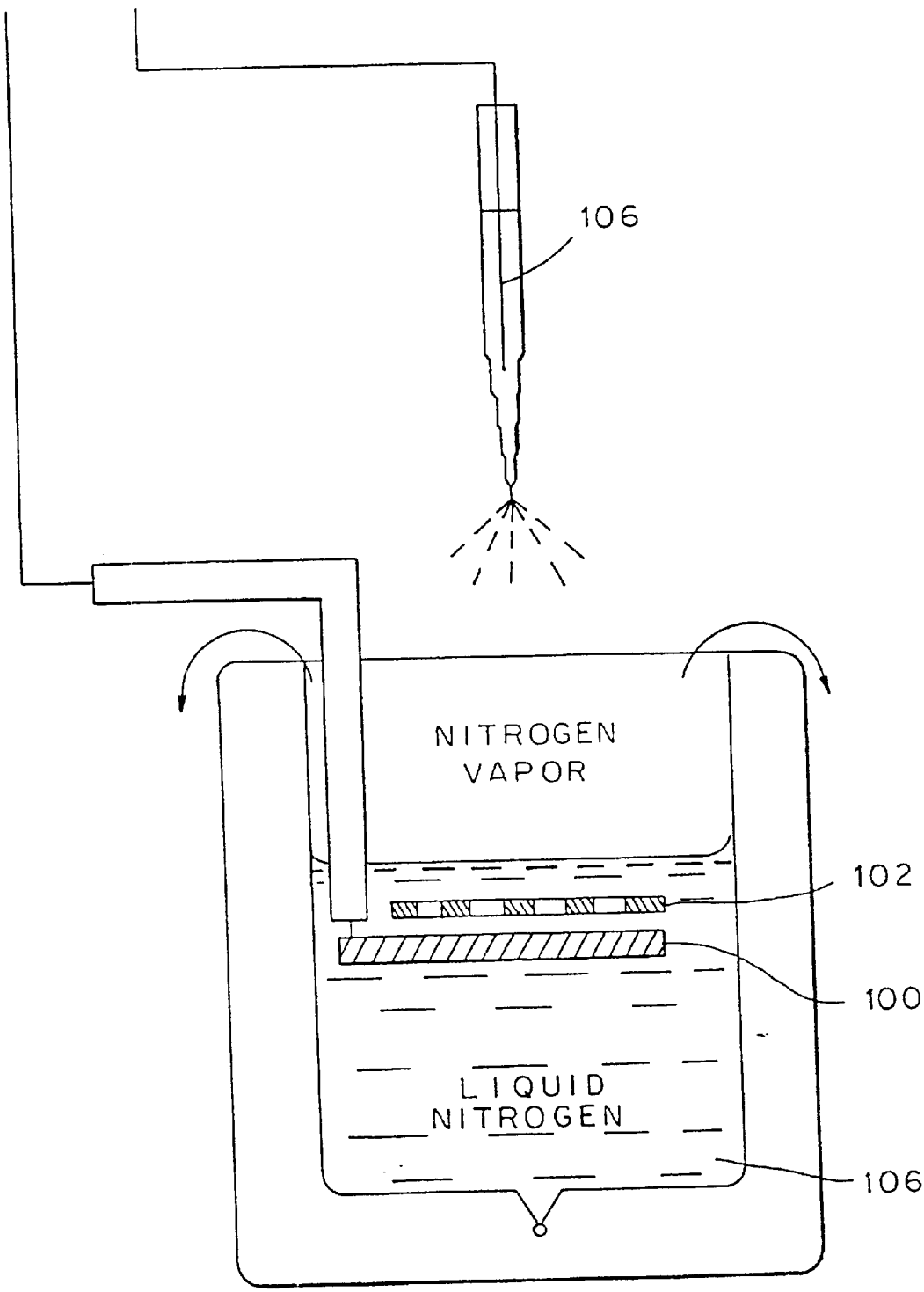
FIG. 7 schematically shows electrospray deposition onto a substrate cooled with liquid nitrogen.

In certain circumstances, the detachment of the deposited material from the substrate or support as a sample film is desirable, and an intermediate layer between the substrate and the sample can be introduced to facilitate this detachment, i.e., for transfer to a measuring device using such a sample film. Such an intermediate layer must be slightly conductive and must be easily removable after cross-linking of the electrospray-deposited biomolecules. Examples of materials which can be used as an intermediate layer include: (1) a water-soluble polymer layer, such as polyacrylamide or polyethylene glycol which slowly swells and dissolves in the presence of water and/or other conditions, i.e., variation of pH; (2) a layer of a commercially available polymer having disulfide bonds which can be broken (chemically reduced) when in contact with a mercaptoethanol solution, thereby resulting in dissolution of the polymer; (3) a layer of highly dispersed carbon with low adherence to the deposited biomolecules; and (4) a layer of carbon-polymer conducting composites or any other conducting polymer with a low melting point. FIG. 6 schematically illustrates an embodiment of a process for the fabrication of a sample film on an intermediate layer and the detachment therefrom. A semiconductive sublayer 80 as an intermediate layer is first deposited over a conductive substrate layer 81 on the substrate 82 by electrospray with a capillary 84 or by any other known methods, and then a sample film 86 of the desired biomolecule(s) is deposited by electrospray through a hole 88 in a mask 9D. The sample film can be attached to the tips 92 of a measuring device 94 and detached from the substrate by dissolving the semiconductive sublayer with a solvent 96. Alternatively, the sample can be simply lifted off the substrate as a detached film. A preferred intermediate layer for the detachment of the sample film is a sublayer of alginic acid which is insoluble to solutions with an acidic pH but can be readily dissolved with a solution at an alkaline pH.

Using protein as an example of a biomolecule for electrospray deposition, the structure of the protein film and the functional properties of the protein molecules in the film is dependent on the path of flight of the electrospray, speed of the charged particles controlled by voltage, sign of the charges, humidity and temperature under which the protein molecules are electrosprayed, protein concentration in solution, and presence of stabilizers. At short distances, e.g., about 15 mm between capillary and substrate, or when the electrospray takes place in a humid atmosphere (relative humidity of more than 70–80%), charged microdroplets from the electrospray can reach the surface without decay or the production of dry ions, i.e., in the wet electrospray regime. The sample films obtained after evaporation of the deposited microdroplets on the substrate have much in common with the sample protein films obtained conventionally by applying a protein solution directly to the substrate and allowing the proteins to dry. No notable difference in the mechanochemical response to ligands, such as $Ca^{2+}$, was detected between films of α-lactalbumin, which were prepared by wet electrospray deposition onto a glass surface covered with a conducting $SnO_2$ layer and films of the same enzymes prepared by the conventional method.

The electrospray deposition of biomolecules can also be used as a means of concentrating microquantities of dilute biomolecule solutions. By changing electrospray conditions (humidity below 40–50%, capillary-to-substrate distance of more than 30 mm, flow of dry gas), deposition is performed in the dry regime where the concentration of biomolecules in microdroplets occurs, and dry nanoclusters and biomolecular ions are deposited onto the substrate. As revealed by scanning atomic force and tunneling microscopy, biomacromolecules are deposited as single dry molecules only if their concentration in solution is below a critical threshold of about $10^{-3}$–$10^{-5}$ mg/ml. At higher concentrations and in the dry electrospray regime, nanoclusters, which are the dominant products of electrospray, form opaque porous films, as illustrated in FIG. 15A.

Protein molecules in the films prepared by dry electrospray retain their functional activity. The data presented in Table 1 indicate that electrospray-fabricated microsamples of different proteins show the same level of the mechanochemical response to specific ligands as the films of these proteins prepared by the conventional drying method. Retention of other functional properties of protein molecules in electrospray deposition is illustrated in Example 3, as well as in FIGS. 12A, 12B and 18, for the enzyme activity of horseradish peroxidase and alkaline phosphatase. Example 4 illustrates the retention of the antigenic properties of electrosprayed proteins.

TABLE 1

Comparison of the Mechano-Chemical Effects to the Application of a Specific Ligand to Films of Different Cross-Linked Proteins Prepared by Electrospraying and by the Conventional Method of Drying Protein Soluutions on a Glass Surface

| PROTEIN | LIGAND[1] | Effect[2] in Dried Sample % | Effect[2] in Electrospray Deposit Sample % |
|---|---|---|---|
| Pancreatic | Proflavin | +69 | +72; +72 |
| Trypsin | BAEE | +23 | +37; +38 |
| Avidin | Biotin | −51 | −41; −48 |
| Cytochrome C (equine) | Reduction with dithionite | −30; −50 | −41; −49 |
| Lysozyme (egg) | N-acetyl-D-glucosamine | −7.7; −8.7 | −6.3; −3.5 |
| Hexokinase (yeast) | Glucose | +31; +38; +44 | +44 |
| Alcohol dehydrogenase (horse liver) | NAD | +3.5; +6.2 | +2.7; +7.4 |
| α-Lactalburnin | $Ca^{+2}$ | +240 | +370 |
| Concanavalin A | $Ca^{+2}$, $Mn^{+2,}$ | +10 | +6 |
| | α-D-mannopyranoside | +11 | +4 |
| Pancreatic RNAse | 3'-Cytidine monophosphate | +4.0 | −3.4 |
| 3-phosphoglycerate kinase (yeast) | Mg-ATP | +13 | +16 |

[1]Ligand concentration in each testing exceeded known binding constant by 5–10 times.
[2]Relative changes in isometric tension in protein film induced by binding of specific ligand are presented.

Although the best conditions for protein deposition may vary from protein to protein, it was found that the following conditions give satisfactory results with most water-soluble proteins: 1–10 mg/ml protein concentration; 25–40% (w/w of dry protein) sugar or trehalose; 10–15% glycerol based on dry protein; and 100–20 mM β-mercaptoethanol. The conductivity of protein solutions prepared for electrospraying should not exceed 500 microSiemens per cm, otherwise deposition proceeds very slowly and requires the use of capillaries with micron-sized tips. The pH usually does not require adjustment unless it is incompatible with the stability of protein molecules. β-mercaptoethanol should be added immediately before spraying. The following spraying conditions can be considered as typical for the fabrication of a single protein microsample for the mechanochemical test: room temperature; 10–40% relative humidity; height of the capillary tip above the sample holder: 10–14 mm; voltage on the capillary: +2–3 kV; voltage on the collimating ring: +(0.5–1.5) kV; current total: 5–10 nA; current through the sample: 3–7 nA; total time to deposit one 1–2 micron thick protein film with 0.2×0.7 mm lateral side measurements takes 3–15 minutes, depending upon protein concentration.

Of all the parameters, the maintenance of a low total current through the capillary seems to be the most important. As illustrated in FIGS. 18A and 18B, an increase in the current by more than 10–100 nA considerably inhibits the specific activity of alkaline phosphatase. Low current is also beneficial from the viewpoint of efficiency. Excessive space charge formed around the hole in the screen at a high current repels charged clusters from the hole and increases their deposition on the screen and collimator.

Conditions for electrospray fabrication of multicomponent tests may differ significantly from that described above since higher currents, together with high flow rates, can be used without the loss of activity and efficiency. Other conditions which may greatly vary upon deposition of matrices include solvents (for example, addition of 10–30% of glycerol to protein or DNA solutions enables their wet deposition onto a porous filter even at low humidity and large substrate-to-capillary distance), concentration, temperature, humidity and substrates.

Besides the faster drying achieved in dry electrospray, which helps protect proteins from damage, addition of protective reagents, such as trehalose, sucrose, other carbohydrates, and other polyols, also serve to provide protection against damage and/or inactivation upon drying. When electrosprayed under mild conditions of low voltage/current and controlled humidity, the presence of sucrose protected the activity of alkaline phosphatase (AP) relative to AP directly dried onto the same substrate from the same solution used for electrospray. The specific activity of the AP enzyme deposited by electrospray under mild conditions was found to be similar to that of the initial enzyme solution. Radical scavengers and antioxidants can be added as protective reagents to protect against damage from radicals, atomic oxygen and other active species produced during the electrospray process. For proteins with free SH- groups that are essential for their functional properties, such as in hexokinase, the presence of β-mercaptoethanol, a reducing agent which protects the oxidation of SH- (sulfhydryl) groups in the electrospray solution, was found to result in a considerably better retention of functional properties as judged from an increase in the mechanochemical response of the electrospray-deposited protein film upon binding of specific ligands. β-mercaptoethanol can also act as a radical scavenger and antioxidant, and thus, its addition is useful even with proteins lacking the sulfhydryl groups.

In addition to protecting biomolecules against damage during drying in the method of the present invention, protective reagents, such as the carbohydrates and polyols, e.g., glycerol, sucrose, trehalose, etc., can also serve to decrease the packing density of biomolecules, particularly proteins, in the deposited sample films. These protective reagent additives are water-soluble and non-volatile. After the biomolecules in a dry state are cross-linked, the water-soluble non-volatile additives can be washed away and thereby create additional voids and channels in the sample, thus lowering the packing density in the cross-linked sample film and enhancing the penetrability of the sample film to ligands. Such films can be more effective in tests with specific ligands of larger molecular weight and size.

Figure 15A:
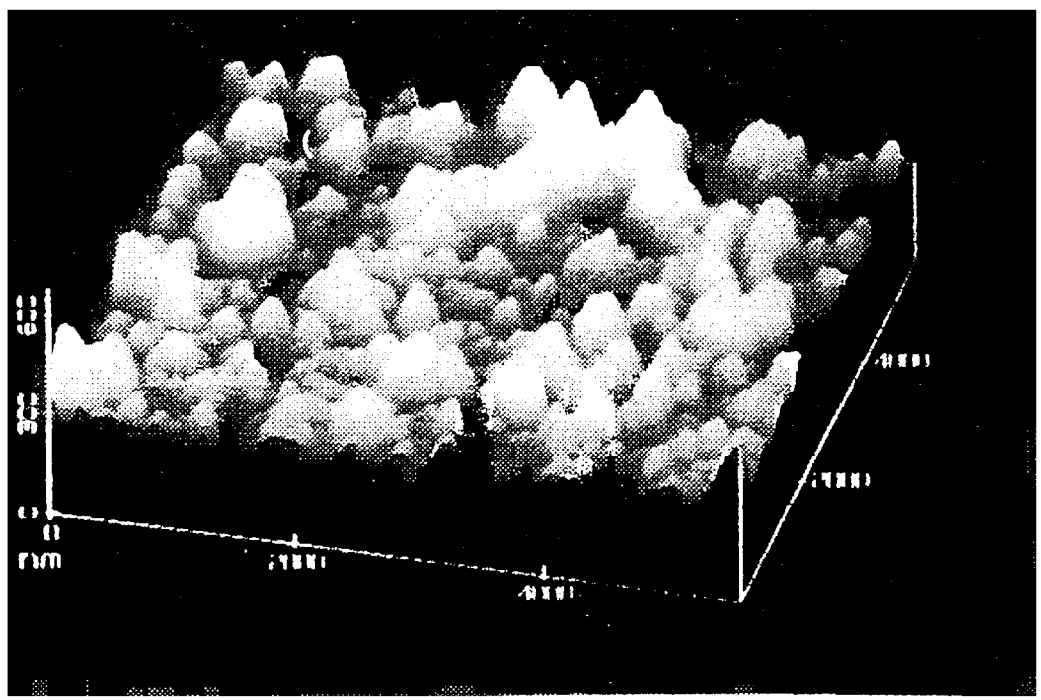
FIGS. 15A–15C show the porous structure of the electrospray-deposited film of human hemoglobin (image of film surface made by scanning force microscope after dry deposition in FIG. 15A), changes in film structure as a result of film "baking" (image in FIG. 15B presents the structure of the same film after exposure to wet atmosphere), and a graph demonstrating the considerable enhancement in penetrability of electrospray deposited film of bovine serum albumin as compared to a film obtained by a conventional method of drying protein solution (FIG. 15C).
Figure 15B:
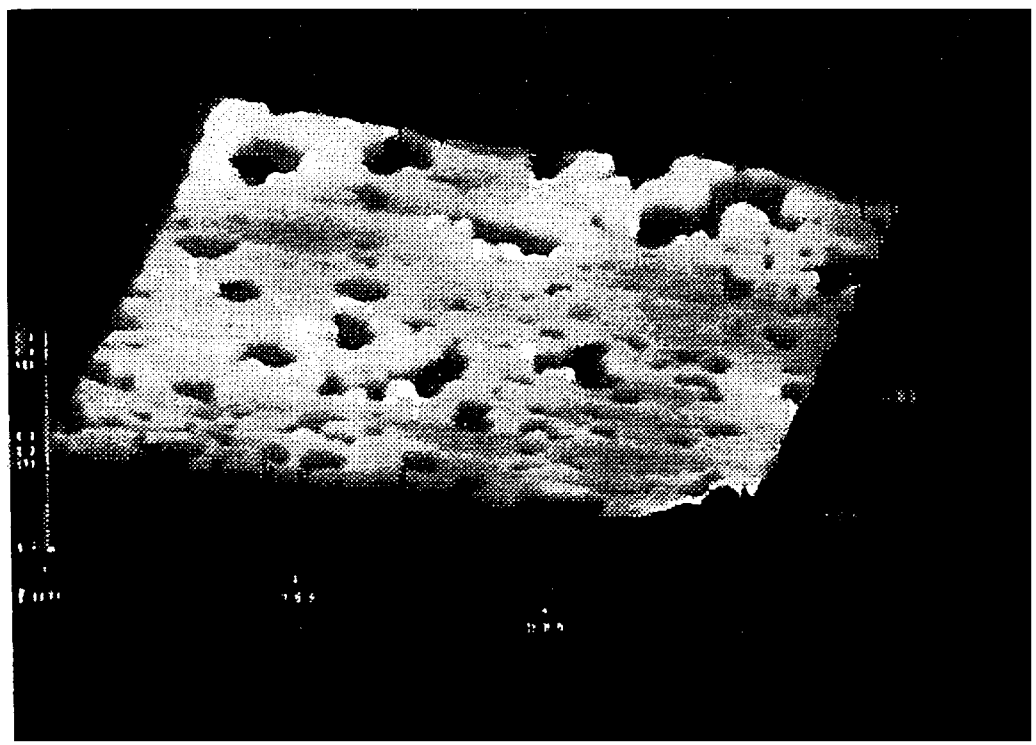
Figure 15C:
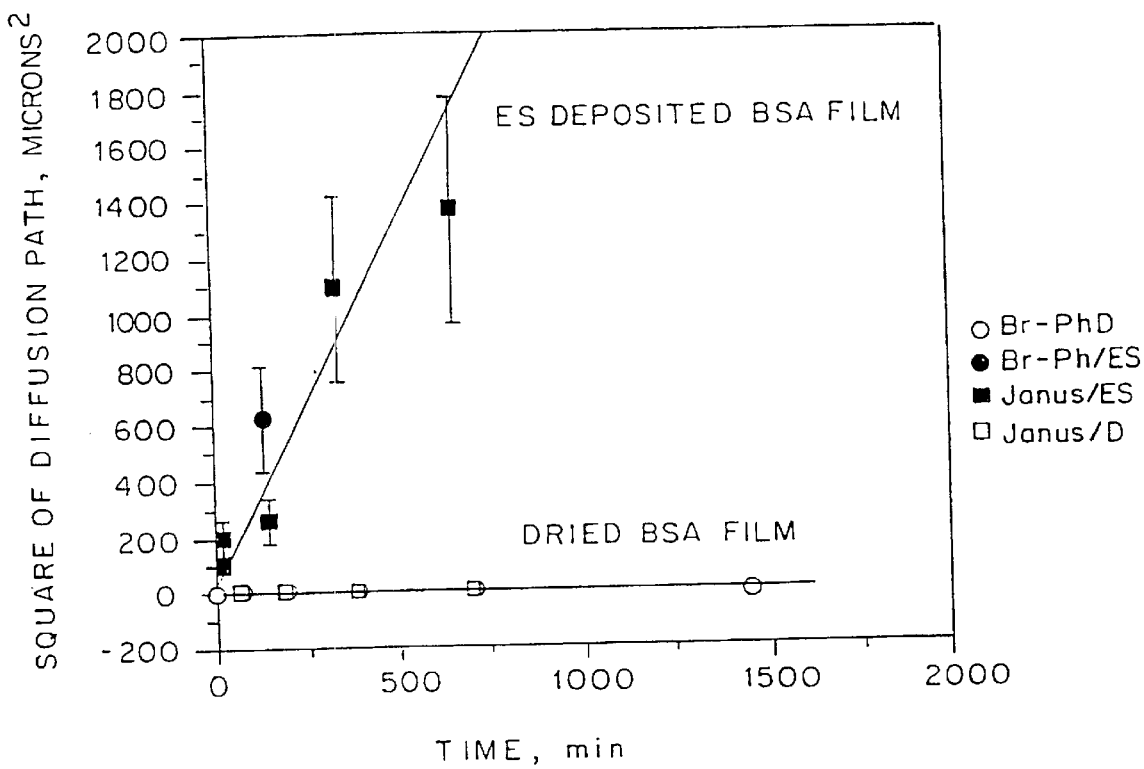
Figure 16A:
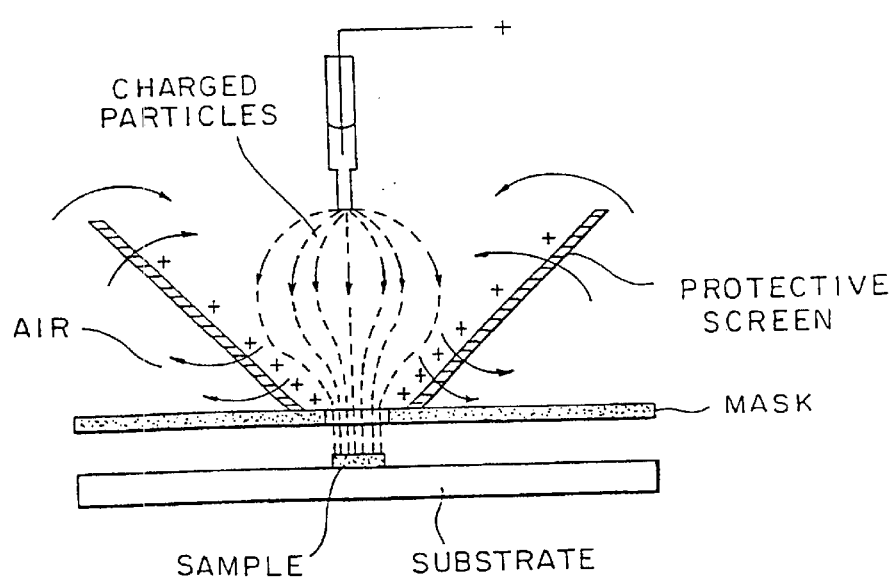
FIGS. 16A–16C schematically present two types of plastic protective screens used to prevent escape of the electrosprayed material from the target substrate and show the uniform distribution of electrodeposited material.
Figure 16B:
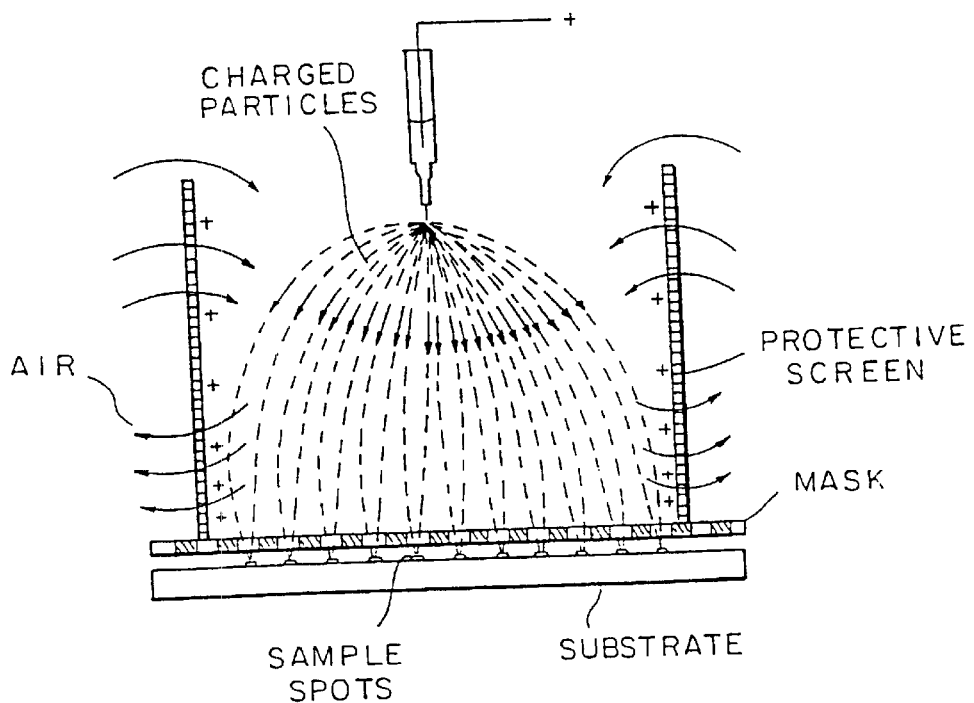
Figure 16C:
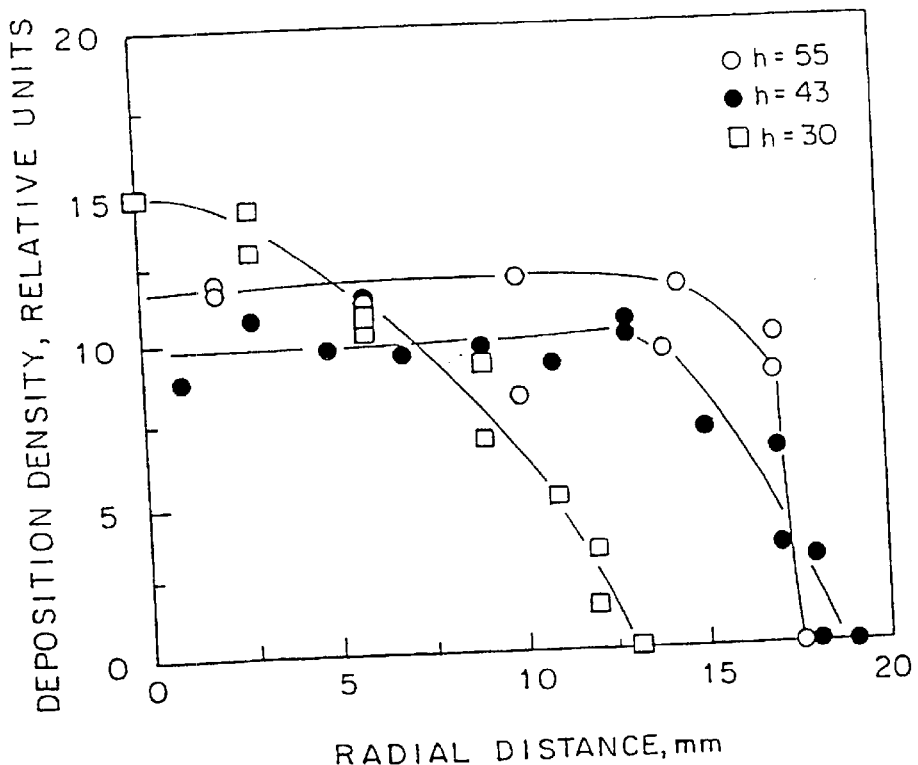
Figure 17:
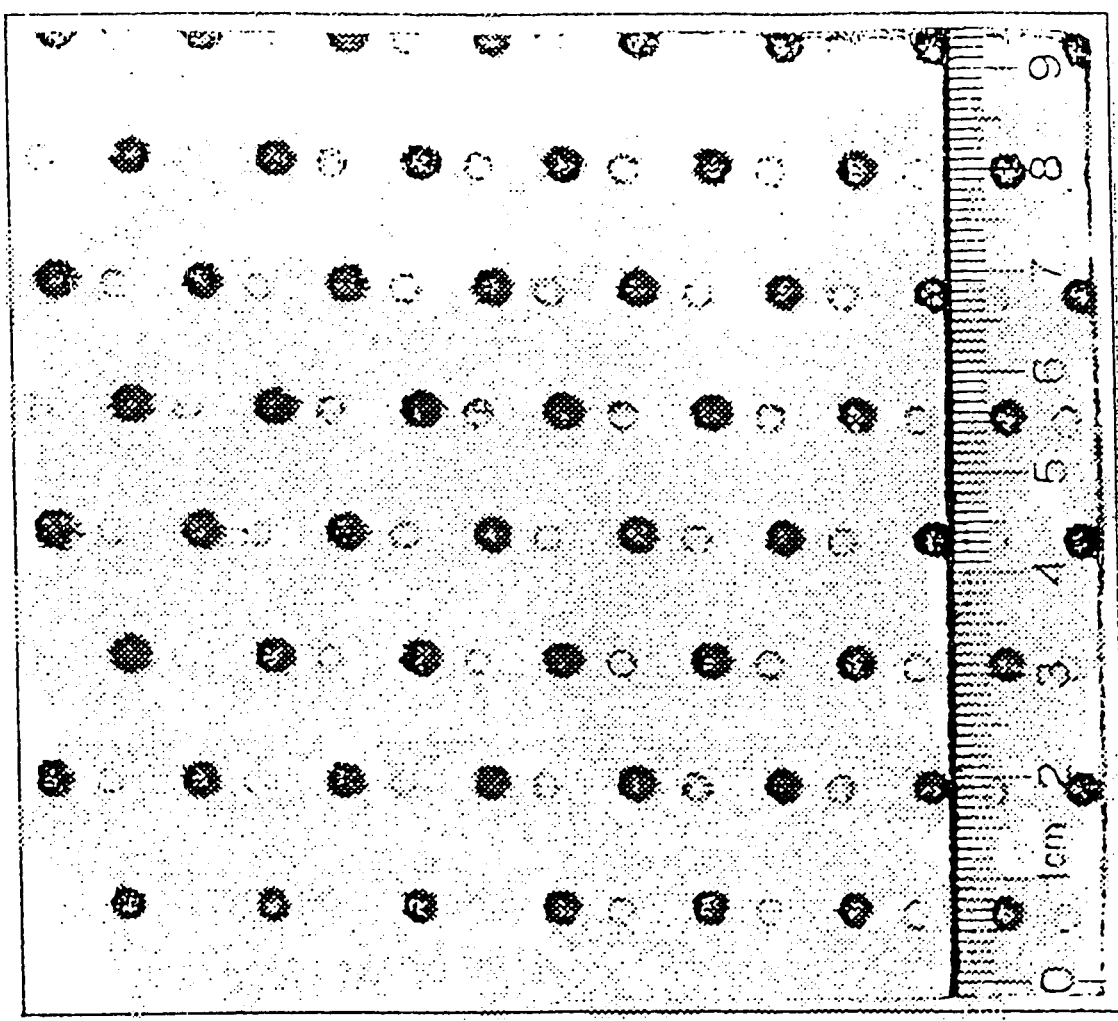

Another way of decreasing the packing density and enhancing the penetrability of a biomolecule sample film is to use dry electrospray with high concentrations of biomolecules in solution, which results in the deposition of biomolecules in the form of nanoclusters. The size of the deposited nanoclusters strongly depends on the biomolecule and solute concentrations. The internal diffusion in such films composed of the electrospray-deposited nanoclusters is much faster than in dried film of the same protein, as illustrated in FIG. 15C, since the large intergrain channels are easily penetrable by ligands, and only the diffusion within the grains will be slowed down to the level of a homogeneous film.

While it is expected that large ligands can also penetrate sample films having a low packing density as described above, the reduction of the thickness of the deposited biomolecule film layer is thought to be the main route to decreasing the diffusional limitations in the sample film. A monolayer of biomolecules, free or deposited onto a suitable material can be considered as a limiting case of such a thin film which is completely free of any internal diffusion limitations. To be used in mechanical tests, such a film can be internally cross-linked and used free or deposited onto the surface of a gel which does not restrict the mobility of the monolayer film. In other assays (e.g., for use in plasmon resonance sensors, in immunoassay tests, etc.), a monolayer film or even separate molecules can be deposited by electrospray on any suitable material within the knowledge of those in the art and used with or without cross-linking.

Agents that are available for cross-linking biomolecules together are well-known to those of skill in the art (Hermanson et al., 1991). UV irradiation can be used for DNA molecules. For protein molecules, glutaraldehyde is preferred because it has advantages in terms of preserving the functional activity of cross-linked proteins. Glutaraldehyde attacks free amino groups, which are numerous in protein molecules, and their modification does not appear to adversely affect the functional properties of proteins unless the amino groups are directly involved at an active site. While the amino groups at active sites can be protected from reaction with glutaraldehyde by the steps of reversible maleilation at basic pH, cross-linking under basic pH, and deblocking by storage at slightly acid pH (pH 5–6), the laboratory of the present inventors has found that ligand binding, as determined by affinity assays performed on this film, was still detectable even if the amino groups were left unprotected in proteins which have amino groups in their active sites, i.e., ribonuclease, monoclonal antibodies, etc. It is useful, however, to protect the amino groups when the protein has either numerous free amino groups or amino groups in a binding site so as to obtain a larger signal-to-noise ratio.

Before the cross-linking of the deposited biomolecules, and in particular proteins, the film of biomolecules may be exposed to either a humid atmosphere or a solution, i.e., a glycerol solution, which allows for limited mobility or liquidity of the biomolecules in the sample film but not for solubility in the solution. The effect of increased liquidity allows the protein molecules and/or clusters in the film to move relative to each other, filling voids inside the film and providing a film with no visible inhomogeneity. This phenomena can be likened to transformation in a layer of big round rocks that were haphazardly dumped onto a surface. If the big rocks are allowed to move relative to one another due to some form of disturbance, then the big rocks would preferably move to a more uniform topography. A homogeneous film of proteins however provides strength at the expense of possibly reduced ligand penetrability.

The advantages that the method of the present invention has over known methods of depositing multiple spots include those listed below.

As compared with methods of direct application of spots (dots) of substances manually or with the use of computer controlled manipulators (like those used in Stanford University to fabricate DNA libraries, see Shalon et al., 1996):

(i) considerably smaller spots can be deposited;

(ii) spots are deposited simultaneously, which potentially greatly reduces the fabrication time;

(iii) spots can be of any shape;

(iv) when deposited on a filter membrane, substances are not distributed over the whole thickness of the membrane but are concentrated in the surface layer, which facilitates the discovery of spots by optical methods.

As compared to methods using electrodeposition from solution, electrospray deposition is advantageous, since (i) no microelectrode arrays are required to deposit the microsample, (ii) even slightly conducting surfaces may be used as support. For example, the surface conductivity of mica and glass in a humid atmosphere is enough to deposit substances onto a surface. FIG. 5C presents an example of electrospray deposition through the screen shown in FIG. 5A onto a wet mica surface.

(iii) sequential deposition of a different substance is not connected with cross-contamination of spots of different substances as it may occur when in contact with solution.

As compared to photolithographic techniques electrospray deposition is advantageous in:

(i) reduction of number of steps in deposition procedure;

(ii) diminution of cross-contamination due to absence of the contact of the whole chip surface with each solution;

(iii) reduction of cross-contamination due to a smaller number of chip transfers through the solution interface when it is dipped or withdrawn from the solution.

Special advantages of the electrospray deposition technology include:

(i) Electrospray allows deposition under conditions that cannot be attained by conventional methods, e.g., substances can be deposited onto a surface cooled to a very low temperature, i.e., under liquid nitrogen or a dielectric fluid, as shown schematically in FIG. 7. These low temperature conditions might be useful in depositing unstable molecules. Electrospray deposition also allows for deposition under vacuum. Charged molecules and clusters can be introduced under vacuum in a manner similar to that used to introduce ions into mass spectrometry. Substances can also be separated before deposition, for example, by placing the substrate behind the slot in a mass-spectrometer, where separate components of the electrospray solution can be deposited in different positions on the substrate, enabling further use of the deposits in chemical analysis.

(ii) Unusual internal structure of electrospray-deposited substances may be obtained. For example, an amorphous protein film obtained by electrospray may not be as densely packed and as homogeneous as those films obtained by drying a protein solution on a surface. Instead, a porous material formed of protein clusters was obtained by the electrospray deposition of concentrated protein solutions as shown in FIG. 15A. Such porous films provide advantages in analytical applications by facilitating penetration of substances into such films.

(iii) The amount of deposited substance is easy to control, since essentially all the electrosprayed material goes onto the substrate. This is not the case in the deposition of a film of biomolecules from solution, where the efficiency with which different molecules bind to the activated surface may be different.

(iv) Electrospray deposition is highly economical since practically all the electrosprayed molecules reach the substrate surface through the holes in the mask.

(v) Electrospray deposition is very flexible with respect to size of deposits. It can be applied to deposit not only spots as small as 1 micron but spots as large as 1 cm or more, using similar techniques.

The method according to the present invention can be used to fabricate sensitive elements of biosensors from very small quantities of proteins (0.01–1 microgram). This is especially important when applied to a mechanochemical method of testing the biospecificity of protein molecules by change s in the properties of a protein film, since microgram quantities of proteins are usually readily available from common analytical scale protein purification procedures, such as electrophoresis. The method can also be used to prepare protein sample for other types of biosensors, e.g., enzyme electrodes, MOSFET chemosensors, biosensors based on changes in mass or in the optical properties of the protein, etc. In general, the method of the present invention for fabrication of microsamples from biospecific molecules offers a new way of combining the biospecificity of natural biological molecules with the capabilities of signal treatment and the small size of modern integral electronic chips.

An example of the preparation of such a sample film is presented in FIG. 6, where the electrospray deposition is used to obtain a single sample film of immobilized protein for mechanochemical testing of protein bioaffinity. The method according to the present invention enables the fabrication of protein samples from submicrogram amounts of protein dissolved in a few microliters of water. To allow easy detachment of the sample, a sublayer, as shown in FIG. 6, is predeposited on a conductive substrate.

Direct binding detection methods using the sample film deposit include plasmon resonance (i.e., elliptical reflectance microscope, which is commercially available) and scanning probe microscopy (force microscope may be used to discover the binding of ligands-to an array of large protein molecules on a substrate surface, whereas tunneling microscopy may be used in the detection of binding of DNA probes to complementary oligonucleotides present in matrices on a substrate surface).

Figure 8:
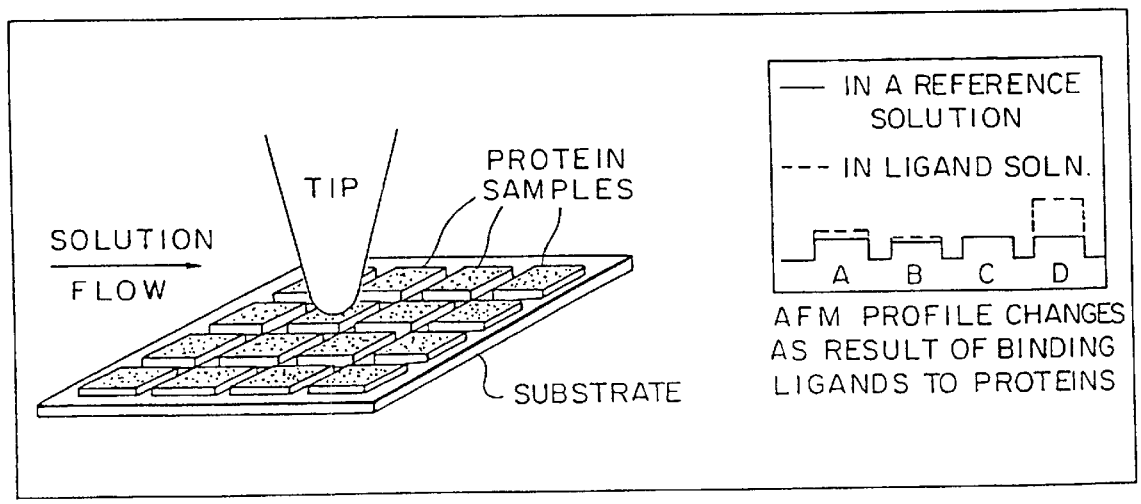
FIG. 8 schematically illustrates the use of scanning/atomic force microscopy in detecting ligand binding to a matrix of protein spots by measuring the changes in the size and elasticity of these protein spots as a result of ligand binding.
Figure 10A:
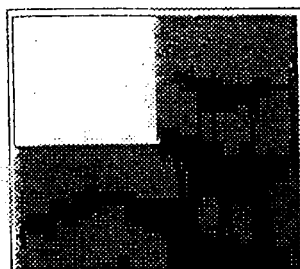
FIGS. 10A–10F show a succession of six masks used to fabricate a combinatorial library of a 6-mer oligonucleotide. The white areas represent holes in the mask.
Figure 10B:
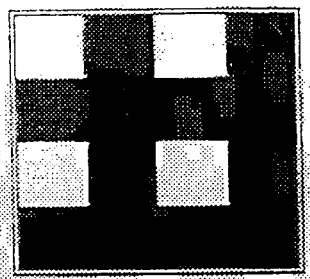
Figure 10C:
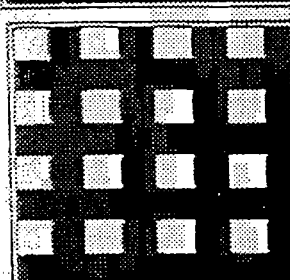
Figure 10D:
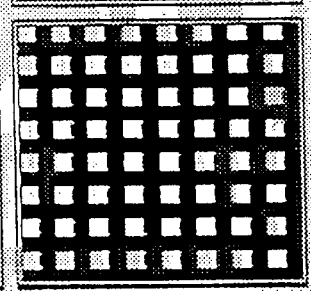
Figure 10E:
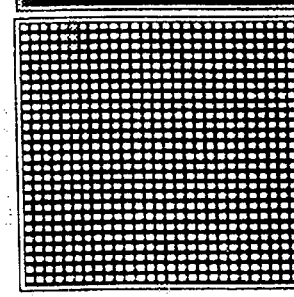
Figure 10F:
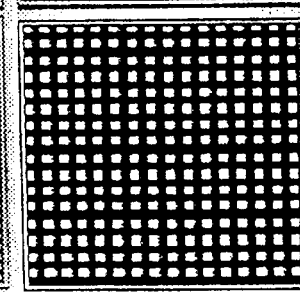

The method according to the present invention provides the means for greatly reducing the size of the samples needed in all these methods as well as for making multicomponent samples. For example, scanning probe microscopy can be used as a method for discovering the interaction of analytes with protein or other molecules deposited as matrix elements on a substrate surface. One such scheme is shown in FIG. 8. A scanning force microscope (SFM)/atomic force microscope (AFM) can measure the height and elasticity of each spot in the matrix. Thus, in the analysis of large analytes (i.e., proteins, DNA molecules), SFM/AFM can be directly used to discover analyte binding by an increase in the thickness of a protein monolayer, like in the methods using plasmon resonance and mass changes. With small analytes, the mechanochemical effects in the protein deposits may be exploited. As shown in the right side of FIG. 8, each spot (deposit) in the matrix swells and changes its elastic modulus differently upon contact with analyte solution. The responses of different elements having different specificities will allow analysis of complex multicomponent solutions.

Figure 33:
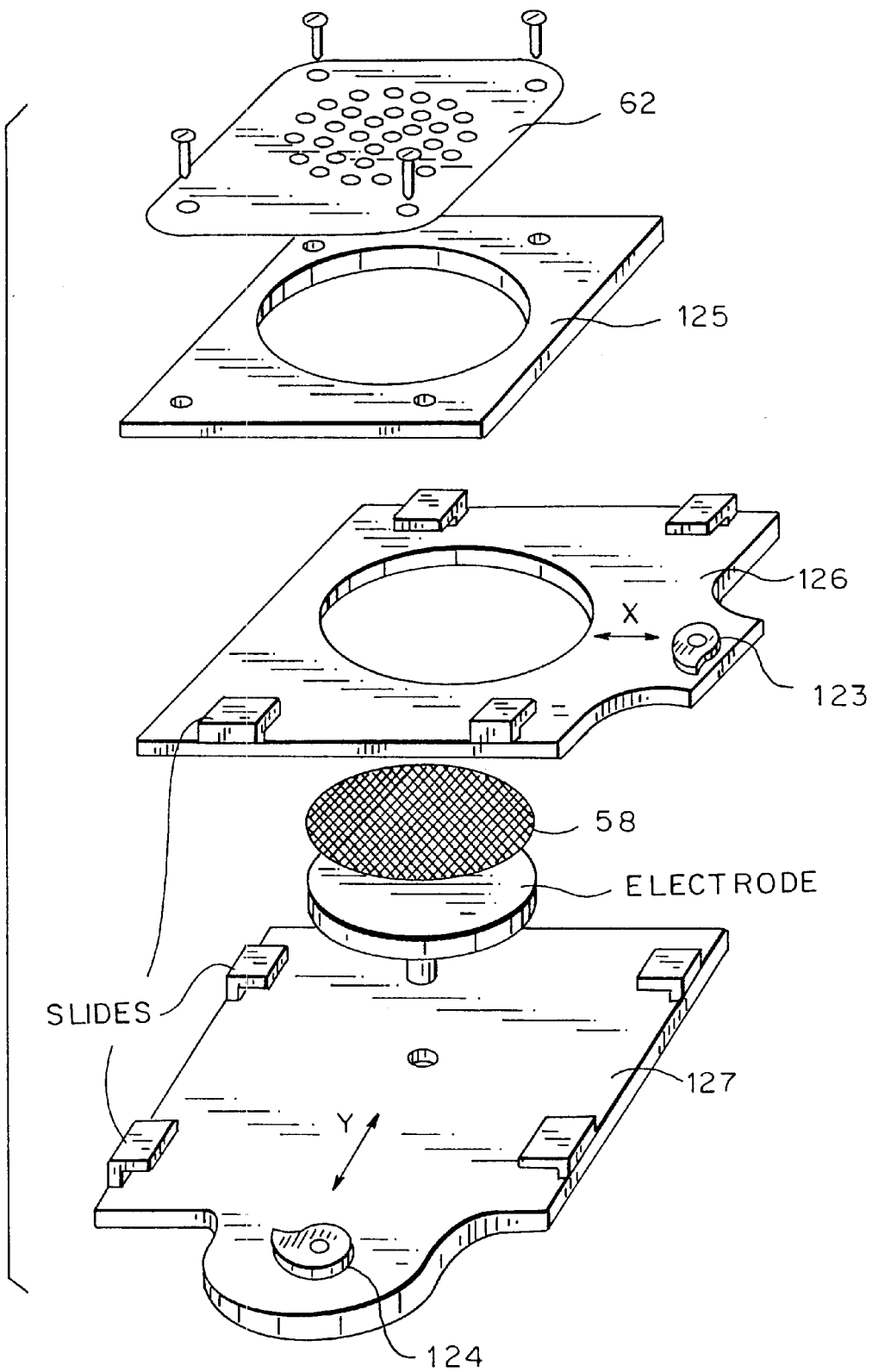
FIG. 33 is an exploded perspective view of a mask shifter.

The mass fabrication of patterns and matrices of different substances on a substrate is achieved by displacing a multi-hole dielectric mask or a photo-mask over a specified distance after the deposition of each particular substance. The displacement is preferably smaller than the distance (spacing) between holes in the screen. In this way, a pattern of spots can be formed in an array of multicomponent matrices. As shown in FIG. 9, either the mask or substrate is shifted by an XY scanner after each deposition of a different solution so that single spots of multicomponent matrices are fabricated under each hole of the mask simultaneously. While solutions A through E in separate capillaries for depositing different spots are shown in FIG. 9, the same equipment can also be used to produce a large number of monocomponent samples simultaneously. For instance, a pattern of 200,000 spots is deposited in this manner over the area of a standard postage stamp (approximately 2 cm×2 cm) by electrofocusing the electrospray through the holes of the mask. FIGS. 32 and 33 illustrate two types of devices for relative displacements of substrate and mask. In FIG. 32, the substrate is attached to a moveable stage, and in FIG. 33, the mask is attached to a pair of plates, each capable of moving within slides.

Thus the method according to the present invention provides for the simultaneous fabrication of thousands of protein and DNA samples for chemical tests without using much of a valuable or difficult-to-obtain material since every electrosprayed spot (deposit) can be made from as little as $10^{-10}$–$10^{-17}$ g of material. Electrospray can also be used to prepare microscale modifications of existing immunoenzyme methods. For example, antigen X can be distributed over several thousands spots on a substrate capable of producing covalent or other strong binding. After washing off excess antigen, each spot can be used to discover the presence of antibodies to the antigen X in blood serum. Bound antibodies can be detected either indirectly with an enzyme-labeled anti-antibody or directly. A direct method capable of detecting changes in amount of protein material in the spot region, such as scanning force microscopy, plasmon resonance, can be used. When bound antibodies are detected indirectly, an enzyme reaction which results in colored, chemiluminescent or fluorescent insoluble products may be effectively used. Simple estimates show that a spot 10×10 microns in size can be measured in an optical microscope with only $10^4$–$10^5$ antibody molecules in each spot. Thus, $10^8$–$10^9$ sensitive elements can be made from 1 microgram of antibody. Another advantage of the method is the acceleration of the analysis since the diffusion limitations upon binding and washing may be greatly reduced for small samples due to the much thinner unstirred layers around small bodies relative to large bodies.

Furthermore, the present method can be used to fabricate multicomponent matrices, i.e., arrays of spots of different proteins, DNA, and other molecules spatially distributed in a certain way over a substrate, to detect binding, such as with arrays of different antigens patterned on a substrate. The array of spots of different proteins provides a multicomponent analysis of complex mixtures, biological liquids and natural extracts, etc. It is well understood in chemical analysis that the ability to simultaneously register responses of different sensors with different specificities greatly reduces the requirements for specificity and stability.

Microfabrication of multianalyte tests for immunoassay analysis is another example of using electrospray to modify the existing methods. In a modern version of this method, a sandwich of an antigen-antibody-labeled anti-antibody is observed on the surface of a plastic vial as visualized by the colored, fluorescent or luminescent products of an enzyme reaction. One version of a micro modified ELISA, according to the present invention, has arrays of different antigens arranged on a substrate, where each antigen at its specific position is determined by its address on the substrate. If the antibody to the second antigen is present in the solution, then a matrix element will be labeled with an anti-antibody conjugated with an enzyme and readily visualized after the addition of an enzyme substrate, resulting in an insoluble colored or fluorescent product. Such multi-antigen matrices allow for the simultaneous identification of many antibodies in biological liquids in a single analysis, the identification of allergens, a screening to check a patient's immunity against a large number of microbial and virus infectious agents, etc.

In yet another application, the method according to the present invention can be used in the fabrication of samples for the simultaneous hybridization of multiple DNA probes. Matrices of spots from different oligonucleotides and DNA fragments may be prepared on glass, filter or any other suitable surface and used in a conventional way (Hames et al., 1987), such as in the routine identification of biological species, tissue immunotolerance, genetic analysis and other applications of the dot blot technique. It has been demonstrated that molecules of λ-DNA electrosprayed onto glass or nylon filter retain their ability to hybridize biotin-labeled λ-DNA probes, as it is described in Examples 7 and 8.

Multicomponent samples can also be fabricated according to the method of the present invention for the rapid screening of substances for their biological activity. For instance, spots of different organic or biological compounds are arranged in a two-dimensional array. The resulting matrix is then brought into contact with a surface of a cell culture or an agar gel to permit each substance to penetrate into the media. The reaction of the cells in the agar can then be monitored for any changes, i.e., morphological changes, zones of growth inhibition, etc. Matrices containing, for example, the majority of known antibiotics would be used for testing the sensitivity of infectious microorganisms to a panel of different antibiotics to facilitate the choice of the most effective course of treatment. The method according to the present invention can also be used to rapidly identify an enzyme inhibitor from among a variety of matrix components. After contact of the matrix with a filter containing an impregnated enzyme, enzyme inhibition can be found by using a histochemical reaction to reveal the distribution of enzyme activity over the area of contact between the matrix and the enzyme-impregnated filter. The mass fabrication of matrices containing spots of commercial drugs provides, for example, a ready means for determining the possible side effects of these drugs by testing for their effect on a number of key enzymes.

The method according to the present invention can also be advantageously used in the fabrication of combinatorial libraries, an area which is presently attracting a great deal of interest. In contrast to other techniques of designing combinatorial libraries, the compounds in the 2-dimensional libraries do not require labeling since they are identified by address in the matrices. Fabrication of such libraries using electrospray deposition technique include surface activation to make the surface capable of producing strong (covalent) bonds to a specific element of the structure of the compound (N- or C-end of-polypeptide, etc.), deposition of all nucleotides or amino acids via electrospray, deactivation of the surface, washing excess unbound compounds, activation of the end groups of the oligonucleotides or peptides. The series of such steps are to be repeated as many times as number of nucleotides or amino-acid residues introduced into chains.

Compared to the fabrication of such matrices using the known technology available in the art, electrospray deposition according to the method of the present invention greatly simplifies and accelerates the process. For example, both methods can use the series of six masks shown in FIGS. 10A–10F to spatially deposit each successive nucleotide to the 16,384 element library containing all possible combinations of 6-mer oligonucleotides. Each layer in this matrix can be obtained by rotating every mask by 90 degrees after the application of one of the four nucleotides. According to conventional technology, incorporation of each nucleotide requires the following steps: (i) photoactivation of certain substrate area(s) through holes in the mask (represented by white areas in FIGS. 10A–10F), (ii) reaction with a modified nucleotide (amino-acid) in solution, (iii) washing excess of the reagent. A whole new cycle of wet chemistry is thus performed for each new nucleotide incorporated.

By contrast, the method of the present invention allows all four nucleotides (or twenty amino acids) to be spatially distributed over the surface, and only then wet chemistry is performed to bind all nucleotides (amino acids) of the layer. For instance, the mask shown in FIG. 10A has a single large square hole (represented by white area), and in the first cycle of deposition of the first nucleotide of the combinatorial library of 6-mer oligonucleotides, an adenosine nucleotide is electrosprayed onto the substrate through this single large square hole. The mask is then rotated by 90° for each of the other three cytosine, guanosine and thymidine nucleotides so as to create a first layer of nucleotides in which each of the four quadrants of the substrates corresponds to the deposit of a different nucleotide. After chemical binding of the deposited nucleotides, the next layer of nucleotides is deposited using another mask and electrospraying each nucleotide by rotating the mask by 90° as done with the first mask. When each of the series of masks shown in FIGS. 10A through 10F are used successively (in any order), then all possible combinations of nucleotides in the 6-mer are generated. Photo-masks, similar to those shown in FIGS. 10A–10F, can also be used to deposit charged nucleotides onto a photoconductive dielectric substrate.

After the deposition of all four nucleotides into a layer, the chemical binding of a nucleotide to an oligonucleotide end is performed using conventional methods of solid state chemistry for nucleotide binding with the reaction being activated by placing the deposit into an atmosphere of saturated solvent vapor by raising temperatures or using any other known method to activate chemical reactions. Thus, electrospray deposition accelerates the synthesis of oligonucleotide matrices by at least 4 times and accelerates the synthesis of peptide libraries to an even greater degree (about 20 fold). The mass fabrication of such libraries is needed in the search for new drugs, genetic analysis, etc. In particular, DNA sequencing by hybridization of such combinatorial matrices with overlapping DNA fragments is one of the most exciting applications of oligonucleotide combinatorial matrices.

The present invention further contemplates an apparatus in which an electrosprayed mist of charged particles are guided to the deposit areas by electric fields.

Figure 24:
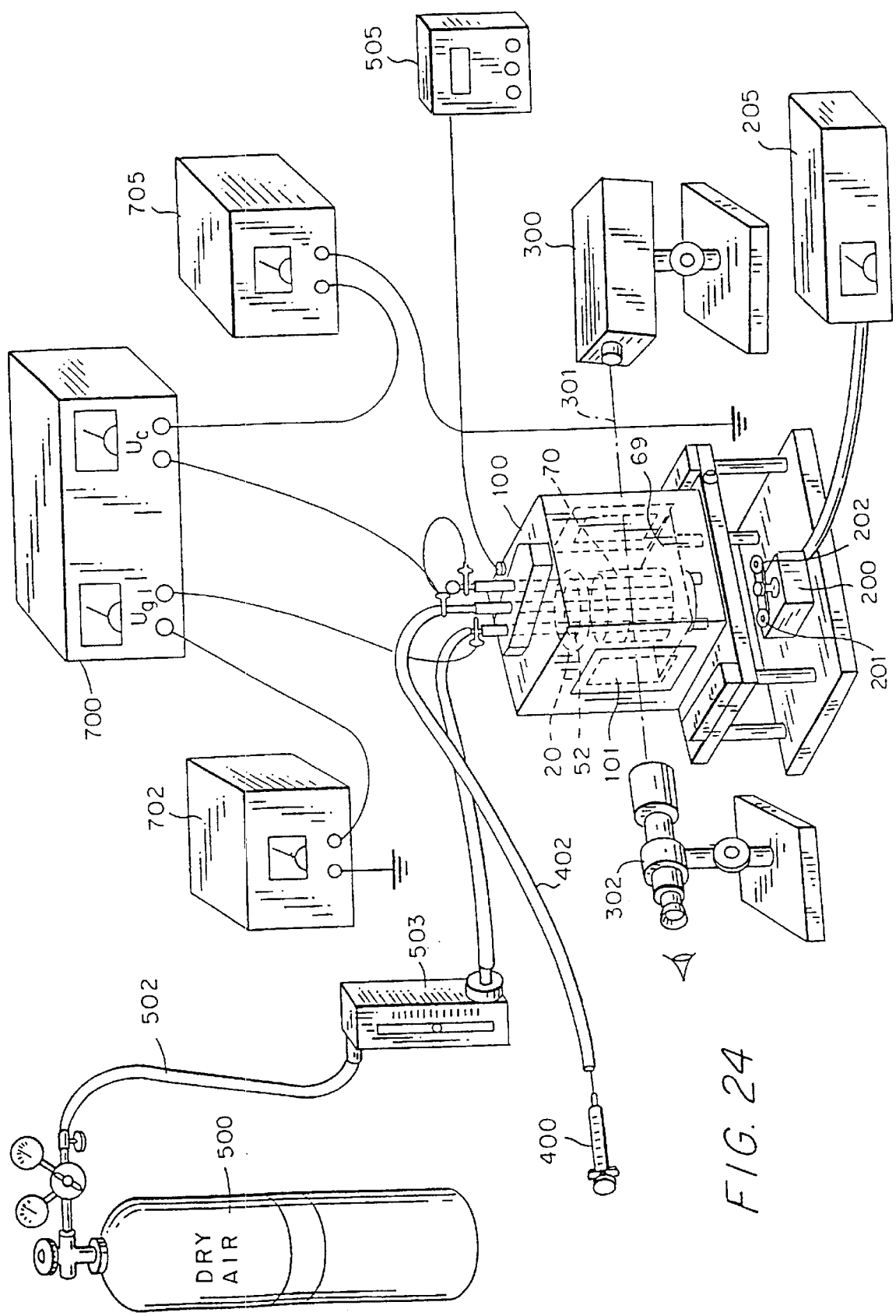
FIG. 24 is a schematic overview of the apparatus of the invention.

FIG. 24 shows the apparatus including an electrospray chamber 100 inside which are the capillary 52 from which a mist of electrically charged particles is emitted, a guard ring 20, a grid screen 70 which helps to contain and guide the mist of charged particles, and a substrate holder 69 which holds the substrate (not visible in FIG. 24) on which the deposits are made. The holder 69 preferably includes a bearing and magnets (not visible in FIG. 24) which are rotated by other magnets 201, 202 rotated by a step motor 200 which is preferably driven by a driver 205. This magnetic drive electrically isolates the chamber 100 and damps vibration.

The sides of the electrospray chamber 100 preferably include transparent windows 101 and the grid screen 70 includes holes (also visible in FIG. 27) or plastic windows which permit a laser 300 to shine a laser beam 301 through the electrospray chamber 100 into a microscope 302. This permits viewing of the "torch" of charged particles emitted from the capillary 52. Preferably the laser 300 is a Ne-Ar laser and the microscope has power 5× to 10×.

A syringe 400 is coupled into the chamber 100 by a tube 402. This is used to inject liquid to be turned into a mist of charged particles.

A supply of dry air (or other gas) from a tank 500 flows through a tube 502 and a flow meter 503 into the chamber 100. A humidity meter 505 is preferably provided with a sensor 506 inside the chamber 100. The humidity should be controlled to control the evaporation rate of the mist particles, which typically are droplets of an aqueous solution. Humidity is typically kept at about 10–30%. Besides the illustrated tank 500, dry air can be obtained with silica gel. Flow rates are typically 200–500 mL/min.

Figure 25:
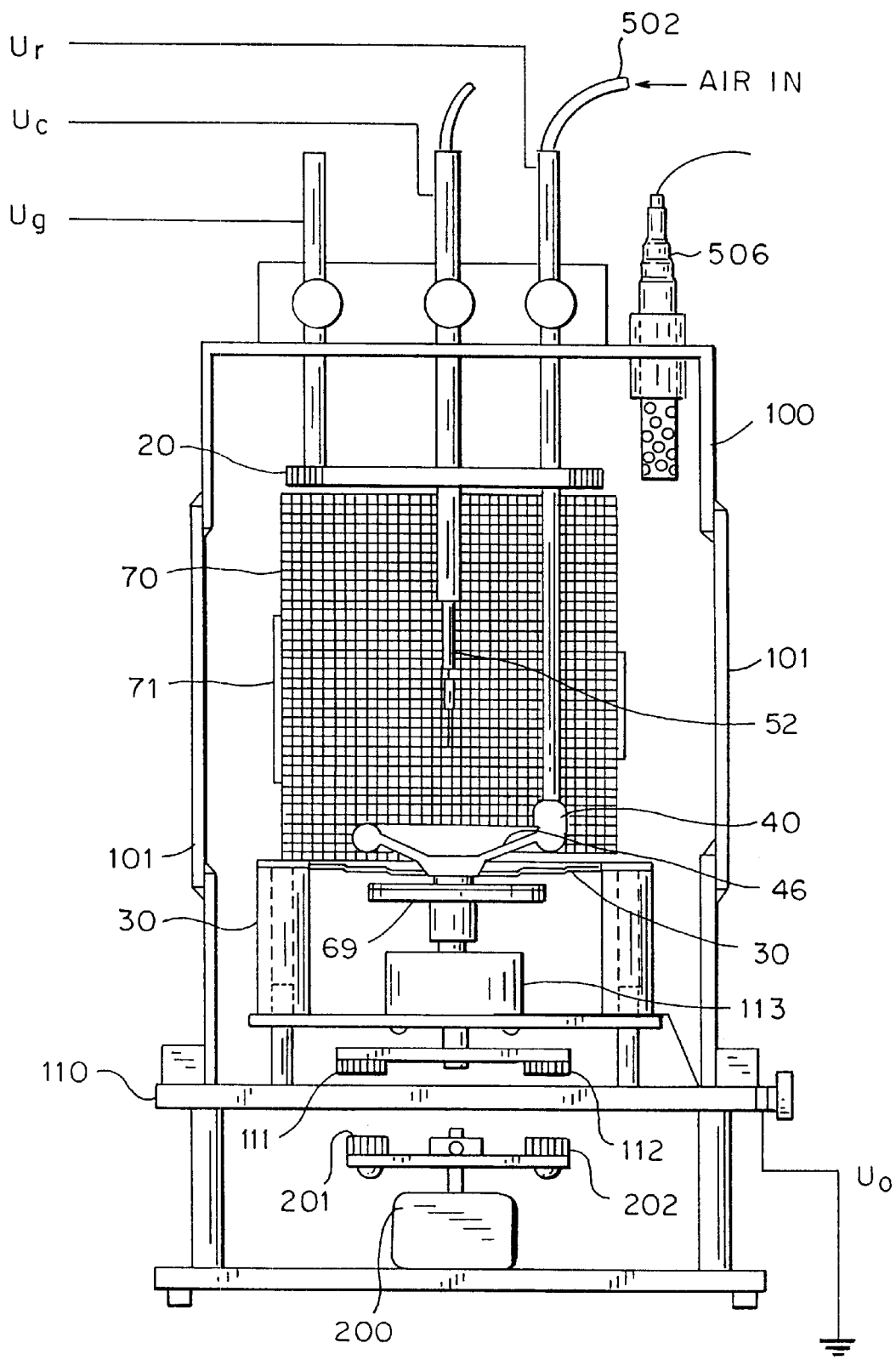
FIG. 25 is a schematic view of the electrospray chamber also shown in FIG. 24.
Figure 29B:
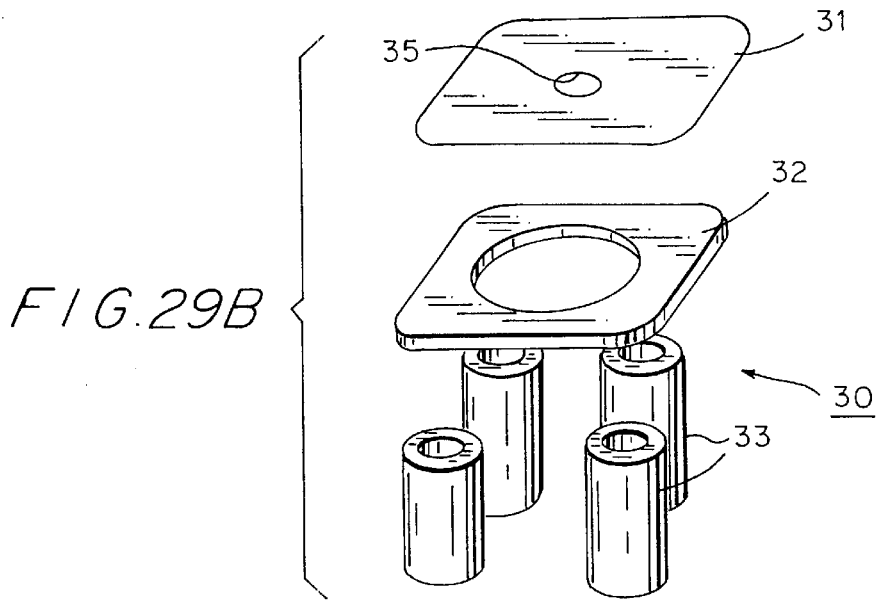
FIG. 29B is an exploded perspective view of the protective screen of the electrospray chamber.
Figure 30:
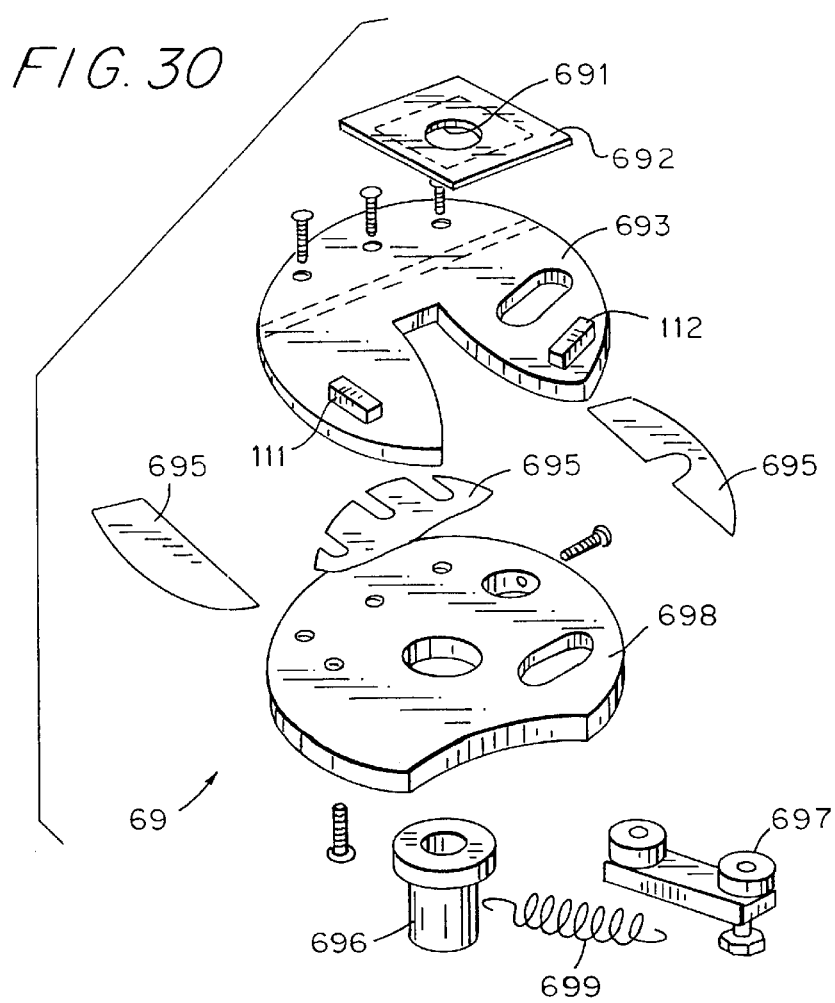
FIG. 30 is an exploded perspective view of the intermediate sample holder.

A dual power supply 700 supplies voltages $U_g$ and $U_c$ in the kilovolt range to the internal parts of the chamber as described below. Preferably the currents are measured with respective nanoammeters 702 and 705. Voltage $U_g$ goes to the guard ring 20, and the voltage $U_c$ is coupled to the capillary 52. Optionally, a single power supply can be used and coupled to both the guard ring 20 and the capillary 52. Both are to be set at a potential repulsive to the mist of charged particles emitted from the capillary 52.

FIG. 25 shows the electrospray chamber 100 in more detail. The chamber 100 preferably has an open bottom which rests on a base 110 in which are the step motor 200 and magnets 201, 202. These drive corresponding magnets 111, 112 to rotate about a bearing 113 on which is mounted the sample holder 69.

A protective screen 30 (also shown in FIGS. 29A and 29B) stands above the sample holder 69 and supports the grid screen 70 (also shown in FIG. 27). It preferably includes four acrylic-tubing legs 33, a polystyrene ring 32, and a Teflon® top plate 31 with a central hole 35. The top plate 31 is preferably slightly deformed, concave downward as shown.

Just above the protective screen 30, and inside the screen grid 70, is the collecting ring 40. The collecting ring 40 is hollow and at its upper end couples to the dry air tube 502 seen in FIG. 24. The air passes through a preferably stainless steel tube 42, partially sheathed in silicone tubing 43, through a polyethylene coupling 44 to a hollow silicone tubing ring 45. From the ring 45 smaller Teflon® tubes 46 converge on a central opening.

Preferably, a copper ring 47 is located in the central opening, which is to be disposed above the hole 35 of the protective screen 30. The stainless tube 42 may be electrified by a voltage $U_r$ from the power supply (not shown in FIG. 25 or 28) and the voltage conducted through a wire passing through one of the Teflon® tubes 46. The voltage $U_r$ may be used as an aide in guiding charged particles. The voltage is shown as being transmitted through an alligator clip, which is merely exemplary.

Preferably, the voltage $U_r$ on the copper ring 47 is intermediate the voltage on the sample holder 69 (and the substrate held by it, see FIGS. 3 and 4) and the voltage on the capillary 52 which has voltage $U_c$, as described below.

The screen grid 70 is preferably made of woven polypropylene screen cloth with 1000-micron holes, available from Small Parts, Inc., Miami Lakes, Fla., as item CMP-1000-A. The holes should be about 1.0–1.5 mm and the material should be a good dielectric. The windows 71 are preferably acrylic plastic for optical-quality light transmission. An alternative funnel-shaped screen grid is shown in FIG. 16A and is described below.

Still within the screen grid 70 is the capillary 52, preferably made of glass, and the capillary holder assembly 50, best shown in FIG. 26. Liquid to be sprayed arrives from the tube 402 (also seen in FIG. 24) and passes to the capillary 52 through a nickel-plated brass tube 53, a smaller stainless steel tube 54, and thence out of the orifice of the drawn-glass tube 52. The bore of the capillary 52 should not exceed 30–40 microns outside diameter, and the outside surface should be treated to be hydrophobic. The emerging liquid is electrified by a fine platinum wire inserted through the bore of the capillary tube 52, which is electrically connected to voltage $U_c$ from the power supply 700 (FIG. 24) via the brass and steel tubes and the exemplary alligator clip. The guard ring 20 is merely a metal toroid or annulus disposed near the upper end of the screen grid 70.

FIG. 30 shows the parts of the sample holder table 69. The upper part rotates on a brass pedestal 696 soldered to a brass plate 698, on which are fastened an acrylic plate 693 on spacers 695. The driven magnets 111 and 112 are mounted on the acrylic plate 693. A mask assembly 691 is held by an acrylic sub-holder 692 glued to plate 693. Bearings 697 and spring 699 aid in accurate positioning.

Rotation of the sample holder 69 during deposition is a requirement for obtaining uniform deposition films when air flow rates are low.

FIG. 31 shows a sample holder which fits into the sample holder table 69 shown in FIG. 30. The sub-holder 692 is mounted on a plastic table 6922 which in turn is mounted on a base 6923 with a handle 6924 to place the sample holder into the space bounded by the brass plate 698, spacers 695, and acrylic plate 693. Carbon paste is preferably used to form an electrical contact to an electrostatic device, e.g., electrostatic devices 581 or 621 in FIG. 4A or 95 in FIG. 4B.

FIG. 32A illustrates an embodiment of the present invention in which wobblers are used to oscillate or vibrate the electrospray capillary 52. The electrospray holder 50 is moved preferably by a wobbling motor 250 and a mechanism 252 coupled to the brass tube 53 (or some other suitable part of the capillary holder assembly 50) for to-and-fro or rotary motion; a second mechanism 252 is set at right angles to the first. The mechanism preferably is designed so that the tip of the capillary 52 spends equal amounts of time over each area portion of the substrate 58. Any other means to oscillate the capillary is within the scope of the invention.

The embodiment of FIG. 32A also illustrates an exemplary structure for fabrication of matrices consisting of multiple dots. In this embodiment the sample holder 69 and substrate 58 is shifted, after deposition of each compound, in horizontal directions X and Y, which are generally perpendicular to the motion of the charged particles 56. In the embodiment of FIG. 32A the bearing 113, magnets 201, 202, 110, 112, step motor 200, and driver 205 of FIG. 25 are not used.

The shifting is accomplished by an X-Y translation stage, which may be of any type. FIG. 32A shows a manually-operated type of translation stage with respective X-motion and Y-motion micrometer heads 121, 122 having vernier scales, but the translation stages may be of any manual type or automatic, e.g., of the type driven by step motors or the equivalent and controllable by a momentary contact switch, circuit, or computer program. A magnet 115 is preferably used to attach the sample holder 69 onto the translation stage with an electrode 102 disposed between the magnet 115 and the substrate 58.

The present invention also contemplates arrays of deposits in other geometries, for example, deposits arranged along circles of different radii with θ, r rotators or translators instead of X, Y translators.

The translation stages permit the substrate to be shifted so that the mask holes are moved to new positions above an area of the substrate. New deposit areas can then be deposited with new substances. A matrix of different substance deposits can be arrayed in rows and columns.

FIG. 32B shows the mask 62, mask holes 60, substrate 58, and deposit 64 enlarged from the circled portion of FIG. 32A. Mask reinforcement beams 61, shown in cross-section, are preferably strips fastened to an upper side of the mask 62, but may be a honeycomb grid, etc. Spacers 6258 are placed between the mask 62 and substrate 58. The spacers 6258 are preferably small spheres so that the mask 62 can roll in any direction on the surface of the substrate 28.

FIG. 33 shows another embodiment of a mask shifter with a first plate slidable in an X-direction on a second plate 126, where the second plate 126 is slidable in a Y-direction on a base plate 127. Wobblers for X and Y motions, in the form of cams 123, 124, bear on the edges of the plates 125 and 126, respectively. When the cams are rotated the plates move. This mask shifter may be placed onto the rotating-table sample holder 69 of FIG. 25.

FIG. 34 shows a chamber 100 like that of FIG. 25, except that the rotating sample holder table 69 is larger in diameter and the deposition takes place on one side of the chamber 100 (on the right in FIG. 34). On the other side, the mask 62 is recharged by a stream of counter-ions 856 discharged from a corona electrode 850 coupled to an electrostatic device (not shown in FIG. 34). The counter-ions are so-called because they are opposite in polarity to the charged particles; FIG. 34 shows, for an example, that the charged particles to be deposited on the dielectric substrate 58 are of positive polarity, while the counter-ions are negative. The corona electrode preferably includes an array of microelectrodes.

To prevent the electric field from the corona electrode 850 from disrupting the flow of charged particles 56 from the capillary 52 to the mask 62, the corona electrode 850 is preferably enclosed in a protective shield, e.g., a Faraday shield, 840, which may be grounded. The bottom of the shield 840 is open and placed near to the mask 62. Preferably, a counter-electrode 842 is placed just under the table 69, which tends to complete the Faraday cage and enclose a portion of the substrate within metal. However, the counter-electrode 842 is preferably not grounded but instead is coupled to an electrostatic device (not shown) which places a voltage on the counter-electrode which is attractive to the counter-ions 856, and causes them to move downward onto the mask 62.

A second counter-electrode 844 if preferably placed under the table 69 below the capillary 52, on the other side of the axis of the table 69 from the first counter-electrode 842. The second counter-electrode 844 is preferably opposite in polarity to the electrospray capillary 52 and also to the first counter-electrode 842.

In the arrangement of FIG. 34, the rotating table 69 should not be metallic since this would prevent the electric fields from the counter-electrodes from reaching the mask 62. The rotating table 69 is preferably made from a dielectric such as plastic or mica.

Having now generally described the invention, the same will be more readily understood through reference to the following examples which are provided by way of illustration and are not intended to be limiting of the present invention.

EXAMPLE 1

A 0.01% aqueous solution of horse myoglobin (Sigma, St. Louis) was electrosprayed onto a conducting surface of glass through a monofilament cloth with multiple holes. The conducting glass surface was prepared by treating a glass microscope slide with $SnCl_4$ vapor in an oven. A ±5 kV was applied to the electrospray capillary, and a polypropylene tissue was used as a mask to electrofocus the electrospray for deposition onto the conducting glass surface. Comparison of FIGS. 5A and 5B shows that the myoglobin protein is deposited into spots of 5–7 microns in size, whereas the size of the is holes in the tissue is about 22–23 microns, which illustrates the electrostatic lens effect. Some missed spots in the pattern are due to occasional dust particles, which are observed to be present on the screen. This example demonstrates that protein can be deposited simultaneously into numerous spots. Thus, a 20×20 $mm^2$ area of glass substrate covered with spots separated by a distance of about 47 microns was found to contain $1.8 \times 10^5$ spots of protein.

EXAMPLE 2

Figure 11:
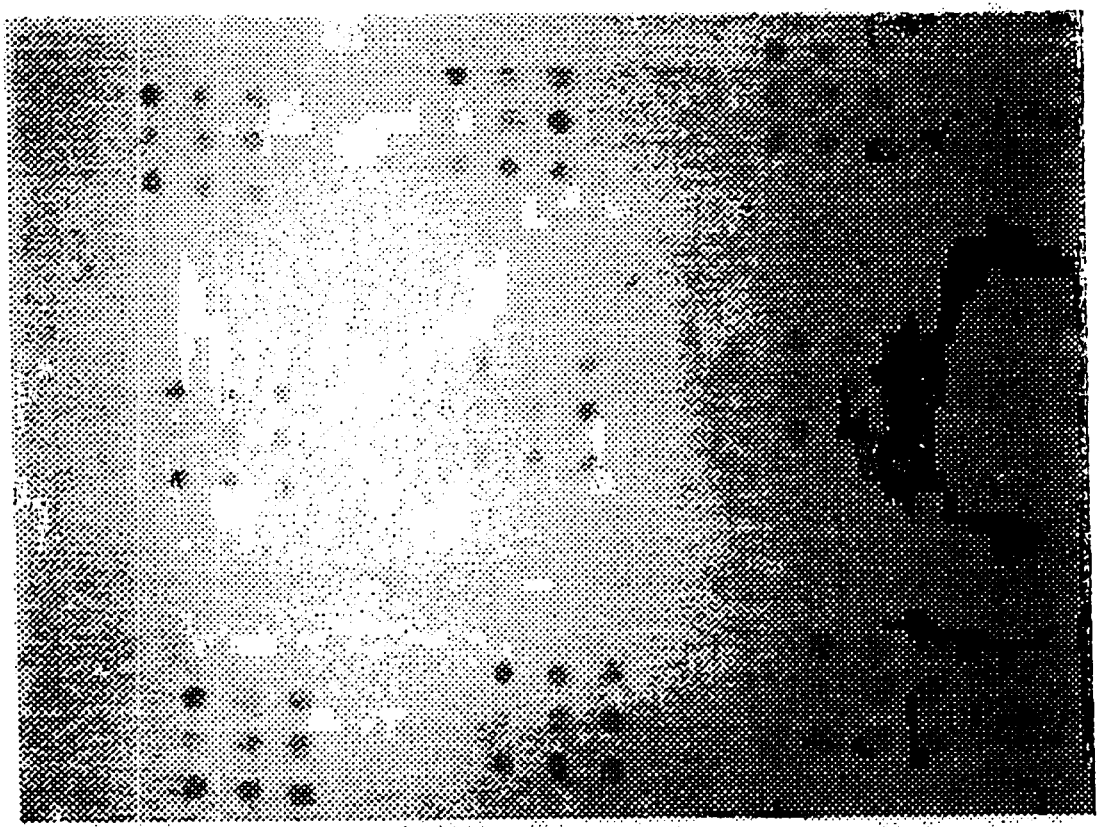
FIG. 11 shows a porous IMMOBILON-P membrane filter on which a number of multicomponent matrices of different dye spots are deposited.

Solutions of nine different dyes (0.01%) in methanol were electrosprayed through the holes in a Teflon screen (mask) onto a surface of a porous IMMOBILON-P filter (Millipore) which was made slightly conductive by soaking in a solution containing 15% polyethylene glycol-8,000, 10 mM $MgCl_2$ and 15% glycerol. Electrospray deposition was performed with ±7 kV at the capillary, through a Teflon mask with 100 holes of 0.5 mm diameter at a distance of 4 mm. After deposition of 0.5 microliters of each solution, the mask was shifted by approximately 0.6 mm and another dye was deposited. A fragment of the porous IMMOBILON-P filter containing the matrices of deposited dye spots is presented in FIG. 11. This example demonstrates the ability of the method according to the present invention to pattern substances over a substrate to simultaneously produce numerous multianalyte samples and libraries.

EXAMPLE 3

The electrospray conditions used in this example were similar to those used in Example 1. Two commercially available proteins, peroxidase and alkaline phosphatase (Sigma Chemical Company, St. Louis, Mo.), that were dialyzed against distilled water, were electrosprayed through holes in a polypropylene mask onto a surface of a slightly wetted nitrocellulose filter to demonstrate that proteins, deposited by electrospray into a pattern, retain their functional properties, namely the ability to specifically bind their natural ligands and catalyze enzymatic reactions.

Figure 12A:
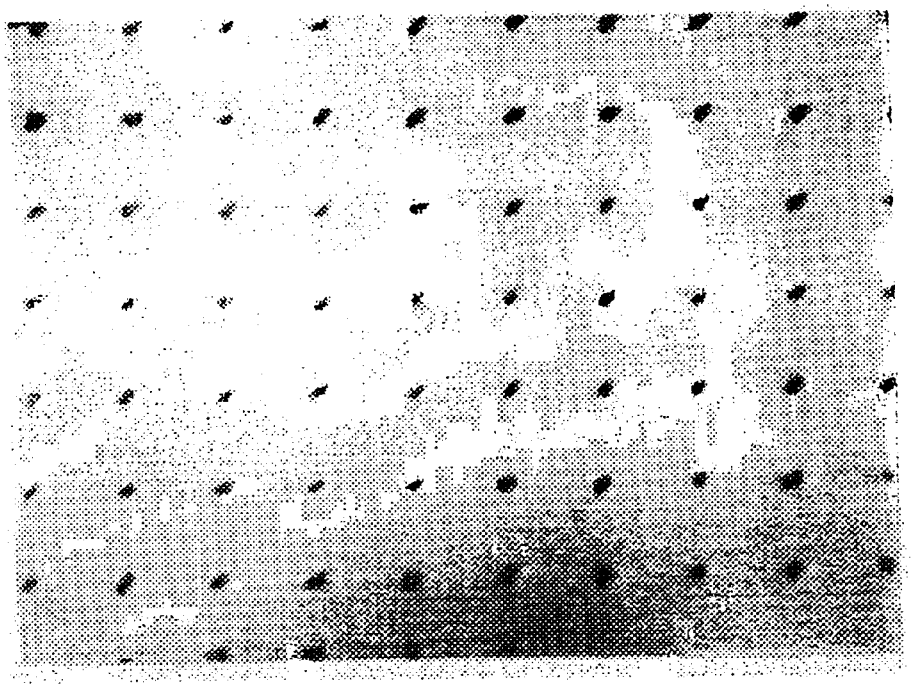
FIGS. 12A and 12B show the electrospray deposition of solutions of peroxidase (FIG. 12A) and alkaline phosphatase (FIG. 12B) onto a wet IMMOBILON-P membrane filter. The black dots are the accumulation of insoluble products of the peroxidase and the alkaline phosphatase enzyme reactions and reveal the positions of the deposited enzymes on the membrane filter.

After electrospray, the pattern of deposited enzyme was not visible on the membrane filter surface. However, the patterns of the enzymes did become visible after soaking the peroxidase-deposited membrane filter in a solution of a standard peroxidase substrate (3,3'-diaminobenzidine, abbreviated DAB, and obtained from Sigma, St. Louis, Mo.), resulting in the formation of an insoluble brown colored product of the peroxidase reaction. The array of dots indicating the presence of insoluble product is shown in FIG. 12A.

Figure 12B:
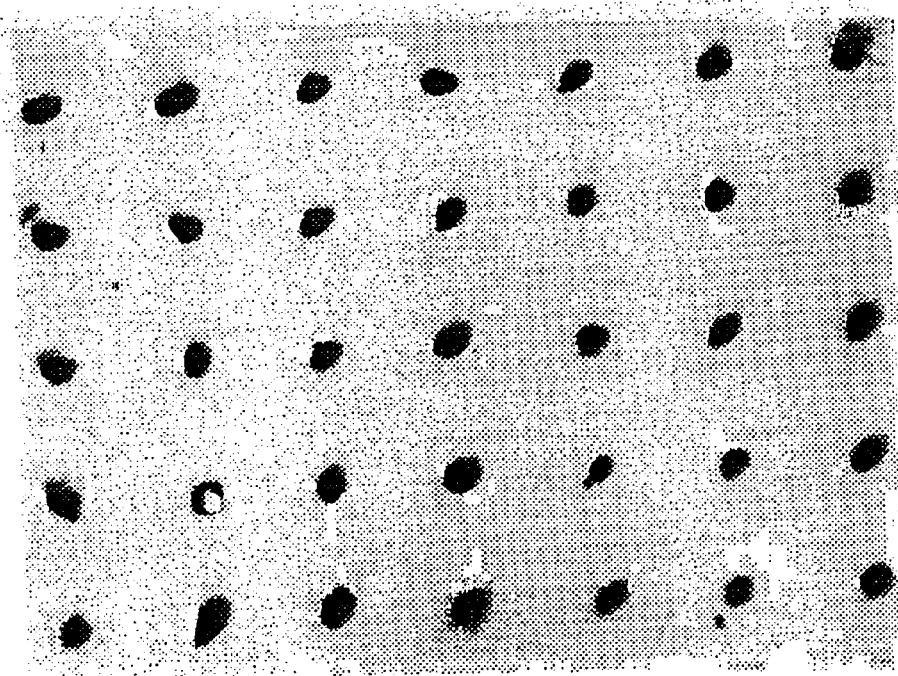

Likewise, the membrane filters on which alkaline phosphatase was deposited was soaked in a standard alkaline phosphatase substrate (5-bromo-4-chloro-3-indolyl phosphate/nitro blue tetrazolium substrate system kit, Sigma, St. Louis, Mo.), resulting in the formation of an insoluble blue colored product of the alkaline phosphatase reaction, and the pattern was visualized as shown in FIG. 12B. The results demonstrate that the enzymatic activity of alkaline phosphatase and peroxidase is retained after electrospray deposition.

EXAMPLE 4

Figure 13:
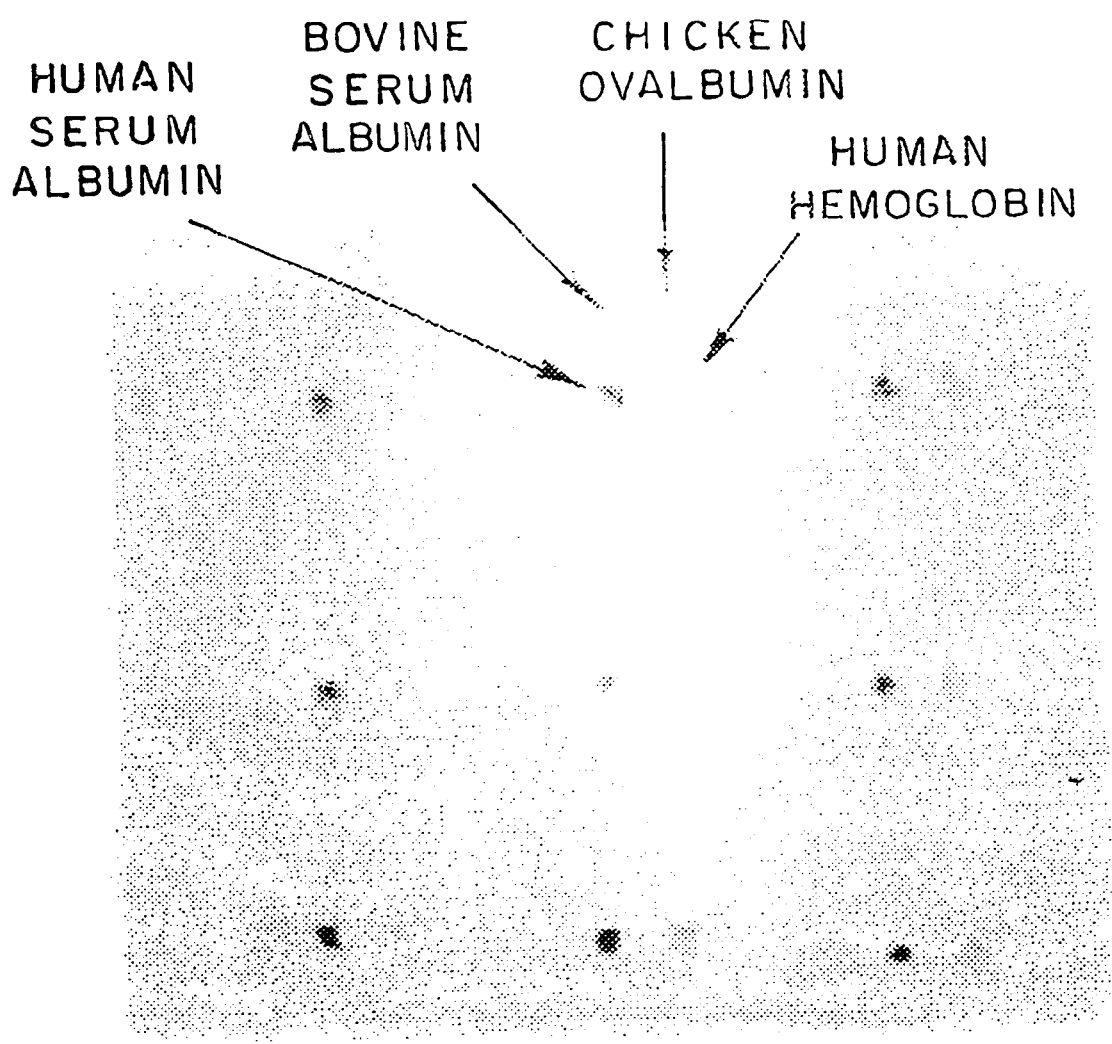
FIG. 13 shows a microELISA assay of different protein antigens (human and bovine serum albumin, ovalbumin, human hemoglobin) deposited by electrospray onto an IMMOBILON-P membrane filter and detected by an immunoenzyme technique with a primary rabbit antibody specific to human serum albumin and a secondary anti-rabbit IgG molecules conjugated with alkaline phosphatase.
Figure 14A:
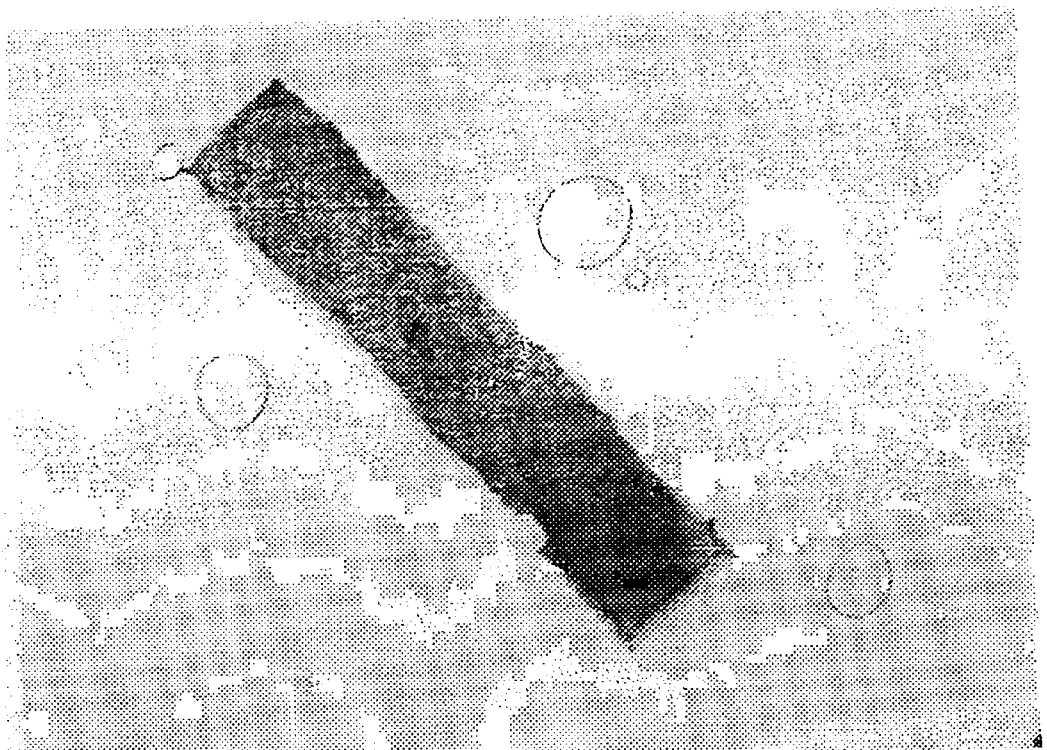
FIGS. 14A and 14B show electrospray fabricated films of concanavalin A (FIG. 14A) and alcohol dehydrogenase from horse liver (FIG. 14B). Protein films were deposited through a single rectangular hole (0.8×0.2 mm) in a mask onto a conducting polymer sublayer film previously deposited onto an Al electrode.
Figure 14B:
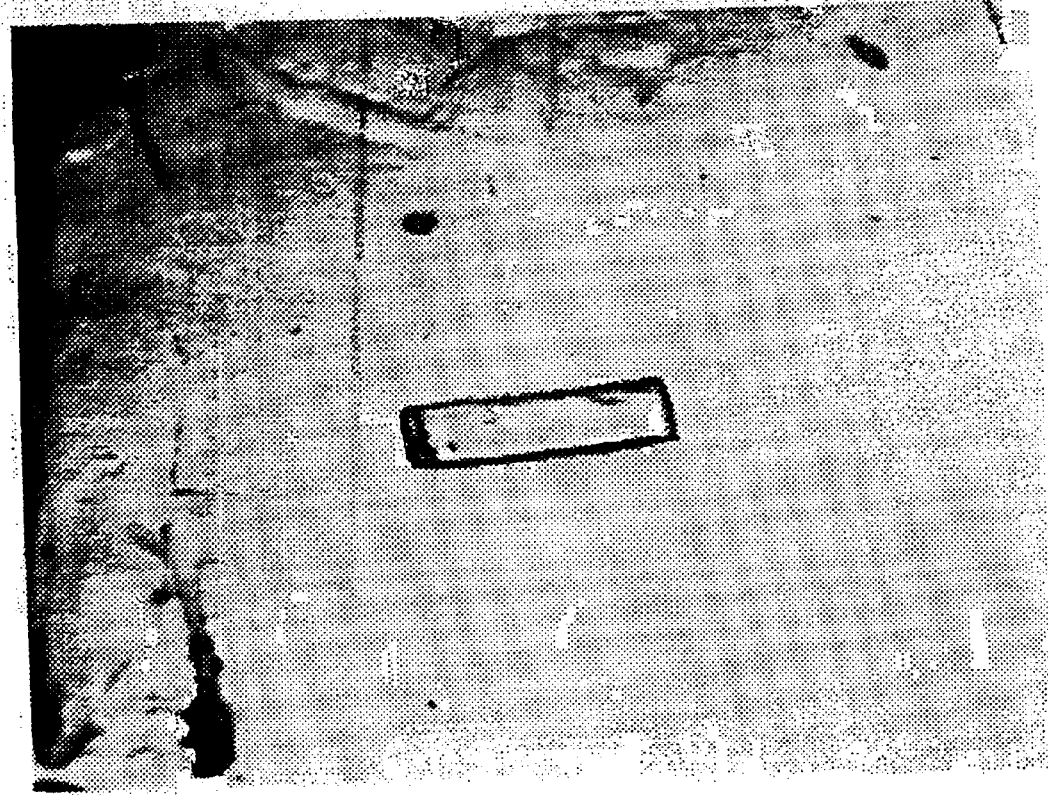
Figure 19A:
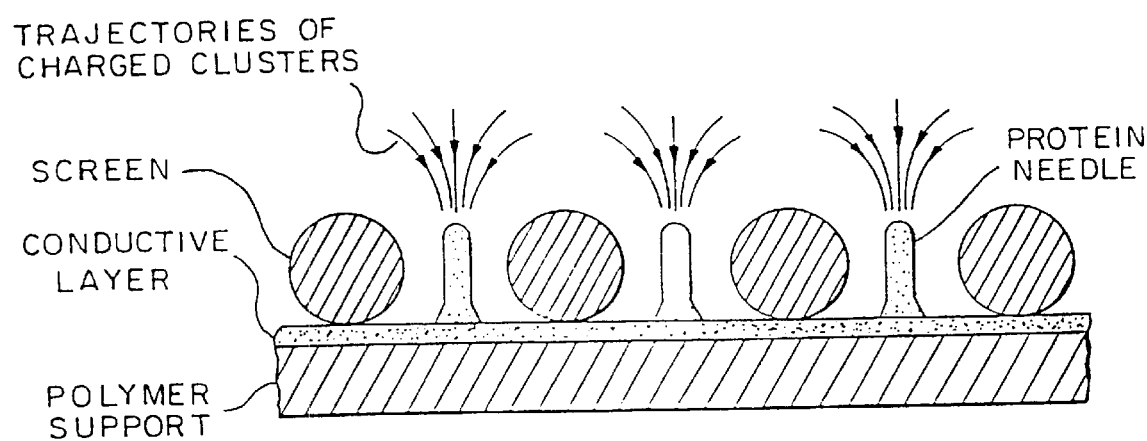
Figure 19B:
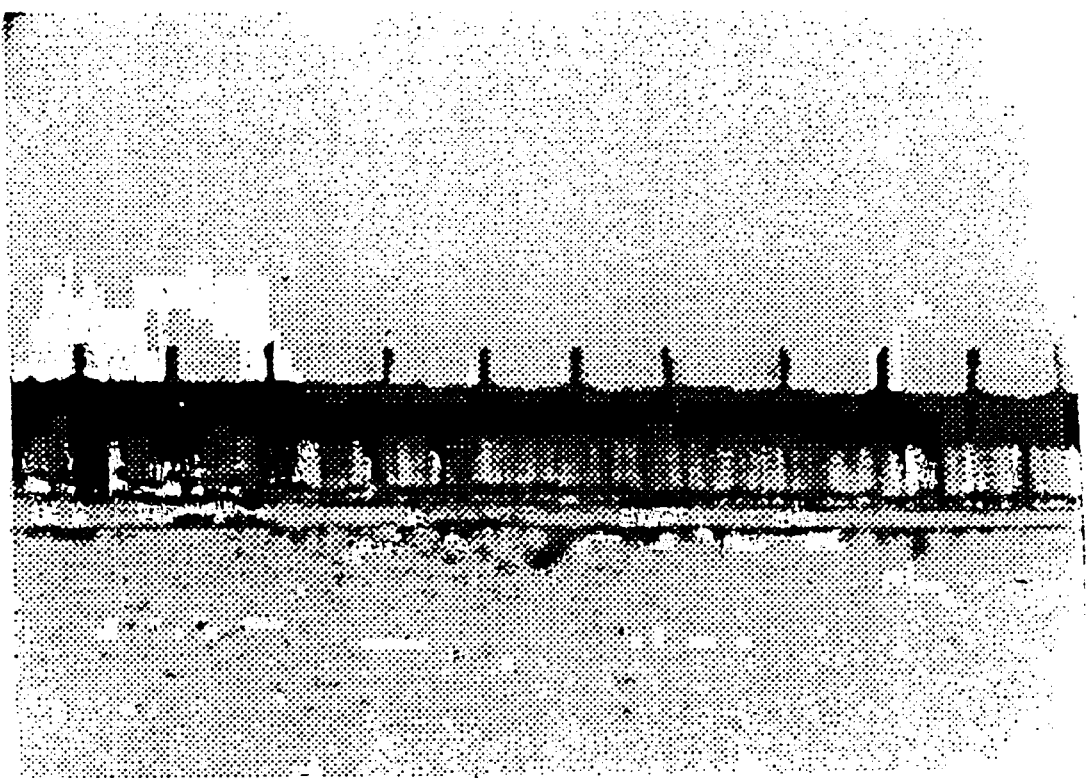

Different antigens (serum albumins from human and ox, ovalbumin and human hemoglobin) were electrospray deposited onto a wetted IMMOBILON-P membrane filter through a mask having multiple holes. After each deposition of a different protein antigen, the mask was shifted by 1.1 mm. After depositing all four protein antigens, the membrane filter was dried for 15 min. at 37° C. and blocked by soaking in a PBS solution (10 mM sodium phosphate buffer, pH 7.2, 0.9% NaCl) with 0.05% Tween-20, 1% chicken albumin (ovalbumin). After blocking, the membrane filter was soaked in a solution of a goat antibody against human serum albumin (Sigma, diluted 1:1000) for an hour. The filter was then washed twice with PBS buffer for 10 seconds and reacted with a solution of anti-goat IgG antibodies labeled with alkaline phosphatase (Sigma, diluted 1:3000). After washing off excess anti-goat antibodies with PBS, the position of the enzyme-labeled spot was identified by soaking the filter in a solution of an alkaline phosphatase substrate capable of producing an insoluble product as described in Example 3. FIG. 13 shows a pattern obtained by using this microELISA assay. As was expected the spots corresponding to the deposition of human serum albumin are the most intense. The spots of other proteins either are not visible at all as that of ovalbumin or less intensively colored as bovine albumin and human hemoglobin, presumably due to some cross-reactivity of anti-human albumin antibody to the bovine albumin and due to some human albumin contamination in human hemoglobin sample. This example shows that electrospray procedure itself does not change considerably antigenic properties of proteins and demonstrates the applicability of electrospray to the mass fabrication of multicomponent immunoenzyme probes.

EXAMPLE 5

Protein films were prepared by electrospray for use in a mechanochemical method of assay. A 2 mg/ml concanavalin A (Sigma, St. Louis, Mo.) solution, containing 0.5 mg/ml of glycerol was electrosprayed through a rectangular single hole onto an Al electrode covered with a polymeric conducting sublayer of about 2–5 microns thick. The sublayer was prepared by drying a thin layer of water solution of a mixture of three compounds (polyethylene glycol-8000, poly(anetholesulfonic acid)—Na-salt and Triton X-100), 3%. each. The protein solution was electrosprayed from a capillary tip placed 20 mm over the substrate, with positive voltage of 4.0 kV at the capillary and a current of 33 nA. Deposition was performed in dry air for 10 minutes. After electrospray deposition, the sample was cross-linked for 15 minutes in a vapor of 25% glutaraldehyde (Aldrich Chemical Company, Milwaukee, Wis.) at 25° C. Upon applying a droplet of water on the substrate surface, the sample was floated off the substrate within 5 seconds. To prepare a microphotograph of the sample, as presented in FIG. 14A, the sample was stained by treatment with a solution of Coomassie brilliant blue R (Sigma, St. Louis, Mo.) placed in a droplet of water and covered by a cover slip.

A film of horse liver alcohol dehydrogenase (LADH, Sigma, St. Louis, Mo., shown in FIG. 14B, was fabricated on an Al electrode covered with a sublayer consisting of 95% of the sodium salt of alginic acid (Sigma, St. Louis, Mo.) and 5 of Triton X-100 detergent. The LADH solution containing 5 mg/ml of protein and 1.5 mg/ml of sucrose was electrosprayed in dry air at +4.3 kV and 30–40 nA from a capillary placed about 15 mm over the substrate. The deposited film was cross-linked for 8 minutes with the vapor from 25% glutaraldehyde at 28° C. The samples were then tested for their ability to change isometric tension in response to 0.4 mM NADH solution. Similar 6–7% ligand-induced increase in isometric tension of both the electrospray deposited and conventionally prepared films indicates that electrospraying retains the functional ability of proteins to specifically bind ligands and change their conformation as a result of such binding.

These examples demonstrate that small protein samples of a uniform thickness, which is important for testing proteins by a mechanochemical method, can be fabricated by electrospray deposition without loss of their functional activity.

EXAMPLE 6

The deposition of protein from concentrated protein solutions in a dry atmosphere results in the formation of a porous structure. FIG. 15A presents an atomic force microscopy (AFM) image of a human hemoglobin film deposited onto a polished gold electrode. The protein was electrosprayed from an aqueous solution containing 0.6 mg/ml human hemoglobin with no other additives added. Deposition was performed in dry air at +5.3 kV on a capillary placed at a distance of about 20 mm over the substrate, with a current of 12 nA and solution flow rate of 100 nl/min. The image presented in FIG. 15A shows the presence of protein clusters with sizes up to about 300 nm. Exposure to humid air (100% relative humidity at room temperature for 20 minutes) resulted in the disappearance of large clusters and the formation of a flat surface with narrow "channels" which are visible as black structures in the image presented in FIG. 15B. FIG. 15C illustrates enhanced penetrability of electrospray-deposited protein film. In this example, small pieces of solid dye were placed onto the surface of both electrospray-deposited and dried films and the films were then placed into a humid chamber having 100% humidity. In the presence of water, dye molecules penetrate the protein film, forming a diffuse concentric colored zone around each dye piece. As seen from FIG. 15C, the diffusion of the dye proceeds many times faster in the electrospray-deposited film relative to the films prepared by conventional methods of drying the protein solution. This example illustrates that the fabrication by electrospray deposition allows the preparation of new porous materials from substances which-otherwise form homogeneous dense films when dried from solution. It also illustrates a means to regulate porosity, and therefore penetrability, to specific ligands of electrospray-fabricated films after deposition by "baking" in an atmosphere containing solvent vapor, thereby permitting the relative displacement of protein molecules within the clusters.

EXAMPLE 7

λ-DNA stock solution (product of New England Biolabs) containing 0.5 μg/μl of DNA was diluted twice with water, denatured by boiling for 5 min and snap cooled in ice. 10 μl of this solution was placed in a capillary and 1 μl was electrosprayed at a voltage of +4.9 kV and a current of 40 nA using a platinum wire inserted into capillary as electrode. Deposition was performed through a polypropylene woven screen (mask) with rectangular holes (Type E-CMP-250 of Small Parts, Inc., Florida) onto the surface of a cover slip briefly treated with plasma discharge to make the glass surface hydrophilic. Electric contact with the glass surface was made by a wet o-ring cut out of a Whatman 3M paper. The deposited DNA was cross-linked by UV-irradiation for 15 min, rinsed in 0.1% SDS and then washed twice with water. The slides were then rinsed in 0.1 M borate buffer, pH=8.0, and placed into 70 mM succinic anhydride, prepared in the same buffer containing 35% 1-methyl-2-pyrrolidinone (Aldrich product) for 10 min. Slides were then washed by the borate buffer for 2 min and, by water 4 times by 2 min. A biotinylated EcoRI digest of λ-DNA obtained from Sigma was boiled, snap cooled in ice and added to hybridization solution at a final concentration of 100 ng/ml. A 4×SSC solution containing 1% SDS 10% dextran sulfate and 100 μg/ml of digested DNA from salmon testes (Sigma product) was used as hybridization solution. Hybridization was performed for 14 hours at 62° C. in a home made micro-chamber. After hybridization, the slides were washed twice with 2×SSC solution, once with 0.2×SSC solution for 5 min, and then blocked for 30 min in AP buffer containing 2% BSA and 1% casein. AP buffer consisted of 0.1 M TRIS-HCl buffer, pH=7.5, 0.1 M NaCl, 2 mM $MgCl_2$ and 0.5% Tween-20. After blocking, the slides were washed with AP buffer for 5 min and incubated for 25 min in 1 μg/ml solution of streptavidin-alkaline phosphatase conjugate (Sigma product) prepared on AP buffer. Slides were then washed 4 times with AP buffer, rinsed in AP buffer with pH adjusted to 9.5 and placed in standard substrate solution of alkaline phosphatase, as described in Example 3. Arrays of spots similar to those presented in FIGS. 12A and 12B appeared on glass as indication of the concentration of alkaline phosphatase in the DNA spots due to binding with biotinilated DNA hybrids.

EXAMPLE 8

In another experiment, λ-DNA denatured molecules prepared as described in Example 7 were electrosprayed onto nylon filter (DuPont's Gene Screen hybridization filter) from solution containing 20% glycerol and 0.01% of Bromphenol Blue dye. The latter was added to visualize the sprayed pattern before hybridization, where all the dye was then extracted from the filter during prehybridization. Deposition was performed in a humid glove box under a relative humidity of 60%. The filter was placed onto a wet Whatman 3M paper covering a carbon electrode, and the filter was then covered with propylene woven screen similar to that used in deposition of DNA on glass. 2 μl of the target DNA solution were electrosprayed at a voltage of +(4.2–4.5) kV and a current of 20–30 nA. After deposition, the DNA was baked for 20 min at 75° C., denatured in 0.5 M NaOH solution, washed in 0.5 M TRIS-HCL buffer, pH=7.4, and UV cross-linked for 15 min. Filters were then prehybridized for 1 hour at 42° C. in buffer containing 6×SSC buffer, 45% formamide, 1% SDS, 10% dextran sulfate, 5×Denhardt's solution and 100 μg/ml of denatured sonicated DNA from salmon testes. Hybridization was performed at 42° C. for 14 hours in the same solution to which 200 ng/ml biotinilated λ-DNA probe, similar to that in the above experiment was added. Hybridization was followed by washing with 2×SSC buffer (5 min), 2 washes with 2×SSC, 0.2% SDS solutions at room temperature and then by incubation in 0.1×SSC with 0.2% SDS at 62° C. twice for 15 min each. After washing, the filters were rinsed with AP buffer, blocked with a mixture of 2% bovine serum albumin and 1% casein in the AP buffer for 1 hour at room temperature, and then incubated in a solution of the strepavidin-phosphatase conjugate, washed and incubated in AP substrate as described in the previous Example. Arrays of bluish spots similar to those presented in FIGS. 7, 12A and 12B appeared, revealing the positions of electrospray deposited spots of λ-DNA.

Examples 7 and 8 illustrate that electrosprayed DNA molecules retain their ability to specifically interact with complementary strands and opens the application of the electrospray technology to the fabrication of DNA-based tests and libraries.

EXAMPLE 9

In this example, different dyes were electrosprayed from water solution in an air-assisted mode. To perform the electrospray, the end of a stainless steel needle was inserted into a jet of compressed air coming from a plastic nozzle. ±(2–5) kV was applied to the needle, and another pole of the high-voltage power supply was connected to a metal plate. A 30×30 cm, slightly wet Whatman 3M paper was placed onto the metal plate and covered with a perforated plastic mask about 1 cm thick with array of round holes of 13 mm in diameter. Air jet-assisted electrospray was performed from 0.2–1 m distance to substrate with the rate of solution spray of 0.1–1 ml/min. After deposition of one dye, the mask was shifted by a small distance and another dye was deposited. The deposited patterns are shown in FIG. 17. It is similar to the ones obtained by use of pure electrospray with the only difference being that much larger samples (spots) can be deposited on a much larger area more quickly and from larger amount of material. This example illustrates that the basic phenomena of electrofocusing, electroconcentration and patterning through a multi-hole mask can also be used with any other means of producing charged particles and droplets, besides pure electrospray.

EXAMPLE 10

A 0.5% aqueous solution of pancreatic RNAse (Sigma, St. Louis), containing 30% of sucrose and 10% of glycerol (based on the dry weight of protein) was electrosprayed onto a conducting aluminum layer on a polymer support through a monofilament cloth with multiple holes similar to that used in Example 1. Electrodeposition was performed for 10 minutes in a closed chamber with a relative humidity of 18%, +4.0 kv applied to the capillary with an internal diameter of 10 microns and current of 10 nA. A larger amount of electrodeposited material as compared with that in Example 1 revealed an ability to produce samples with three-dimensional features. As shown in FIG. 19B, arrays of protein samples with a lateral size of 5–7 microns and a height of 30–40 microns can be fabricated with the electrospray method according to the present invention using the lens effect in closely placed holes in a dielectric mask, as shown schematically in FIG. 19A.

EXAMPLE 11

MATERIALS AND METHODS

Materials. Alkaline phosphatase (AP) from bovine intestinal mucosa, p-nitrophenyl phosphate (pNPP substrate table set, Sigma Fast), trehalose and sucrose were obtained from Sigma Chemical Co., St. Louis, Mo. All other salts and buffer reagents were of analytical grade.

Figure 20A:
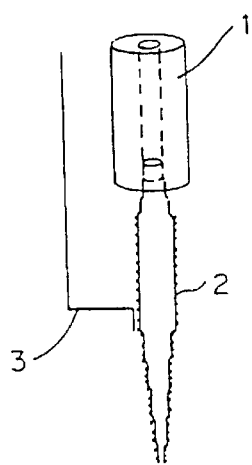

Design of Capillaries for Electrospray. Three different designs of the electrospray capillaries have been tested throughout this study. A first design, shown in FIG. 20A, is similar to the "nanoelectrospray ion source" (Wilm et al., 1994 and 1996) with a silver layer plated on the external surface of the capillary instead of gold. Glass capillaries with sealed ends were first treated for 20 seconds with an electrodeless plasma discharge at reduced pressure (0.01 Torr, discharge power of 10–20 W, in a Pyrex class chamber, 0.25 L). After such plasma cleaning, the glass capillaries were activated in an acidified solution of $SnCl_2$ and 50 g of HCl per 1 L), washed with water and covered with a silver "mirror" (Yampolskii et al., 1981). This design is referred to as a capillary with an external electrode.

Figure 20B:
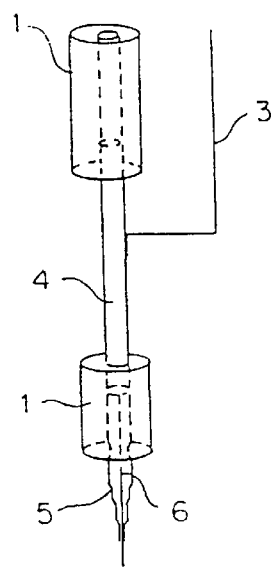

A second design, shown in FIG. 20B, is a modification of an electrospray capillary described by the laboratory of the present inventors (Morozov et al., 1993). In this capillary metal electrode (tungsten or stainless steel wire) is not exposed to a gas phase, thus reducing the risk of cornea discharge at high voltages. This second design is referred to as a capillary with an inner electrode.

Figure 20C:
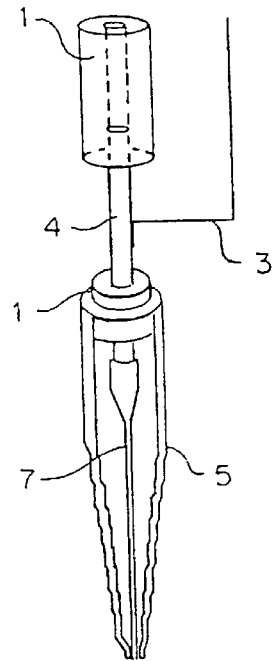

In a third design, of the capillary (referred to as a bridge capillary), contact of protein solutions with a metal electrode was completely avoided by introducing a liquid bridge between them. As shown in FIG. 20C, the external surface of the stainless steel tube 4 is used as an electrode exposed to the interior of the remote end of the large external capillary. Since the cross-section of the external capillary 5 is more than ten times larger than that of the inner capillary 7, the conductivity of the external capillary exceeds more than 100 times the conductivity of the inner capillary, making most of the current go through the large external capillary 5, whereas the internal plastic capillary 7 is used to supply protein solution.

A microprocessor controlled syringe pump (Cole-Parmer, Niles, Ill.) in combination with a 10 $\mu L$ Hamilton microsyringe was used to feed the electrospray capillaries. The flow rate was 6–9 $\mu L/h$, and the outer diameter of the capillary tips varied in different experiments between 50 and 100 $\mu m$.

Chamber with Controlled Humidity. To control humidity during electrospray experiments with enzymes and to protect protein samples from contamination with dust particles present in the ambient air, the electrospray deposition was performed in a small (0.5 L) nearly cubic acrylic box, schematically presented in FIG. 21. A glass window was glued to one side of the box to enable sharp observation of the electrospray torch and substrate under a stereo microscope. The humidity and temperature inside the chamber were measured with solid state digital sensors (Fisher) with 2–4% precision for humidity and 0.2° C. for temperature. To increase the rate of sensor response and to keep the same humidity in all parts of the chamber, the air was stirred with a small fan. Dry air from a tank or air bubbled through water was introduced into the chamber until the required humidity was reached. The fan was then stopped, and electrospray initiated. Occasionally, portions of dry or wet gas were added during the spray experiment if the humidity deviated by more than 3–5% from the required level.

Mass Measurements of the Electrospray-Deposited Proteins. A home-built Quartz Crystal Microbalance (QCM; Sauerbrey, 1959) was used to measure the mass of the electrospray-deposited protein. The microbalance was made of commercial AT-cut quartz crystals (12–17 MHz, with silver electrodes of 5 mm in diameter) after removal of their protective shells. QCM calibration was performed using 0.1% solution of sugar in water. A microdroplet of this solution with a volume which varied between 0.25 and 1.0 $\mu L$ was placed in the middle of the quartz electrode using a syringe pump with a Hamilton 10 $\mu l$ microsyringe and dried as a spot of 1–1.5 mm in diameter. After solvent evaporation under a stream of ambient air, the quartz was placed in a closed chamber and further dried in a flow of dry nitrogen or dry air until no changes in its resonance frequency were observed. A difference between the resonance frequency of the clean crystal and the resonance frequency of the crystal dried sugar spot was calculated for every sugar mass. Calibration curves were linear in the range 0–2 $\mu g$ with 2–3% of r.m.s. deviations of experimental points from the linear regression line. To diminish scatter of experimental points, deposition should be made in the center of the quartz electrode since the electrode periphery is less sensitive to mass deposition (Sauerbrey, 1959).

Figure 21:
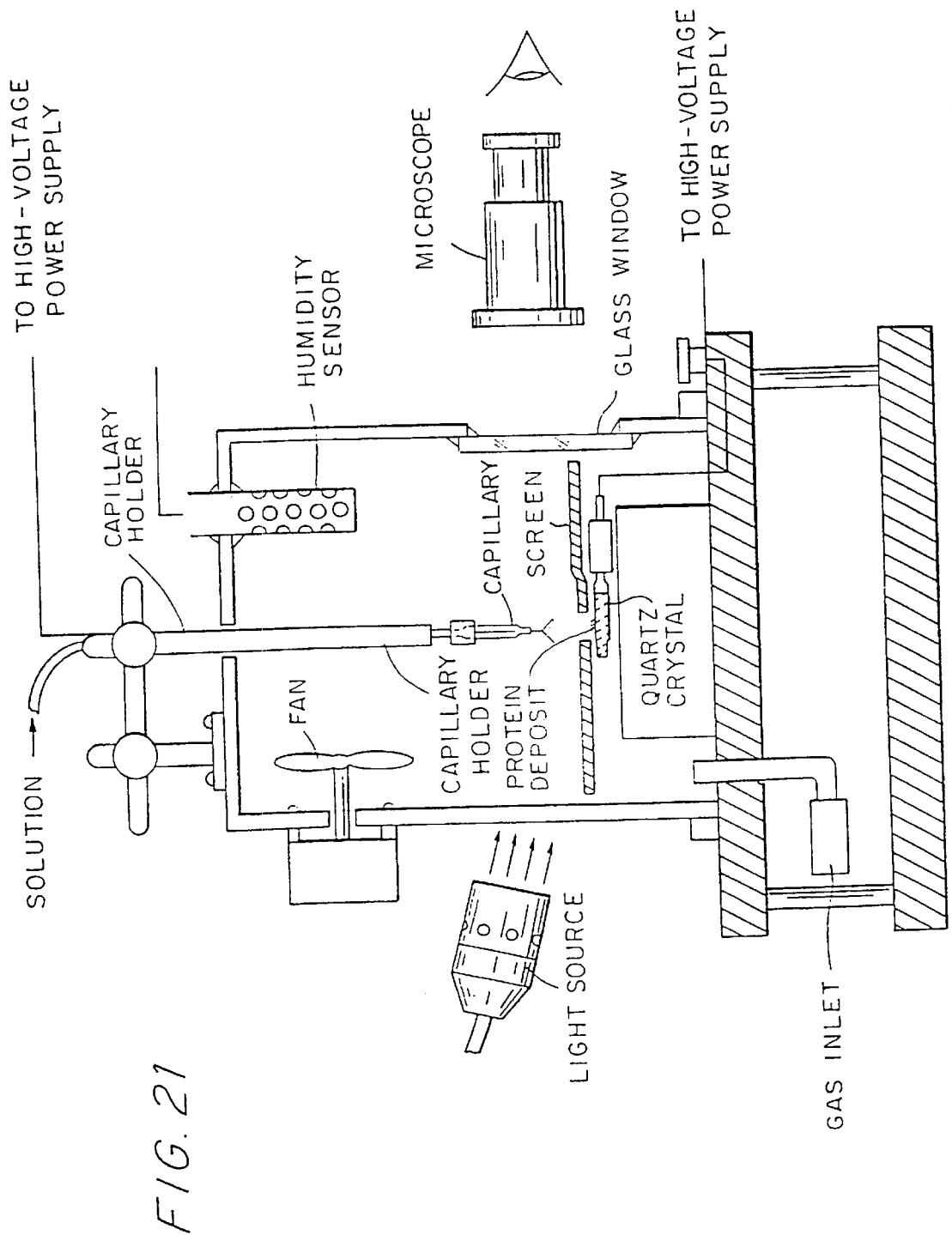

Electrospray deposition of proteins on a quartz electrode was performed as shown schematically in FIG. 21. The electrode was grounded and a plastic screen made of Teflon® or Parafilm® was placed- on the crystal with a hole positioned over the center of the electrode. After protein deposition, the quartz crystal was placed into a drying chamber of QCM, connected to the oscillator circuit and dried until constant frequency was achieved. The dry mass of the protein deposit was then determined from the shift in the quartz resonance frequency using the calibration curve. The protein concentration in dialyzed AP solution was determined by drying 1 $\mu L$ of the solution on the quartz electrode and measuring the mass of the dry residue as described above.

Measurements of Specific Activity of AP Deposit. A commercial dry powder of AP (Sigma Chemical Co.) was dissolved in water in a concentration of approximately 1 mg/mL, dialyzed overnight against a solution of $10^{-5}$ M $MgCl_2$, $10^{-5}$ M $ZnCl_2$, pH=7–8, centrifuged at 3,000×g for 1–2 minutes and kept at –20° C. Before the experiment, the stock solution was thawed, diluted five times with water and centrifuged again. Electrospray capillary, tubing and microsyringe were filled with the protein solution. No bubbles were allowed to penetrate the system.

Typically, 1 $\mu L$ of the protein solution was electrosprayed in each deposition. After measuring the dry mass of the deposit as described above, a protein spot was then extracted 3–4 times with 1–2 $\mu L$ droplets of buffer solution (0.2 M TRIS/HCl buffer, pH=9.5, 1 mM $MgCl_2$, 0.1% Tween 20). The extracts were then combined and diluted to a final 40 $\mu L$ volume with the same buffer. In the case of carbohydrates present in the electrosprayed protein solution, the weight of protein in the solution was calculated assuming that the protein-to-carbohydrate ratio was not changed upon electrospray deposition.

AP activity was measured immediately after spot extraction by adding 5–20 $\mu L$ of the extract solution to 1.0 mL of the p-NPP solution in the TRIS/HCl buffer prepared from Sigma Fast tablets. Activity was measured in a room with a thermostat, with a temperature of 25±1° C. The activities, as determined by linear regression analysis of adsorbance measurements at 410 nm record for 2–5 minutes with a computer-controlled spectrophotometer (AVIV, model 118DS), exhibited linear dependence upon enzyme concentration. The specific activity was calculated using protein concentration measured gravimetrically, as described above in the mass measurement section.

Every series of deposition experiments was accompanied by measurements of the specific activity of AP in solution prepared for electrospray deposition and in dried samples. In the latter case, 1 µL of an AP solution was applied directly onto a quartz electrode and dried in a flow of air. After measurement of its dry mass, the deposit was extracted, and its activity was measured as described for electrospray-deposited samples.

Effect of Carbohydrates. To study the effect of sucrose and trehalose on recovery of AP activity after drying, microdroplets (5 µL) of diluted AP solutions were placed onto a glass surface, and equal volumes of water or water solution containing different amounts of carbohydrates were added to each droplet. Well-mixed droplets were dried in a desiccator under a reduced pressure created with a water pump. Dry spots were then dissolved, and their activity was measured, as described for electrospray-deposited spots.

RESULTS AND DISCUSSION

Measurements of Mass of Electrospray-Deposited Samples. The deposited mass was determined from a shift in resonance frequency of quartz oscillations. However, not only the mass of the deposit but other factors may affect the frequency shift, particularly, the visco-elastic properties of the deposit. Protein samples obtained in electrospray deposition under different conditions of humidity have very different internal structure and packing density; they are opaque or opalescent when prepared at humidity, A<50%, and transparent and quite invisible (similar to those obtained upon drying) if electrospray-deposited under humidity, A >70%. The possible effect of such structural changes on QCM measurements of deposit mass were checked in special experiments. After a measurement of quartz resonance frequency with dry electrospray deposit obtained at low humidity, the quartz with the deposit was placed for 30–60 seconds in a Petri dish with A=100%, dried again, and then its resonance frequency was remeasured. An opalescent deposit was transformed into a transparent film as a result of this treatment; however, no changes in resonance frequency accompanied this transformation. It is believed that the observed variations in structure of electrospray deposits under different humidities do not affect mass measurements.

Electrospray Deposition Efficiency. The electrospray efficiency is defined as a ratio of dry mass of electrospray-deposited sample to dry mass of protein sample dried from the same volume of the same protein solution. This value shows a marked dependence on (1) the diameter of the hole, d, through which the sample is deposited, (2) the distance, h, from capillary tip to the quartz electrode, (3) voltage, V, used in electrospray deposition, and (4) the design of the electrospray capillary. With typical geometrical parameters, h=10–15 mm, d=2 mm, and low voltage, V=+(3–4) kV, the electrospray deposition efficiency varied between 60% and 80% depending on capillary design, as is shown in the results in Table 2. The slightly lower efficiency of the bridge-type capillary can be explained by a leakage of part of the protein solution into the liquid bridge, since AP has pI=4.4 (Engström, 1961). AP molecules are negatively charged at pH>4.4 and should move towards a positively charged electrode in these experiments.

TABLE 2

Electrospray Deposition Efficiency and Percentage of Recovery of Specific AP Activity Upon Electrospraying with Different Capillaries under Identical Conditions[1]

| | Internal Electrode | External Electrode | Bridge Type |
|---|---|---|---|
| Activity[2] % | 55 ± 10 | 32 ± 9 | 31 ± 12 |
| Efficiency[3] % | 79 ± 7 | 78 ± 8 | 62 ± 9 |

[1]Voltage at capillary, V = +(3–4) kv, current I = 1–50 nA, solution flow rate of 0.1 μL/min, distance between tip and quartz surface is 10 mm, humidity in the electrospray chamber A = 65 ± 5%
[2]Ratio of specific activity of the electrospray-deposited AP to that in the initial solution.
[3]Ratio of mass of the electrospray-deposited sample to the mass of protein in the electrosprayed solution volume.

1 Voltage at capillary, V=+(3–4) kv, current I=1–50 nA, solution flow rate of 0.1 μL/min, distance between tip and quartz surface is 10 mm, humidity in the electrospray chamber A=65±5%

2 Ratio of specific activity of the electrospray-deposited AP to that in the initial solution.

3 Ratio of mass of the electrospray-deposited sample to the mass of protein in the electrosprayed solution volume.

Electrospray deposition from a capillary with an internal electrode has not revealed any dependence of the efficiency on humidity. Averaged over 48 independent measurements under humidity varying between 10% and 90%, the electrospray deposition efficiency was 74±6%, if V=3–4 kV. A voltage increase to 6–7 kV resulted in an increase of electrospray deposition efficiency to 100%.

Specific Activity of Electrospray-Deposited AP. The percent ratio of specific activity of AP after dissolution of the electrospray deposit to the specific activity of AP in initial solution is used as a measure of the preservation of the native properties of a protein in electrospray deposition. As can be seen from the data presented in FIGS. 18A and 18B, AP is subjected to the largest damage and loses nearly all of its activity when electrospray deposition is performed under the conditions of high voltage (V>7–8 kV) and current (I>500–1500 nA). The following factors may be thought of as contributing to the AP inactivation under these conditions: (i) inactivation inside the electrospray capillary due to electrochemical reactions occurring on the electrode; (ii) inactivation as a result of reaction with corona discharge product in the gas phase; (iii) inactivation as a result of impact with target electrode; and (iv) inactivation as a result of drying. The last factor, (iv), is expected to have an effect similar to that of direct drying and to be independent of current and capillary design. As shown in FIGS. 18A, 22 and 23, AP is inactivated (by approximately 45%) upon direct drying on glass in vacuum, upon drying in air flow on silver electrode of QCM and upon electrospray deposition from the capillary with the internal electrode at humidity A=65% and currents not exceeding 50 nA. Under similar currents and humidity, AP was notably more inactivated (by 70%) when electrospray-deposited from the two other capillary designs (see Table 2).

The superiority of the capillary with the internal electrode over the capillary with the liquid bridge appears surprising and unexplainable if electrochemical reaction is assumed to be the main damaging factor in electrospray deposition. As shown by the lower curves in FIGS. 18A and 18B, the capillary with the internal electrode is notably less damaging than the capillary with the external electrode under all voltages and currents, which is also difficult to explain by electrochemical reaction in the capillary. The activity of AP deposited at low current from capillaries with internal and external electrodes was measured and compared before and after electrospray deposition with a current of 1500 nA from the same capillary. It was expected that electrochemical products, accumulated in the capillary with AP directly oxidized by the electrode or damaged by the low pH from the oxidation of water inside the capillary, would result in a diminished activity of the successive electrospray deposition.

Bovine intestinal AP is known to be irreversibly inactivated (McComb et al., 1979) by exposure to a pH below 4.5–5.0, and estimates of van Berkel et al. (1979) show that the pH can drop up to pH=3–4 with current I=250 nA, and flow rate of 1 $\mu$L/min. However, no notable difference between specific AP activity of the preceding and successive deposits was found for both types of electrospray capillaries. It is believed, therefore, that the inactivation of AP at high voltages and currents occur outside the capillary as a result of reaction with the products of corona discharge or as the result of impact with the target electrode. Impact energy should grow with an increase of the potential, causing protein distraction on impact. This can explain the increase in AP inactivation with increasing voltage and current. The generation of corona products in electrospray deposition at I>200–300 nA was noticeable from a characteristic smell of ozone in the electrospray chamber. The maintenance of a high current even after the pump was switched off and the disappearance of a visible electrospray torch was also indicative of the presence of corona discharge under these conditions. It was also found that electrospray at a high current resulted in the removal of Ag-plating from the capillary tip. The capillary with the external electrode supports corona discharge more readily than the capillary with the internal electrode, which explains why AP is inactivated at lower currents and to a higher extent when electrospray deposited from the capillary with the external electrode. It is noteworthy that contamination of the AP deposit with Ag ions does not seem to contribute to the inactivation of AP deposited from the capillary with the external electrode, since the addition of $10^{-4}$ M AgNO$_3$ to the AP solution does not result in any inhibition.

Regardless of the mechanism of inactivation in electrospray deposition at high voltages and currents, these experiments establish that AP preserves as much of its activity as during direct drying, provided that electrospray deposition is performed from the capillary with the internal electrode at a voltage not exceeding +4.5 kV and with a current less than 50 nA. It is believed that, under these conditions, all damaging factors listed above do not occur and that the drying process itself seems to be the only remaining inactivating factor left.

Figure 18A:
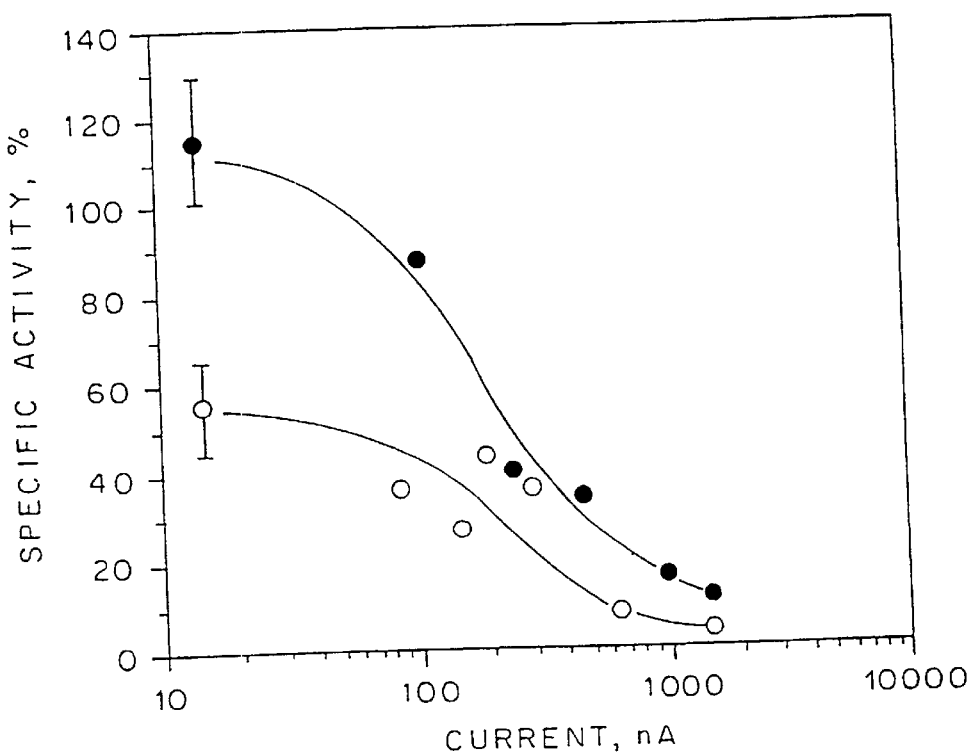
Figure 18B:
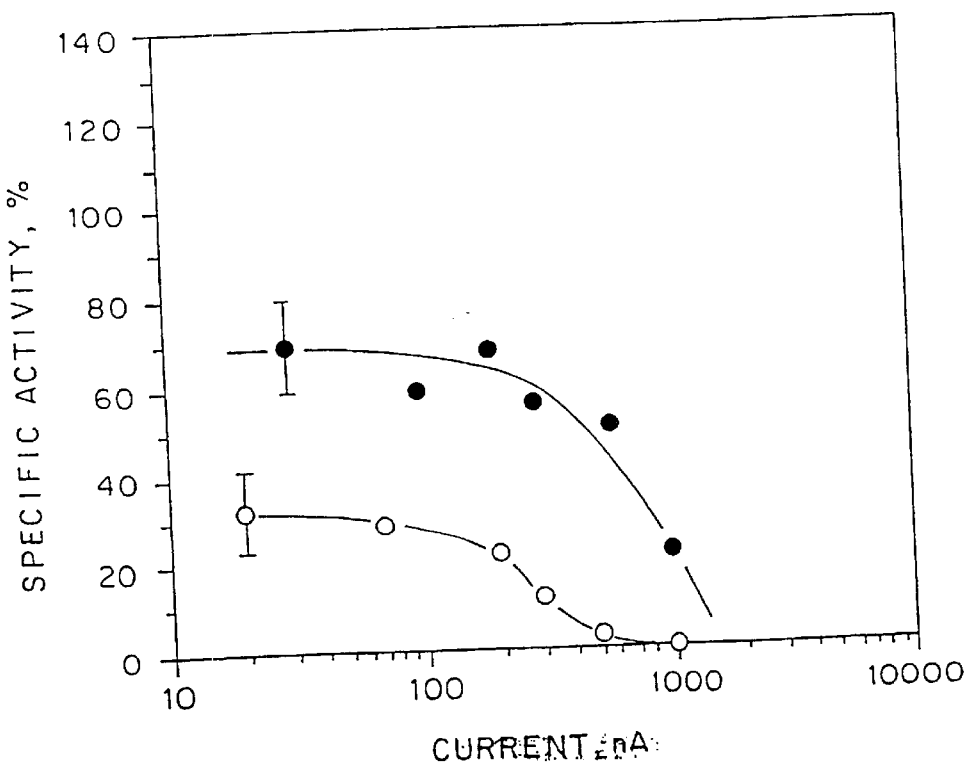
Figure 22:
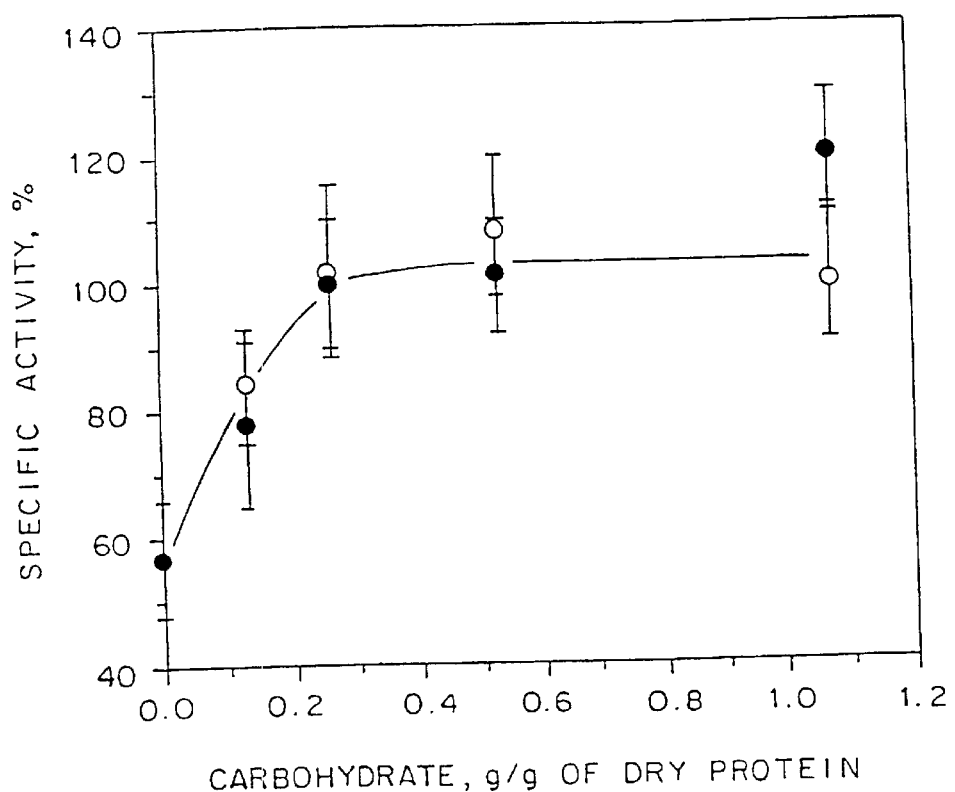
Figure 23:
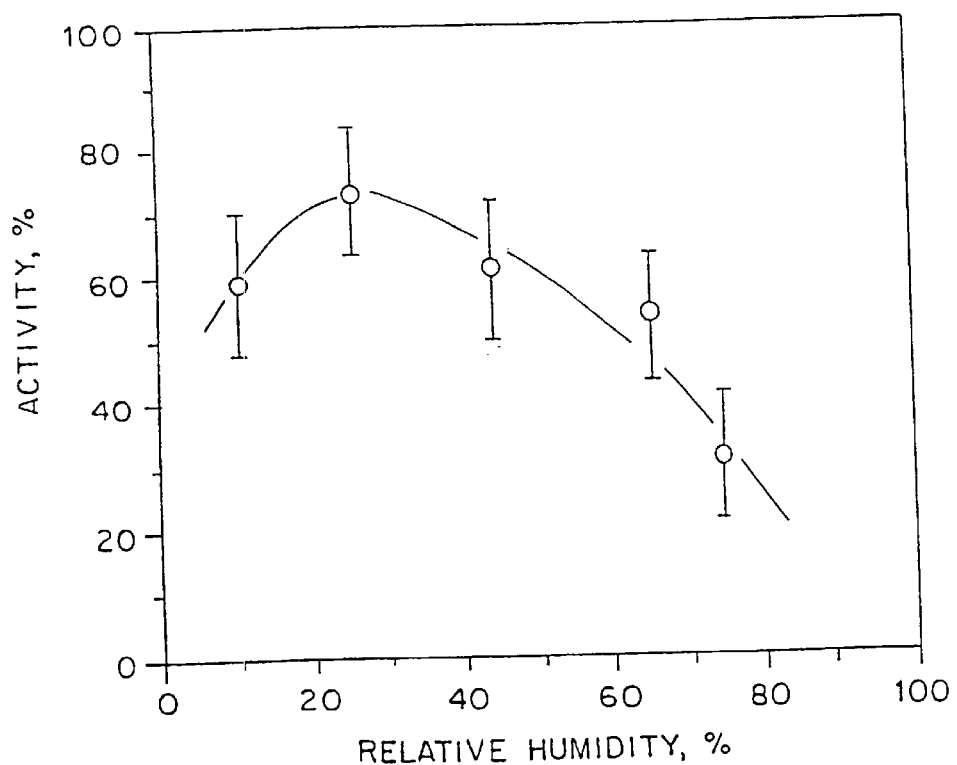

It has been well documented that many proteins lose their activity when subjected to freeze-drying, and some of them were found to be completely inactivated upon freeze-drying or drying at room temperature (Crowe et al., 1987; Gibson et al., 1992). It is also well known that disaccharides are capable of protecting proteins upon drying (Gibson et al., 1992). The data presented in FIG. 22 indicate that AP is equally well protected from inactivation by drying by both sucrose and trehalose. The addition of 50% (w/w) of the disaccharides is enough to preserve 100% of AP activity. The upper curve in FIG. 18A shows that the same substance, sucrose, that protects AP activity upon drying, protects equally well in electrospray deposition. Taken at the same concentration (50% w/w) of sucrose, which serves to protect 100% of AP activity upon drying, the presence of sucrose increases the recovery of AP activity of the electrospray-deposited enzyme to 100% as well, provided that the electrospray deposition was performed at a low current and from a capillary with an internal electrode. These results point to the idea that drying is the main damaging factor under these electrospray conditions. The results of FIG. 23 show that rapid drying of electrospray-generated droplets in the gas phase under low humidity is seen to be even less damaging to AP activity (30% decrease) than slow drying the AP solution on the surface (45% decrease shown in FIG. 22). However, the enzyme is subjected to greater damage if electrospray deposition is performed at a humidity higher than 60%, presumably due to multiple cycles of wetting/drying accompanying the fall of microdroplets, which cannot become completely dry on traveling to the substrate under this condition. In short, the functional activity of AP can completely survive electrospray deposition onto a metal electrode when the electrospray deposition is performed under mild conditions in the presence of protective substances.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Bertolini et al., *Nucl. Instr. Meth.* 32:355–356, 1965.
Bhatia et al., *Anal. Biochem.* 208:197–205 (1993).
Blumberg et al., LA-2711 (1962).
Bruninx et al., *Nucl. Instr. Meth.*, 13:131–140 (1961).
Buchko et al., in *Materials Research Society Symposium Proceedings*, Cotell et al. (Eds.), MRS, Pittsburgh, Pa., 414:23–28 (1996).
Cheng et al., *Nucl. Acids Res.*, 24:2183–2189 (1996).
Crowe et al., *Biochem. J.*, 242:1–10 (1987).
Engström, L., *Biochem. Biophys. Acta* 52:36–41 (1961).
Fodor et al., *Science*, 251:767–773 (1991).
Gibson, et al., In *Biosensors and Chemical Sensors; ACS Symp. Ser.*, Edelman et al. (Eds.), ACS, Washington DC, 487:40–55 (1992).
Hames et al., *Nucleic Acid Hybridization*, IRL Press, Washington, DC, 1987, pp. 87–90.
Hart et al., *Electroanalysis* 6:617–624 (1994).
Hermanson et al., *Immobilized Affinity Ligand Techniques*, Academic Press, New York (1991).
Johnson et al., In: *Diagnostic Biosensor Polymers*, eds. A. M. Usmani and N. Arkmal, American Chemical Society, Washington DC, 1994, pp. 84–95.
McComb et al., *Alkaline Phosphatase*, Plenum Press, New York (1979).
Michelson, D., *Electrostatic Atomization*, IOP Publishing, New York, 1990.
Morozov et al., *Int. Scanning Microscopy* 7:757–779 (1993).
Nakamoto et al., *Sens. Actuators* 13:165 (1988).
Newman et al., *Anal. Chem. Acta* 262:13–17 (1992).
Pease et al., *Proc. Natl. Acad. Sci. USA* 91:5022–5026 (1994).
Pritchard et al., *Anal. Chem.* 67:3605–3607 (1995).
Reimann et al., *Nucl. Instr. and Meth. in Phys. Res.*, B88:29–34 (1994).
Reiser et al., *rans. Faraday Soc.*, 65:2168–2185 (1969).
Robinson, P. S., *Nucl. Instr. Meth.* 40:136–140 (1995).
Sauerbrey, G., *Zeitschr. fur Phys.*, 155:206–222 (1959).
Shalon et al., *Genome Research*, 6:639–645 (1996).
Strike et al., In: *Diagnostic Biosensor Polymers*, eds. A. M. Usmani and N. Akmal, American Chemical Society, Washington DC, 1994, pp. 299–306.
Sullivan et al., *J. Am. Soc. Mass Spectrom.*, 7:329–341 (1996)
Thundat et al., *Ultramicroscopy* 42–44:1083–1087 (1992).
van Berkel et al., *Int. J. Mass Spectrom and Ion Processes*, 162:55–67 (1997).
van der Eijk et al., *Nucl. Instr. Meth.* 112:343–351 (1973).
Wilm, et al., *Int. J. Mass Spectrom. Ion Processes*, 136:167–180 (1994).
Wilm, et al., *Anal. Chem.*, 68:1–8 (1996).

What is claimed is:

1. A method for fabricating a deposit of a non-volatile biologically functional and/or biologically active substance on a substrate, comprising:

electrospraying a solution of said non-volatile biologically functional and/or biologically active substance under a voltage effective to atomize said solution without destroying the functional properties of the non-volatile biologically functional and/or biologically active substance; and depositing the electrosprayed substance in the form of dry deposit on contact with a surface of the substrate as the biologically functional and/or biologically active substance.

2. The method in accordance with claim 1, wherein during said electrospraying and depositing steps, electrostatic charge on the electrosprayed substance deposited on the surface of the substrate is neutralized.

3. The method in accordance with claim 2, wherein the substrate is made of an electrically conductive material, and the electrostatic charge on the electrospray products are neutralized by a local increase in conductivity of a dielectric layer placed on the substrate.

4. The method in accordance with claim 3, wherein the dielectric layer is made of a photo-conductive material and the local increase in conductivity of the dielectric layer is performed by locally irradiating the photo-conductive insulating layer with light.

5. The method in accordance with claim 3, wherein the dielectric layer is made locally conductive by injection of charge carriers from an external source and the local increase in conductivity of the dielectric layer is performed by locally injecting charge carriers into the dielectric layer.

6. The method in accordance with claim 3, wherein the dielectric layer is made of a thermally conductive material, and the local increase in conductivity of the dielectric layer is performed by locally heating the dielectric layer.

7. The method in accordance with claim 3, wherein the local increase in conductivity is made by perforating the dielectric layer.

8. The method in accordance with claim 3, wherein the size of a deposit of the non-volatile biologically functional and/or biologically active substance on the surface of the substrate is smaller than the size of an area in which conductivity is locally increased.

9. The method in accordance with claim 3, wherein a plurality of confined electrostatic fields are created on the substrate to deposit simultaneously a plurality of non-volatile biologically functional and/or biologically active substances on the substrate.

10. The method in accordance with claim 9, wherein the position of said plurality of confined electrostatic fields is shifted and said electrospraying and depositing steps are repeated.

11. The method in accordance with claim 10, wherein a solution comprising a different non-volatile biologically functional and/or biologically active substance is deposited in a repetition of said electrospraying and depositing steps.

12. The method in accordance with claim 3, wherein a collecting ring is provided around the substrate area with increased conductivity.

13. The method in accordance with claim 12, wherein a potential is applied to the collecting ring so as to achieve stable electrospray with a maximum fraction of the total current from a capillary passing through the substrate.

14. The method in accordance with claim 2, wherein said depositing step is conducted such that a deposit of said biologically functional and/or biologically active substance is formed at a predetermined position on the substrate, and in a predetermined form and shape under control of an electrostatic field.

15. The method in accordance with claim 2, wherein the deposited non-volatile biologically functional and/or biologically active substance forms a film.

16. The method in accordance with claim 15, wherein said film of the deposited non-volatile biologically functional and/or biologically active substance has a non-round shape.

17. The method in accordance with claim 15, further comprising a step of applying a conductive or semiconductive layer onto a substrate before electrospraying, whereby the conductive or semiconductive layer provides a surface for depositing the film by electrospray.

18. The method in accordance with claim 17, further comprising a step of detaching the film of the non-volatile biologically functional and/or biologically active substance from the conductive or semiconductive layer.

19. The method in accordance with claim 18, wherein the conductive layer contains a chemically or physically solubilized material.

20. The method in accordance with claim 19, wherein the conductive layer contains hydrophilic polymers.

21. The method in accordance with claim 15, wherein the surface on which the electrosprayed film is deposited is a surface of a substrate having low conductivity.

22. The method in accordance with claim 21, wherein the surface on which the electrosprayed film is deposited is porous.

23. The method in accordance with claim 1, wherein a dielectric protective screen is disposed around a capillary to surround the electrosprayed products and prevent scatter.

24. The method in accordance with claim 23, wherein said dielectric protective screen is perforated.

25. The method in accordance with 1, wherein the electrosprayed solution further comprises a stabilizer.

26. The method in accordance with claim 1, wherein the non-volatile biologically functional and/or biologically active substance is a biomacromolecule.

27. The method in accordance with claim 26, further comprising the step of cross-linking the sample of deposited biomacromolecule.

28. The method in accordance with claim 27, wherein the biomacromolecule is a protein.

29. The method in accordance with claim 28, wherein the electrosprayed solution further comprises a soluble protein stabilizer.

30. The method in accordance with claim 29, further comprising the step of washing away the protein stabilizer from the cross-linked protein film to obtain a porous protein film.

31. The method in accordance with claim 28, further comprising the step of contacting the deposited protein film with a reagent to produce a homogeneous film.

32. The method in accordance with claim 31, wherein the reagent is water vapor.

33. The method in accordance with claim 28, wherein the protein is deposited as nanoclusters of protein molecules with a size of the cluster between 5 and 50 nm.

34. The method in accordance with claim 33, wherein the step of electrospraying is conducted in an atmosphere in the range of about 10% to 40% humidity.

35. A protein film produced by the method according to claim 33, wherein the deposited nanoclusters of protein molecules are densely packed but not completely coalesced and said film has intercluster channels penetrable by ligands.

36. The method in accordance with claim 26, wherein the biomacromolecule is a nucleic acid molecule.

37. The method in accordance with claim 1, wherein the solution containing the non-volatile biologically functional and/or biologically active substance is electrosprayed from a capillary, which capillary is set to a potential to effect sufficient electrospray without resulting in a corona discharge.

38. The method in accordance with claim 37, wherein a current in a range of about 1–50 nA is maintained through the capillary.

39. The method in accordance with claim 1, wherein the solution containing a non-volatile biologically functional and/or biologically active substance has a conductivity less than about 500 microSiemens per cm.

40. The method in accordance with claim 1, further comprising a step of preventing intermolecular reaction between deposited electrospray products or between deposited electrospray products and molecules present on the substrate.

41. The method in accordance with claim 1, wherein said electrospraying is performed with capillaries.

42. The method in accordance with claim 1, wherein said voltage effective to atomize said solution without destroying the functional properties of the non-volatile biologically functional and/or biologically active substance is less than 7–8 kV at a current less than 500–1500 nA.

43. A method for fabricating a deposit of a non-volatile biologically functional and/or biologically active substance on a substrate, comprising:

electrospraying a solution of said non-volatile biologically functional and/or biologically active substance under conditions which prevent corona discharge with partial or complete evaporation of solvent; and depositing the electrosprayed biologically functional and/or biologically active substance on a surface of the substrate as a dry charged residue or as a highly concentrated solution.

* * * * *